(12) United States Patent
Saitou et al.

(10) Patent No.: US 7,884,193 B2
(45) Date of Patent: Feb. 8, 2011

(54) ANTIBODIES FOR IDENTIFICATION OF MURINE FRAGILIS EXTRACELLULAR DOMAIN AND METHODS FOR IDENTIFYING PLURIPOTENT CELLS

(75) Inventors: Mitinori Saitou, Cambridge (GB); Azim Surani, Cambridge (GB)

(73) Assignee: Cambridge Enterprises Limited, Cambridge (GB)

( * ) Notice: Subject to any disclaimer, the term of this patent is extended or adjusted under 35 U.S.C. 154(b) by 548 days.

(21) Appl. No.: 11/497,472

(22) Filed: Aug. 1, 2006

(65) Prior Publication Data

US 2006/0275839 A1 Dec. 7, 2006

Related U.S. Application Data

(60) Division of application No. 10/646,390, filed on Aug. 21, 2003, now Pat. No. 7,226,994, which is a continuation-in-part of application No. 10/621,911, filed on Jul. 17, 2003, now abandoned, and a continuation-in-part of application No. PCT/GB02/00215, filed on Jan. 18, 2002.

(30) Foreign Application Priority Data

Jan. 18, 2001 (GB) ................................ 0101300.2

(51) Int. Cl.
    C07K 16/00    (2006.01)
    C07K 16/18    (2006.01)
    C07K 16/28    (2006.01)
    C12P 21/08    (2006.01)

(52) U.S. Cl. .............. 530/387.1; 530/387.3; 530/387.9; 530/388.1; 435/325

(58) Field of Classification Search ........................ None
    See application file for complete search history.

(56) References Cited

U.S. PATENT DOCUMENTS 6,709,855 B1 *  3/2004  Stanton et al. ............ 435/283.1

FOREIGN PATENT DOCUMENTS

WO         9938973 A2    5/1999

OTHER PUBLICATIONS

Takahashi (Cell vol. 126, Issue 4, Aug. 25, 2006, pp. 663-676).*

Munsie et al., Current biology : CB, (Aug. 24, 2000) vol. 10, No. 16, pp. 989-992.*
Lewin et al., "Molecular Analysis of a Human Interferon-Inducible Gene Family," Euro J. Biochem (1991) vol. 199; 417-432.
Shimada et al., "Analysis of Genes Under the Downstream Control of the t(8;21) Fusion Protein AML-MTG8: Overexpression of the TIS11b (ERF-1, cMG1) Gene Induces Myeloid Cell Proliferation in Response to G-CSF," Blood, Jul. 15, 2000, vol. 96, No. 2.
Sasaki et al., "Characterization of Gene Expression in Mouse Blastocyst Using Single-Pass Sequencing of 3995 Clones," Genomics (1998) 49: 167-179.
Yeom et al., "Germline Regulatory Element of Oct-4 Specific for the Totipotent Cycle of Embryonal Cells," Development (1996) 112:881-894.
Nurcombe et al., "MK: A pluripotential embryonic stem-cell-derived neuroregulatory factor," Development (1992) 116:1175-1183.
"Functional Annotation of a full-length mouse cDNA collection," Nature (2001) 409:685-690.
Saitou et al., "A Molecular Programme for the Specification of Germ Cell Fate in Mice," Nature (2002) 418:293-300.
PIR accession No. JC1241, submitted by Hayzer et al., Sep. 30, 1993.
Hayzer, D.J., et al., "A rat beta-interferon-induced mRNA: sequence characterization," GENE 117(1992) 277-278.
Geijsen, Niels et al., Derivation of embryonic germ cells and male gametes from embroyinic stem cells, Nature 427 (2004) 148-154.
Gordeeva, O., et al., Differentiation of embryonic stem cells after transplantation into peritoneal cavity of irradiated mice . . . , Transplantation Proceed., 37 (2005) 295-298.
Ginsburg et al., Development 110; 521-528, 1990.
EMBL: AA059844 XP002222772 (Mar. 3, 2000).
EMBL: X61381 XP002222773 (May 26, 1992).
EMBL: A1606389 XP002222774 (Mar. 4, 2000).
NCBI: AC094826 XP002222775 (Sep. 15, 2001).
NCBI: AC097234 XP002222776 (Dec. 20, 2001).
NCBI: AC093991 XP002222777 (Dec. 20, 2001).
NCBI: AC103122 XP002222778 (Dec. 21, 2001).
NCBI: AC106604 XP002222779 (Jan. 12, 2002).
EMBL: AB030416 XP002223547 (Jan. 31, 2000).
EMBL: C89109 XP002223548 (May 28, 1998).
EMBL: C89043 XP002223549 (May 28, 1998).
NCBI: AK010723 XP002223550 (Feb. 8, 2001).
NCBI: AK003407 XP002223551 (Feb. 8, 2001).
EMBL: AK007919 XP002223552 (Feb. 8, 2001).

* cited by examiner

*Primary Examiner*—Gary B. Nickol
*Assistant Examiner*—Daniel C Gamett
(74) *Attorney, Agent, or Firm*—Whyte Hirschboeck Dudek S.C.

(57) ABSTRACT

We describe two primordial germ cell-specifically expressed genes, GCR1 (Fragilis) and GCR2 (Stella), as well as their fragments, homologues, variants or deriviatives thereof which are markers for primordial germ cells and may be used to identify such cells in cell populations.

13 Claims, 29 Drawing Sheets

FIG. 1

```
GCCGCAGAAAGGGCAGACCCGCAGCGCGCTCCATCCTTTGCCCTCCAGTGCTGCCTTTGC    60
TCCGCACCATGAACCACACTTCTCAAGCCTTCATCACCGCTGCCAGTGGAGGACAGCCCC   120
          M  N  H  T  S  Q  A  F  I  T  A  A  S  G  G  Q  P  P

CAAACTACGAAAGAATCAAGGAAGAATATGAGGTGGCTGAGATGGGGGCACCGCACGGAT   180
 N  Y  E  R  I  K  E  E  Y  E  V  A  E  M  G  A  P  H  G  S

CGGCTTCTGTCAGAACTACTGTGATCAACATGCCCAGAGAGGTGTCGGTGCCTGACCATG   240
 A  S  V  R  T  T  V  I  N  M  P  R  E  V  S  V  P  D  H  V

TGGTCTGGTCCCTGTTCAATACACTCTTCATGAACTTCTGCTGCCTGGGCTTCATAGCCT   300
 V  W  S  L  F  N  T  L  F  M  N  F  C  C  L  G  F  I  A  Y
              TMI

ATGCCTACTCCGTGAAGTCTAGGGATCGGAAGATGGTGGGTGATGTGACTGGAGCCCAGG   360
  A  Y  S  V  K  S  R  D  R  K  M  V  G  D  V  T  G  A  Q  A

CCTACGCCTCCACTGCTAAGTGCCTGAACATCAGCACCTTGGTCCTCAGCATCCTGATGG   420
 Y  A  S  T  A  K  C  L  N  I  S  T  L  V  L  S  I  L  M  V
                                        TMII

TTGTTATCACCATTGTTAGTGTCATCATCATTGTTCTTAACGCTCAAAACCTTCACACTT   480
 V  I  T  I  V  S  V  I  I  I  V  L  N  A  Q  N  L  H  T  *
(SEQ ID NO:2)
AATAGAGGATTCCGACTTCCGGTCCTGAAGTGCTTCACCCTCCGCAGCTGCGTCCCTCCT   540
TGCCCCTCCCTACACGCAGGTGTAACACTCATTTATCTATCCACAGTGGATTCAATAAAG   600
TGCACTTGATAACCACC (SEQ ID NO:1)
```

FIG. 2

```
GGATCACAGACTGACTGCTAATTGGGTCTTGGTTTTAGGTCTTTTCAAAGACTAAGCAAT 60
CTTGTTCCGAGCTAGCTTTTGAGGCTTCTGCCCATCGCATCGCCATGGAGGAACCATCAG 120
                                            M  E  E  P  S  E

AGAAAGTCGACCCAATGAAGGACCCTGAAACTCCTCAGAAGAAAGATGAAGAGGACGCTT 180
 K  V  D  P  M  K  D  P  E  T  P  Q  K  K  D  E  E  D  A  L

TGGATGATACAGACGTCCTACAACCAGAAACACTAGTAAAGGTCATGAAAAAGCTAACCC 240
 D  D  T  D  V  L  Q  P  E  T  L  V  K  V  M  K  K  L  T  L
                                          ―――――――――――――――――
                                                          Helix I
TAAACCCCGGTGTCAAGCGGTCCGCACGCCGGCGCAGTCTACGGAACCGCATTGCAGCCG 300
 N  P  G  V  K  R  S  A  R  R  R  S  L  R  N  R  I  A  A  V
―――――――――――――――――――――――――――――――――――――
                       ――――――――――――――――――――――――――――― Helix II
TACCTGTGGAGAACAAGAGTGAAAAAATCCGGAGGGAAGTTCAAAGCGCCTTTCCCAAGA 360
 P  V  E  N  K  S  E  K  I  R  R  E  V  Q  S  A  F  P  K  R
――――                                                ――――――――

GAAGGGTCCGCACTTTGTTGTCGGTGCTGAAAGACCCTATAGCAAAGATGAGAAGACTTG 420
 R  V  R  T  L  L  S  V  L  K  D  P  I  A  K  M  R  R  L  V
―――――――――――――――――――――――――――――――――――――――――――――――――――――――――

TTCGGATTGAGCAGAGACAAAAAAGGCTCGAAGGAAATGAGTTTGAACGGGACAGTGAGC 480
 R  I  E  Q  R  Q  K  R  L  E  G  N  E  F  E  R  D  S  E  P
―――――――――――――――――――――――――――――――――――――――――――――――――――――――――

CATTCAGATGTCTCTGCACTTTCTGCCATTATCAAAGATGGGATCCCTCTGAGAATGCGA 540
 F  R  C  L  C  T  F  C  H  Y  Q  R  W  D  P  S  E  N  A  K
―――

AAATCGGGAAGAATTAGGAGCTTACATTGTACGCTGCCCTGGCTGTCGACGATGCCGCAC 600
 I  G  K  N  *  (SEQ ID NO:4)

AGCAGATGTGAAAGCTATTTTTTGTTTAAGATTAAACTTTTTCTCGGTGCTGGGAAATCTT 660
AACTTGTTAACCTTTAAATTGTAGATAGGATGCACAACGATCCAGATTTATGTGAAGTTT 720
AGAAGCCTCAAGCTGTGACGCCCAGGGCTGAGGAATAAAGTAAATAGAATTTGGAGTATG 780
TACGTTCTAATTTCCAGAAATTTGTAATAAAAGCATTTTTGTT (SEQ ID NO:3)
```

FIG. 10a

|  | 10 | 20 | 30 | 40 |
|---|---|---|---|---|
| fragilis (mouse) | MNHTSQAFITAA | SGGQPPNYER | IKEEYEVAEMGAP | HG - - S |
| fragilis 2 (mouse) | MP | KEQQEVVVLGSP | HI - - S |
| fragilis 3 (mouse) | MSHNSQAFLSTNAG - L | PPSYET | IKEEYGVTELGEP | SN - - S |
| fragilis 4 (mouse) | | MDTSYPREDPRAP | SSRKA |
| fragilis 5 (mouse) | MVKRD . . . . . . . . . | PD - - S |
| Ifitm1 (human) | MHKEEHEVAVLGAP | PS - - T |
| Ifitm2 (human) | MNHIVQTFS - PVNSGQPPNYEML | KEEQEVAMLGGP | HN - - P |
| Ifitm3 (human) | MSHTVQTFSPVNSGQPPNYEML | KEEHEVAVLGGP | HN - - P |
| novel (human) | MDTAYPREDTRAP | TP - - S |
| 1-8U (cow) | MNRTSQLLLTGAHGAVPPAYEVL | KEEHEVAVLGAP | QS - - Q |
| 9-27 (cow) | MIKEEHEVAVLGAP | QS - - R |
| P26376 (rat) | MNHTSQAFVNAATGGQPPNYERIKEEYEVSELGAP | HG - - S |
| JC1241 (rat) | MNHTSQAFATVATGGQPPNYERIKEEYEVSELGAP | HG - - S |
| NP110460 (rat) | MSHNSQAFLPANAG - LPPSYET | IKEEYGVTELGEP | NN - - S |
| AAD48010 (rat) | MNHTSQAFVNAATGGQPPNYERIKEEYEVSELGAP | HG - - S |
|  | MNHTSQAF   A GGQPPNYE .KEEYEV .LGAP   RKS |

|  | 50 | 60 | 70 | 80 |
|---|---|---|---|---|
| fragilis (mouse) | ASVRTTVINMPREVSVP - DHVVWSLFNTLFMNFCCLGFIA |
| fragilis 2 (mouse) | TSATATTINMP - EISTP - DHVVWSLFNTLFMNFCCLGFVA |
| fragilis 3 (mouse) | AVVRTTVINMPREVSVP - DHVVWSLFNTLFNACCLGFVA |
| fragilis 4 (mouse) | DAAHTALSMGTPGPTPRDHMLWSVFSTMYLNLCCLGFLA |
| fragilis 5 (mouse) | APVPSTVVCINSDVIQP - DHITWSTFNTVFMNGCCLGFIA |
| Ifitm 1 (human) | ILPRSTVINIHSETSVP - DHVVWSLFNTLFLNWCCLGFIA |
| Ifitm 2 (human) | APPTSTVIHIRSETSVP - DHVVWSLFNTLFMNTCCLGFIA |
| Ifitm 3 (human) | APPTSTVIHIRSETSVP - DHVVWSLFNTLFMNPCCLGFIA |
| novel (human) | KAGAHTALTLGAPHPPPRDHLIWSVFSTLYLNLCCLGFLA |
| 1-8U (cow) | APLTTTVINIRSDTAVP - DHIVWSLFNTIFMNWCCLGFVA |
| 9-27 (cow) | RPLTTTVINIRSDTAVP - DHIVWSLFNTIFLNWCCLGFVA |
| P26376 (rat) | ASVRTTVINMPREVSVP - DHVVWSLFNTLFMNFCCLGFIA |
| JC1241 (rat) | ASVRTTVINMPREVSVP - DHVVWSLFNTLFMNFCCLGFIA |
| NP110460 (rat) | AVVRTTVINMPREVSVP - DHVVWSLFNTLFFNACCLGFIA |
| AAD48010 (rat) | ASVRTTVINMPREVSVP - DHVVWSLFNTLFMNFCCLGFIA |
|  | A . TTVINM  E.SVPRDHVVWSLFNTLFMN.CCLGFIA |

FIG. 10b

|  | 90 | 100 | 110 | 120 |
|---|---|---|---|---|
| fragilis (mouse) | YAYSVKSRDRKMVGD | VTGAQAYASTAKCLNI | ST | LVLSILM |
| fragilis 2 (mouse) | YAYSVKSRDRKMVGD | TTGAQAFASTAKCLNI | SS | LFFTILT |
| fragilis 3 (mouse) | YAYSVKSRDRKMVGD | VVGAQAYASTAKCLNI | SS | LIFSILM |
| fragilis 4 (mouse) | LVHSVKARDQKMAGN | LEAARQYGSKAKCYN | L | AAMWTLVP |
| fragilis 5 (mouse) | YIYSVKSRDRKMVGD | MTGAQSHASTAKILN | L | ALVISLIF |
| Ifitm 1 (human) | FAYSVKSRDRKMVGD | VTGAQAYASTAKCLNI | W | ALILGILM |
| Ifitm 2 (human) | FAYSVKSRDRKMVGD | VTGAQAYASTAKCLNI | W | ALILGFM |
| Ifitm 3 (human) | FAYSVKSRDRKMVGD | VTGAQAYASTAKCLNI | W | ALILGILM |
| novel (human) | LAYSIKARDQKVVGD | LEAARRFGSKAKCYN | L | AAMWTLVP |
| 1-8U (cow) | FAYSVKSRDRKMVGD | ITGAQSYASTAKCLNI | CS | LVLGILL |
| 9-27 (cow) | FAYSVKSRDRKMVGD | ITGAQSYASTAKCLNI | W | ALVLGILL |
| P26376 (rat) | YAYSVKSRDRKMVGD | MTGAQAYASTAKCLNI | SS | LVLSILM |
| JC1241 (rat) | YAYSVKSRDRKMVGD | MTGAQAYASTAKCLNI | SS | LVLSILM |
| NP110460 (rat) | YAYSVKSRDRKMVGD | VIGAQAYASTAKCLNI | SS | LIFSVLM |
| AAD48010 (rat) | YAYSVK.......... | ................ | .. | .VSVLE |

YAYSVKSRDRKMVGD.TGAQAYASTAKCLNI   L.L.ILM

|  | 130 | 140 | 150 | 160 |
|---|---|---|---|---|
| fragilis (mouse) | VVITVSVIIVLNA | QNLHT (SEQ ID NO:27) |  |  |
| fragilis 2 (mouse) | ATVVVVCAIR (SEQ ID NO:28) |  |  |  |
| fragilis 3 (mouse) | VIICIIFSTTSVVFQSFAQRTPHSGF (SEQ ID NO:29) |  |  |  |
| fragilis 4 (mouse) | PLLLLGLVVTGAHLSKLAKDSAAFFSTKEDEEDYN (SEQ ID NO:30) |  |  |  |
| fragilis 5 (mouse) | YMLVLYSFNLLGNQR (SEQ ID NO:31) |  |  |  |
| Ifitm 1 (human) | TGFILLLVFGSVTVYHIMLQIIQEKRGY (SEQ ID NO:32) |  |  |  |
| Ifitm 2 (human) | TLLVIIPVLVVQAQR (SEQ ID NO:33) |  |  |  |
| Ifitm 3 (human) | TLLIVIPVLIFQAYG (SEQ ID NO:34) |  |  |  |
| novel (human) | PLLLLGLVVTGAHLARLAKDSAAFFSTKFDDADYD (SEQ ID NO:35) |  |  |  |
| 1-8U (cow) | TVVLIVLVSNGSMIVQAVSELMQNYGGH (SEQ ID NO:36) |  |  |  |
| 9-27 (cow) | TGSIVLLIFGYMAVYQTVFLLMQEKRGH (SEQ ID NO:37) |  |  |  |
| P26376 (rat) | VIITIVTVVIIANAPRLQT (SEQ ID NO:38) |  |  |  |
| JC1241 (rat) | VIITIVTVVIIANAPRLQT (SEQ ID NO:39) |  |  |  |
| NP110460 (rat) | VIICIIFSTTSAVVFQSLSQRTPHSGF (SEQ ID NO:40) |  |  |  |
| AAD48010 (rat) | VGVMV (SEQ ID NO:41) |  |  |  |

I. IV... . L .           F D    D Y (SEQ ID NO:42)

FIG. 15o

```
mouse  MEEPSEKVDPMKDPETP-------QKKDEEDALDDHDYLQ---PETLVKMKKLTLNPGVKRS 53
rat    MDEPSEKVDPVNPETQMYDGSQREDEGDSPDDSELQ-------PETLVKMKKLTLNPSAKPI 58
human  MD-PSQ-FNPTYIPGSP-------QMLTEENSRDDGASQISSETIKNLSNLTNASSESV 53
                                                         ★★★ ★ mouse  A--RRRSLRNRIAAVPVENKSEKIRREVQSAFPKRRVRTLLSVLKDPIAKMRRLIV----- 106
rat    KYHRRQRLRLQKSQPVENRSERIMREVQSAFPRRRVRTLLSVLKDPIARMRRFV------- 113
human  SPLSEALLRRESVGAAVLREIED-----EWLHSRRGVRTLLSVQREKMARIRYMLGGVR 108 mouse  RIEQRQKRLEGNEFERDSEPFRCLCTFCHYQRWDPSENAKIGKN------150  (SEQ. ID NO:43)
rat    RIEQRQOLEGNE--RRDEPFRCLCTFCHYQRWDPSENAKIGONQKN----158  (SEQ. ID NO:44)
human  THERRPTKEPKGVKKSRPEKCPCSECVSNGWDPSENAIGNDTKPLQP 159  (SEQ. ID NO:45)
```

FIGURE 16
a
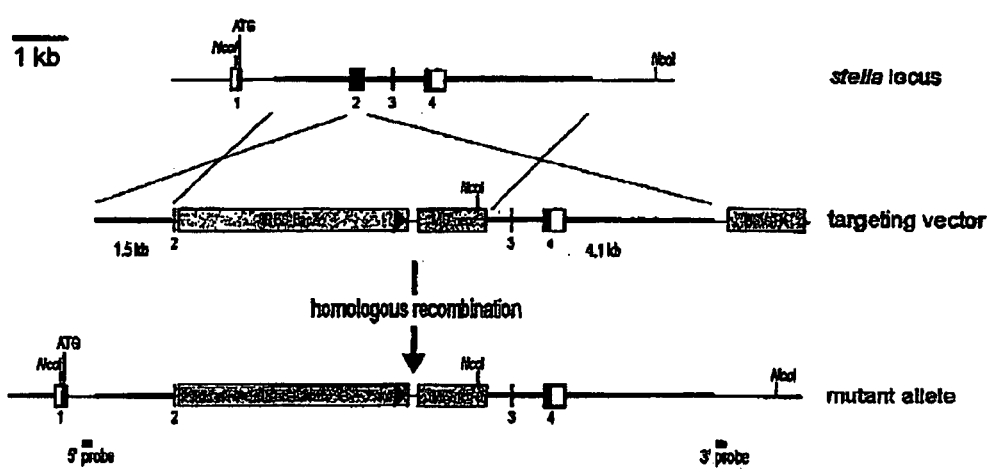
b
c
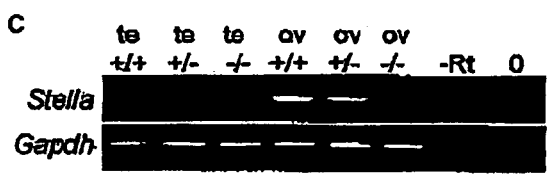

SEQUENCE LISTING

```
<160> NUMBER OF SEQ ID NOS: 64

<210> SEQ ID NO 1
<211> LENGTH: 617
<212> TYPE: DNA
<213> ORGANISM: Mus musculus

<400> SEQUENCE: 1
gccgcagaaa gggcagaccc gcagcgcgct ccatcctttg ccctccagtg ctgcctttgc      60
tccgcaccat gaaccacact tctcaagcct tcatcaccgc tgccagtgga ggacagcccc     120
caaactacga aagaatcaag gaagaatatg aggtggctga gatgggggca ccgcacggat     180
cggcttctgt cagaactact gtgatcaaca tgcccagaga ggtgtcggtg cctgaccatg     240
tggtctggtc cctgttcaat acactcttca tgaacttctg ctgcctgggc ttcatagcct     300
atgcctactc cgtgaagtct agggatcgga agatggtggg tgatgtgact ggagcccagg     360
cctacgcctc cactgctaag tgcctgaaca tcagcacctt ggtcctcagc atcctgatgg     420
ttgttatcac cattgttagt gtcatcatca ttgttcttaa cgctcaaaac cttcacactt     480
aatagaggat tccgacttcc ggtcctgaag tgcttcaccc tccgcagctg cgtccctcct     540
tgcccctccc tacacgcagg tgtaacactc atttatctat ccacagtgga ttcaataaag     600
tgcacttgat aaccacc                                                   617

<210> SEQ ID NO 2
<211> LENGTH: 137
<212> TYPE: PRT
<213> ORGANISM: Mus musculus

<400> SEQUENCE: 2

Met Asn His Thr Ser Gln Ala Phe Ile Thr Ala Ala Ser Gly Gly Gln
1               5                   10                  15

Pro Pro Asn Tyr Glu Arg Ile Lys Glu Glu Tyr Glu Val Ala Glu Met
            20                  25                  30

Gly Ala Pro His Gly Ser Ala Ser Val Arg Thr Thr Val Ile Asn Met
        35                  40                  45

Pro Arg Glu Val Ser Val Pro Asp His Val Val Trp Ser Leu Phe Asn
    50                  55                  60

Thr Leu Phe Met Asn Phe Cys Cys Leu Gly Phe Ile Ala Tyr Ala Tyr
65                  70                  75                  80

Ser Val Lys Ser Arg Asp Arg Lys Met Val Gly Asp Val Thr Gly Ala
                85                  90                  95

Gln Ala Tyr Ala Ser Thr Ala Lys Cys Leu Asn Ile Ser Thr Leu Val
            100                 105                 110
```

```
Leu Ser Ile Leu Met Val Val Ile Thr Ile Val Ser Val Ile Ile
        115                 120                 125
Val Leu Asn Ala Gln Asn Leu His Thr
    130                 135

<210> SEQ ID NO 3
<211> LENGTH: 823
<212> TYPE: DNA
<213> ORGANISM: Mus musculus

<400> SEQUENCE: 3
ggatcacaga ctgactgcta attgggtctt ggttttaggt cttttcaaag actaagcaat    60
cttgttccga gctagctttt gaggcttctg cccatcgcat cgccatggag gaaccatcag   120
agaaagtcga cccaatgaag gaccctgaaa ctcctcagaa gaaagatgaa gaggacgctt   180
tggatgatac agacgtccta caaccagaaa cactagtaaa ggtcatgaaa agctaaccc    240
taaccccgg tgtcaagcgg tccgcacgcc ggcgcagtct acggaaccgc attgcagccg   300
tacctgtgga gaacaagagt gaaaaaatcc ggagggaagt tcaaagcgcc tttcccaaga   360
gaagggtccg cactttgttg tcggtgctga agaccctat agcaaagatg agaagacttg   420
ttcggattga gcagagacaa aaaaggctcg aaggaaatga gtttgaacgg gacagtgagc   480
cattcagatg tctctgcact ttctgccatt atcaaagatg ggatccctct gagaatgcga   540
aaatcgggaa gaattaggag cttacattgt acgctgccct ggctgtcgac gatgccgcac   600
agcagatgtg aaagctattt tttgtttaag attaaacttt ttctggtgct gggaaatctt   660
aacttgttaa cctttaaatt gtagatagga tgcacaacga tccagattta tgtgaagttt   720
agaagcctca agctgtgagg cccagggctg aggaataaag taaatagaat ttggagtatg   780
tacgttctaa tttccagaaa tttgtaataa aagcattttt gtt                    823

<210> SEQ ID NO 4
<211> LENGTH: 150
<212> TYPE: PRT
<213> ORGANISM: Mus musculus

<400> SEQUENCE: 4

Met Glu Glu Pro Ser Glu Lys Val Asp Pro Met Lys Asp Pro Glu Thr
1               5                  10                  15
Pro Gln Lys Lys Asp Glu Glu Asp Ala Leu Asp Asp Thr Asp Val Leu
            20                  25                  30
Gln Pro Glu Thr Leu Val Lys Val Met Lys Lys Leu Thr Leu Asn Pro
        35                  40                  45
Gly Val Lys Arg Ser Ala Arg Arg Arg Ser Leu Arg Asn Arg Ile Ala
    50                  55                  60
Ala Val Pro Val Glu Asn Lys Ser Glu Lys Ile Arg Arg Glu Val Gln
65                  70                  75                  80
Ser Ala Phe Pro Lys Arg Arg Val Arg Thr Leu Leu Ser Val Leu Lys
                85                  90                  95
Asp Pro Ile Ala Lys Met Arg Arg Leu Val Arg Ile Glu Gln Arg Gln
            100                 105                 110
Lys Arg Leu Glu Gly Asn Glu Phe Glu Arg Asp Ser Glu Pro Phe Arg
        115                 120                 125
Cys Leu Cys Thr Phe Cys His Tyr Gln Arg Trp Asp Pro Ser Glu Asn
    130                 135                 140
Ala Lys Ile Gly Lys Asn
```

<210> SEQ ID NO 5
<211> LENGTH: 4925
<212> TYPE: DNA
<213> ORGANISM: Rattus sp

<400> SEQUENCE: 5

```
cccccccccc cccccccccc cctcccccc ccccacctc cgacgtatga tggctcctag      60
acgcaacacg aagcggactc cccgcatcat tcacgtagac ccgccttctg ctttccctgt    120
cggggttttg ggaagcccgg cggccctctc ttctcacctt gctccactag cacgcggctg    180
ttttcactga gcccagcact ggctaagtgg agcaccagga gtttcaggct atccttcaga    240
gggcaaggtg tagtccatgg tgggctacag gagaccctct ctctccgtga gtacagagag    300
gcaaacccaa gccagacagg ggtgatgatt aggaacatac cttcgtcggg gagaaaatac    360
cggttcatat aggaataaga ggaaccagga ggtagttaag gctgtggtgt ctggttgcgg    420
ggttttttgac tctcaacaac cacgttcaga acgtgctgag tttttatgat ggtgtagaat    480
ttccttatca gcaattggtc tccgcggtgt ttcttttct ttttaatttt tttaagtata    540
atttggtgtt tgaagcaact gtacttggac tagaactccc tgtgtaatcc agaatggaat    600
cccaaatcct aggattaaag gttttagtgg gctgcagtgt tgggtggggg ttgttttgat    660
tacgttgtag cccaggctgg gctcaatctc aatcctcctg cctctgcctt ctaaacgcta    720
ggattaaaag tgctgcgcca tgatcctgct gtagctttat ttttatttat ttatttattt    780
attttggctc ttttttttttg gagctgggga ccgaaccgag ggccttgtgc ttcctaggca    840
agcgctctac cactgagcta aatccccaac cccagtgtag ctttattttt aagaacagga    900
gtcttgtttc tcaaaacagt ttctctgtag ccctggttgt cctggaactc cgtaaaccag    960
gctggttttgg gactctgcct ttaaaacact gggactaaag gcggtaccac ctccgtgggc   1020
tacaccggaa tcttttaagc ttcatttgaa ccggggcttt ttctttttct cacccacttt   1080
ctggaagcga ttttcctgct aaattccat tcctggtaaa tgactctgag gggaaatagg    1140
aacccagaat agattgagcc ggggctacc tgggaccccg cactcccac ccccagccg     1200
ctgttgaagc tctttgcctg agggggcctcc gggtttgata cctcctagca ctccgggctg   1260
agggcgtggc tcgggaggag ccattccttt ggagaggaaa acaactgctg gccttgaatc   1320
tgccctaata cctgacagtt acatgggacc tccttatttc cacaggattc tttagtcttt   1380
gtttgggaga ttttcaaatc ttgagactgc tcaacccttc ctggcctaac actcacaagg   1440
ccaggctaga cccaaattct gtcaaccct tctgtgtcca aaacggtggg tggctagctg    1500
gctcacccttt ggtgtcactt tgctttaaca ttcggaaaag ttgtggtaag ttcctgtat    1560
aaaataggac catctactgg gtgtggtccc atgtaaagca aggttggttt cccaaaatac    1620
cctgtttaca tagatgtccg gaagcattgg agcaggtcaa ttagatttag gtggaaacag   1680
cctgttttg gaaagctttc cagggcggaa aatgaaccca gaggcactat tgggcaagcc    1740
ctccggctaa gcaacacaat tggctgcagg ggtctctgga agaggtgtga gacaagagag   1800
aatatgcagg tttcaggacc tctgaactag agttaggctg ctgtaacatt gtaacattgc   1860
tgtaagcaga acagcccatg gtaagaagct cagtggatct ctacaaacac taggatatct   1920
gctcagggtt tatgaccagg ccctgtgcat atggtttgct tcttgttggc ccctctcttg   1980
aagagggggtg attatctgtt acccacttcc ttgtttctct ggggtattac cttgcaaaat    2040
gcaaaatgat atacttcact aatgtctcca tcttctgttt cagaaatcct acaaccagaa    2100
```

```
acactagtaa aggtcatgaa aaagctaacc ctgaacccca gtgccaagcc gacaaaatat    2160
catcgtcgtc aaagggttcg tctccaggtt aagagccagc ctgtggagaa cagaagtgaa    2220
agaatcatga gggaagttca aagcgccttt cccaggagaa gggtccgcac tctgttgtcc    2280
gtgctgaaag accccatagc aaggatgaga agatttgttc gggtgagttg cgtttgtggg    2340
cggggcatag atctaagagc aactctagcc tcaggaatgg cacctaggtt aaacagggaa    2400
tgtagacaag gatagtgact acctgtgatt cccagctcaa gaaaacaagc tccaaggcta    2460
tcctctactg cgcagtctga agctggccag agctatatgc aaattgataa gtcagtataa    2520
catttatttt tggattttca gactccctcc ccatagtcca aactggccct ccagttcagt    2580
ccacggtcct gcttcttccc cggtgctagg cttttgagtg ataaggctga cttagactgg    2640
atctcagagc tgaagtggac ctgttagtct ttgtagacca ggctggggtg gtttctgctt    2700
tctcagcgcc tagctcacat agtaggcatt ttaactttgt cttaatagta atttgagtaa    2760
ttttgttttt ctcttgaaga ttgagcagag acaaagacag cttgaaggaa atgaggtaaa    2820
tgcatatgga tgggtagggt gtctatggat gggtagggtg tcttgttttt actgtttcct    2880
tagacaagga gtgtgtatgt ggagagttac cttctcaaca cagggaatct ggttattaaa    2940
gcagtacttt aaaataaat aaaataaata aaataaaaat aaagcagtag aaggggattt    3000
acatttcttt tgagttgcaa tatcctgatt aacatttttc tttcagagac gagatgagcc    3060
attcagatgt ctctgcactt tctgccatta tcagagatgg gatccttctg agaatgctaa    3120
aatcgggcag aaccagaaga attagggcag tttgaattgt acaccgtcct tgccgttaac    3180
ggtgccatgc agcagatgtg aaagctgttt ttttgtttaa gattaaactt ttcttggtgc    3240
tggggaaatc tcttctaatt gctaaccttt aaattatata ggatgtgtga catttggatt    3300
catgggaatg acagatttac ccaagaattg agcatgagtc aaagcctggt agtttgattt    3360
agaaggtaat tggaataaat ctttttattt tagattttct agtttgcaga gaaatttgta    3420
ataaaggcaa atttgttatc tttaataaat acagaacaga ttagaatgag ccattggaga    3480
tgggggactg gttttttaca ggtgcatgtg tgggtgtgtg atgttcagag ttcaatgtgt    3540
gctaccctgt atttctgctt gaggcaaggt ctccatgagg cctagctggt ctaactcctg    3600
gtcctgcctt ttgttttccc ctgagttttg acaccatagg cttgtcggca agatctggaa    3660
gaggcttgat gtttgtgttt gtgctgtgta ataaacaatt ggttgacata ttcctaaagt    3720
gtggcactgt attgacctgt ctgtctcatg aggaagttaa tgaccggagc ataattgtat    3780
gctttatttc ctgagagaag tgtcaggaaa ggaggagtta ggaagaaagc cccaggctgg    3840
ggttaagagc actggctgct tttccagagg tcctgagttc aattcccagc aatcacctgg    3900
tggctcccga acatctgtaa caggatccaa tgccctcttt tggtgtgtct aagaactccc    3960
taggcatgca gaggattttt gttttgtgtt ttttttttt tttttttttt ttcgtttttt    4020
tcagagctgg ggaaccgaac ccagggcctt gcgcttgcta agcaagcgct ctaccactga    4080
gctaaatccc caaccctac aatgccttt ttctacctgc ttttgaatta tcaataaaag    4140
actggggcaa agaaaggct ggagtgaatg agagagaaca tgtgaagagt aaatgagaga    4200
gagcatgagg gaatgaatga gagagtgaat gtgagaacga atgtgagagc gagtgagaga    4260
acatgagaag aacacgttaa gagtgagtga agagagaatg tgaggtgtgt atgaagattg    4320
tgtgtggggt tggggattta gctcagtggt agagtgcttg cctaggaagc acaaggccct    4380
gggttcggtc cccagctcca aaaaaagac ccaaaaaaaa aaaaaaaaa aaagattgtg    4440
```

```
tgtgtgtgtg aaaggagagt gcatgtggtg tgtgtgagat atgtgcaagg tgtgtatcaa    4500
gagtgtgtgt gagagtgaaa gggtaatgaa cagaggtgtg catgagcgtg ggagtttgag    4560
aaaagaaaac agcaataaaa aaaaaagcag agtgcacgag agaatgcaga gtgtgtgcaa    4620
cctcaagctg agacagagac agagagaaag agagagagag agagagactt taagccttga    4680
aattacctgt cagtttgtac ccaaatagta gtctgtgtat atttattttg agccttccag    4740
atccctgctt ccagtggaga actctgattc tatgttgagg ctggaccctg gcaatagtgg    4800
gcttcttgaa aaatagtcaa aggaaacagt gctacaccat ggacttaagc ctttagactc    4860
agttctggct tcaagagcag ctgtcagaaa ataagtgatg aactacttgc agtcgaactc    4920
gaatc                                                                4925

<210> SEQ ID NO 6
<211> LENGTH: 1444
<212> TYPE: DNA
<213> ORGANISM: Rattus sp

<400> SEQUENCE: 6
ccaggattca gacgagctag gcctcatgca tggagacctt gcctcaagca gaaataaaca      60
gggtagcaca cattgaactc tgaacatcac gagtgtgcac acacccacac atgcatctgt     120
aaaaaacgag tccccatctc caatggctcg ttctaatctg ttctgtgtat ttattaaaga     180
taacaaattt gcctctatta caaatttctc tgcaaactag aaaatctaaa ataaaagatc     240
tattccaatt accttctaaa tcaaactacc gggctttgac tcatgctcaa ttcttgggta     300
aatctgtcat tcccatgaat ccaaatgtca cacatcctat ataatttaaa ggttagcaag     360
tagagatttc cccagcacca agaaaagttt aatcttaaac aaaaaaacag ctttcacatc     420
tgctgcatgg caccgttaac ggcaaggaca gtgtatgatt caaactgccc taattcttct     480
ggttctgccc aattttagca ttctcagaag gatcccatct ctgataatgg cagaaagtac     540
agagacatct gaatggctca actcttctct catttccttc aagctgtctt tgtctctgct     600
caatccgaac aaatcttctc atccttgcta tggggtcttt cagcaccgac aacagtgtgc     660
ggacccttct cttgggaaag gcgctttgaa ctcccctcat gattctttca cttctgttct     720
ccacaggctg gctcttaatc tggagacgaa cccctttgacg aagatgatat tttggccgat     780
tgagatagaa tatcaaaaca acatttaaca tttaaataac ttaacgatat acacacccttt    840 ttttttttcca cctccccaca cagacaaaaa acaaccctat tttttctttta caaccccgcc    900 taagcaagcg aagcattagt aactgaccaa tcatagaaag gaaacaccac cagaccacat     960
caaataaaat aaaatcaccg cccaacccca cccctataaa aaacccgccg accacaccac    1020
atatactccc cccccccgc accatcacta catcacccctc tccaccccatt cccacccctccc  1080 cccccaacat taaccccacc ccatcacgga aaccccccaac accaacaaat aaattagaca   1140
catcgcatta cataaattga cacaagaccc accccaaaag agcagcaaag attagagcca    1200
catcctcggc ccaacacaat acactcaacc tgcatagtat ctatctccac cccaacctag    1260
aaacaaaaat ctaatcagca ccaggcaccc aagtatcacg cacactcaaa aacataccca    1320
ccaattaaac acgccccacc cacccaacaa cccacccgcc tgacaacaca cttcggaact    1380
accctcaaca tcaccaaaag caatcgcaag ttacgatgac tccaaccacc tcactctctc    1440
attg                                                                 1444

<210> SEQ ID NO 7
<211> LENGTH: 7656
```

```
<212> TYPE: DNA
<213> ORGANISM: Rattus sp
<220> FEATURE:
<221> NAME/KEY: misc_feature
<222> LOCATION: (7471)..(7471)
<223> OTHER INFORMATION: "n" is an unknown nucleotide
<220> FEATURE:
<221> NAME/KEY: misc_feature
<222> LOCATION: (7554)..(7554)
<223> OTHER INFORMATION: "n" is an unknown nucleotide
<220> FEATURE:
<221> NAME/KEY: misc_feature
<222> LOCATION: (7608)..(7608)
<223> OTHER INFORMATION: "n" is an unknown nucleotide

<400> SEQUENCE: 7
ctgcaagtag ttcatcattt acagatcaaa agaaagaaga ataaaaaaac aaggtgtcat      60
gatccctcca aaagagtgga acacttcaac tgccagatcc aagatactga aatgggtagc     120
atgctggaga agaattcaa aagttaggta gagaatctgg ttgagcagag cacttgcttt      180
tcttccagag gatctgagtt caagtcccag gacctatatc acagttttct gtaactctag     240
ctccagaggg tctgacactt ctgttcactg tgggcacctg cattcacaga caaacataaa     300
gtagttcatc accctttca cagaaaaccc acagcatgtg aggaaatccg ggtctctgcg      360
caatgccccc acagcagaag gggggagctg gagagatggt tcatctgtta gcccatttat     420
tgctcttgaa gagaacccag ggtcatccat agcacccata gcagctcaca accatctcca     480
gttccaggag atccaatgcc ctgttgtgac ctcaggtacc aggcatacac aatgaacctg     540
cacacataca aaagtccata gagccatagt taccattgtg agctctgaga accaaatccg     600
tgttctctgc aagagcgaca tgcacgctga aaccaggca cctttcccac tgcctcttga      660
gacaagatct cactatgtag ttcacactgg cttccgactt gccaccatcc tcctgcctct     720
gcctataaag aatgctagga ttatataggt acaaaatcac acctggctgt taaggttttt     780
ctggctgttt ttttttcac ccccatgaat gattttgaaa atagttgagc tgtttacatt      840
aataaaacaa aatcagatgg agactatatg tcattattca tgaatcaaat gactagtaac     900
aatactgagt tattttata gcttttctat ttttgtttta aattttattt tttccttttt      960 tttttttc ttttagtttt tgctttgttt tgttttgagc aggctctcac tgtgtagtcc      1020
tgggtgatct ggaacttact aggtaaacaa ggatagcctt aaactcaaga aatttgcttg    1080
cctctgtctc cagagtgctg cagttaaagt tgtacaccgc catgtttagg tgtttttatt    1140
agtgtgtgtg tatgtctgtg tgtctgtgtg tgtgtgtg ttccccggag gccatgtagg     1200
cgcatgcttg aaccagaacc agaggaagtg tgtttacagt taccctggga ggccagaaga    1260
gggcaggaga tgccctggaa ctggaatttc tggtagtggt taactgccta aagtgctggg    1320
acctaacact cttaacttct gagccatggc tctagtcctg gggtccccc tccttctttt     1380 tatgactatg cagactatac aaatttattt tatatattaa ggtctacggg agcagtttgc    1440
cctggcagag agtatatata tctcatggtg acatacatat ctcatggtga cacacatatc    1500
tcatggtgac acacatatct catggtgaca tacatatctc atggtgacat acatatcatc    1560
tcatggtgac acaattgagc attgagagca gctacagacc gattagatca gacttattaa    1620
attcttgcca gtatgtggt gacgcaggcc tgcaatgcca gtaactttgg agactgagcc      1680
aagcagatca cctgagccta gagactcaag gccaccctgg acaacataga gatatcctgt    1740
ttcaaaatga aacaagctaa gttctttgta catgcagcc tctctattga ctgtggcagg     1800
gcagctgaca gtgttctcac ctagtcacag atgttctttc tagagggaac agacccgatg    1860
```

```
aatacaaaca ttttagctc aagtaaaagt ctatactatg aaggaactac ttcttcaaac    1920
atcataacat ttaaaatgag agattttaca aaccttttt taaagattta tttgtttatg    1980
ataagtacac tgtcactgtc ttcagacaca ccagaattgg gcatcagatc tcattacaga   2040
tggttgtgag ccaccatgtg gttgttggga attgaactca ggacctctgg aaggacagtc   2100
agcactcttt ttttttttt ttttttctt tcattttttc ggagctgggg accgaaccca     2160
gggccttgtg cttgctaggc aagcgctcta ccactgagct aaatcccaa cccccagcca    2220 gtgctcttaa ctgctgagcc atcttcccag ccccaacatc aattttggt ctagatgttt    2280 taccctggtg ctgccatgcc atctcgatgg cccttgtggc aggggtgccg gtaaggcagc   2340
ccctagggca tgagttaggg agagcaaaac ctgacccaga acctgactgc catgaagtga   2400
tggagatgcc gtttgagtac atggggtttt tggtggttg ttgttttgtt ttgtttttg    2460 tttttgttga cttgacacat gctacagtca tctgagagtg aaacttaatt gagaaaatgc   2520
ctctgtattt tctccggccc cctaagttgc ttttgatgag tgtatttta tcacagcaat   2580 agaaactcta actaagatag attggtatta gaagtagaat attgctgtaa cagaccctaa   2640
ccatgttctc ttggggagga ttgtgggaag actttggaac ttggaacttg gaacaggaga   2700
agccattggg tacttagagc ttaatgggct gttctgtgga gcttggaaag gtgctggaga   2760
aatgcggatg atacttgtaa agtttgagag caccctcaaag atgttcagga cagtgtgtgc   2820
aatacatttg agttaagaat ctatggtgtc tggtcagctg gagctgaaga ttcagctgtg   2880
attaataaga ccactaaagt aaaacttttg ctttactggt acaatcagtg ctggttagct   2940
aagggttgac agatgagcag tgactaataa gagactggca tcagaaactg atccagagag   3000
agccaaggct gcatctcaaa ctggcagcca aatttgatca catgtaagaa tctccctcat   3060
gggggttggg gatttagctc agtggtagag cgcttgccta ggaagcacaa ggtcctgggt   3120
tcggtcccca gctccgaaaa aaaagaaca aaaaaaaaa aaaaaagaa tctccctcat      3180 gttacaggct ttggtggcat gagagcttta gggttgaagg atcatggaga gcagccgagg   3240
ctccgcacca tgtggcgggg cagaggtaca gcccagttac cacagagaca ccagcatatt   3300
tggaggtgcc aggatcatgg ataattgcct aagacaggag gctggcctga ctttgtagga   3360
caagctccat gatctgtttg gcaggactgg agaaacagag ctgtaaggga aaatgaggac   3420
acagctgttc caagatatga ttggagagaa gggtttcatt gcagatctga ggaagaggac   3480
agccagagag gcatctggaa gggtccagat tgaactgggt catgagagga gagagggcta   3540
agaggaccaa aagagcctgt gaccaaatta tcagggttat agaaaaaca gatgcttggg    3600 aaagagaagg gggagcccct gagctggaga gatttaaagt aggggcagg atgagaagtg    3660 gctggggcag gatgagaagt gctgaggagc caaaggcact cagtgaacct agaggccaag   3720
gatacatttt gacatgctaa taggcatttt agtcatttgt cctgcatttc tttaggacag    3780
gccaagctgc ctgggtcatt gtgagtccca gataattctc ttgaaataaa atgttttta    3840 aagagaggag gggaaggttg gggagggtgg tctgaagtta agagactttg gagtattaag   3900
acattggata ttttagagaa aattttgaac ttttaagaag actgaccttt taaagtgttt   3960
gaatttttaa agaccaggat acatcagggt gtagggacac atgaccctgt ctcgcccccc   4020
ccccccaaaa ttataatttt tttaaaaaga ctgtgggagc tgggtggtgg tataggcctt   4080
taatcctagc acccaggagg cagaagcagg cagatctctg agtttgagac cagcctgatc   4140
tatagcatga tttccaggac aatcaaggct acacagtgaa gcctatctta gaaaaaaaaa   4200
gattgtagtt ttagtttgcg atgtatttta tattgaggtg ctgacattaa tatgaaatct   4260
```

```
ttgtgagtgg gcaagaaaat aaagactaaa gctgaatact gatgccactt gtgtgtcaga      4320
ttgacaaggg gttttggaat tttttttattt ttttattttt ttttaggaat atatcaacca      4380
attgtttatt acacagcatg aacaaacaca aaaatcaagc cttttccaga tcttgctgac      4440
aagcctatgg tgtcaaaact cggaaacgag aggcaggacc aggagttaaa agaccagcga      4500
ggcctcatga gaccttgtc tcaagcagaa ataaacaggg ttggtagcac acacgaactc       4560
tgaacatcac gagtgtgcac atcccacac atgcacctgt aaaaacaaat cccccatctc       4620
caatgtctcg ttctaatctg ttcttgtatt tattaaagat aacaaatttg cctttattac      4680
aaatttctct gcaaactaga aaatctgaaa gatctattcc aattaccttc taaatcaaac      4740
taccaggctt tgactcatgc tcaattcttg ggtaaatttg tcattcgcat gaatccaaat      4800
gtcacacatc ctatataatt taaaggttaa caagtagaag agatgtccct agcaccaaga      4860
aaagtttaat cttaacagaa aacagctttc acatctgctg tgtggcacct ttaacggcaa      4920
ggacggcgta caattcgaac tgccctaatt cttctggttc tgcccgattt tagcattctc      4980
agacggatcc catctctgat aatggcagaa agtgcagaga catctaaatg gctcatctct      5040
gttctcattt ccttcaagct gtctttgtct ctgctcaatc cgaacaaatc ttctcatcct      5100
tgctacaggt tctttcagca ccgacgacaa caatgtgtgg acccttctct tgggaaaggc      5160
gctttgaact tccctcatga ttctttcact tctgttctcc acaggctggt tctgaacccg      5220
gtgacgaagg ctgtgatgac gatgatattt tggccacttg gcactggggt tcagggttag      5280 cttttttcatg acctttacta gtgtttctgg ttgtaggggtt tctgaatcat tggggtgagt     5340
cctctccacc tttcctctga gatctatcat ctgagtttct ggatacacaa ctgggtcaac      5400
tttctgtgat ggctcgtcca tggcggtggg cagaagcctc aaaagccagc tccgaacaaa      5460
attgctagct aatctttgga aagacctaga ctttggcccc aactagcaga ctgaagtgct      5520
ggaatttttt tttttttttt tttttttttt tgtaatcaac ttgaaaacac aattgagaaa      5580
atgcttccat aaggttaaat ccttgtgcca ccatgcctgg acctaagctt tcatggcca       5640 ctattcctcg aggtctggat cagaagcttg tgtatttcat ttccggattg tcgttcactc      5700
cagattaaaa gtccaaatga aagcaatagc catgtaataa tgcctagata taactcttcc      5760
ttgttcagca gcaaatgcat aagcaataag cttagctggg tgggatcttc caaagctact      5820
ctgctctttt tcttcttgga cataggattc agcaacattc tacttcttga tgcccctta      5880 ttctttgaac catacatttt tacttttcct ttcgtagcct cttcctttc atcaaaagat      5940 tcttcataag agtgaaattt ggggttagag agatggttca gtggttaata gcactgactg      6000
ctcttccaga ggtcctgaat tcaattccta gcaaccacat ggtagctcat aaccatctgt      6060
aataggatct gatgccctct tttggtgtgt ctgaagaaga cagcaacagt actcaacata      6120
cataaaataa aaataaatca acatacataa aataaaaata attttaaaa aaaaaggtg       6180 aaatttaacc acacaacaga atttatgcca ggcttgtttg agacttttgt caaagcaatt      6240
aatctaaatc tcttcacctt agcctcaggt agactctctg acaatggca aaaagcagcc       6300 acattcttca tcaaaatatt acaagaacgg tctctcagcc atactaaa attcttctct        6360 gaaacttcta gagccaggct tccacagttc aaaccacctt cagcaacaaa gtcttctata      6420
ttcctacgat gatagcccctt taagccccac ttaaagcatt tcactgaatt ccaaatctaa     6480
agtctccaaa tctatattct tccaaataaa agcatggtca gacctaccta tcacagcaat      6540
atcccagtcc ctggtaccaa cctctgtctt agttaggggtt tccattgttg tgaagagaca     6600
```

```
ccatgaccaa agaaacactt ttttttttt taatatttat tttatgtcta tgagtacact      6660
gttgctgtct tcagacacac cagaagaggg catcagatct cattacaaat ggctgtgagc      6720
cactacgtag ttgctgggaa ttgaactcag gacctctgga agagcagcca gtgctcttaa      6780
ccgccgagcc attttctcca gtcccaaaga aacacttata aaggacaatg ttttttttgg      6840
ttttttttaa aggtttattt attttatgta tatgagtaca ctgtagctgt cttcagatac      6900
accagaagag ggcatcagat cttactatag atggttgtga accaccatgt ggttgctggg      6960
gattgaactc aggacctctg gaagagcagt cagtgctctt aaccccttag ccatctctcc      7020
agttctaaag gacaatgttt aatcggggct ggctcacagg ttcagaggtt cagtccatta      7080
tcattgagac aggagcgtgg cagcatccag gcaggtgtgg ggctgaagga gctgaaagtt      7140
ctacctcttg atccaaaggc agaccaaaaa aaagactggc ttacgggctt accataagca      7200
gctaagagga aggtctcaaa gcccacccta cagtggcatg ttctccaaca aggccacatc      7260
tcctaatagt gccactcccc gggccatgca tattcaagtc gccacaccca ctgagccatc      7320
tctccaacct gctccagacc atctcccctg cttttaccta agctcattag gcagcaatat      7380
gcctcttatt gtttgagctc agcatcctgt ttttcaaaag gctgcttgtc atcacagtgg      7440
tttgttccac aactctccca gtttctttgt naaaacacca atgcctagag agatgctctt      7500
ctgtacatat cgcatgtgca gaagaaaggg tgccagatcc tttcatgtgg accntgtcat      7560
gtctttaccc acgtagtcgt ctgctctgac tcttctcgag atgctganaa ctgattgagc      7620
gtaggatgct ctgggtatgt gcatgggaca attttg                                7656

<210> SEQ ID NO 8
<211> LENGTH: 2161
<212> TYPE: DNA
<213> ORGANISM: Rattus sp
<220> FEATURE:
<221> NAME/KEY: misc_feature
<222> LOCATION: (2115)..(2115)
<223> OTHER INFORMATION: "n" is an unknown nucleotide
<220> FEATURE:
<221> NAME/KEY: misc_feature
<222> LOCATION: (2142)..(2142)
<223> OTHER INFORMATION: "n" is an unknown nucleotide
<220> FEATURE:
<221> NAME/KEY: misc_feature
<222> LOCATION: (2143)..(2143)
<223> OTHER INFORMATION: "n" is an unknown nucleotide
<220> FEATURE:
<221> NAME/KEY: misc_feature
<222> LOCATION: (2146)..(2146)
<223> OTHER INFORMATION: "n" is an unknown nucleotide

<400> SEQUENCE: 8
cgaaggacgg taaggagaga agaggggaga ggatcaggac tgaggggaga tatgcactga       60
acgggggagt tagtaacgag gaaaagatag ggagaaaagt gggagaaaaa aggccgggga      120
gggggagggc atggaaagaa aggcgggggg gggagataac atgcggggga agtaagaggg      180 gggggtaag gagggtacag gtagcacagg tgggggaag agaggggagg gggggaatgg       240
gaaaggtgag ggtgggtggg ggagttttcg gcgaaagggg ccggagtgtg gattatcgcg      300
tggaccagaa cgggggaagg gccacatttg ggtgggcggg aacagaaagg aaatcttttt      360
aaatcggttg ggtcgcaggg tgggtggaca ttgagaaaaa aatcatcaaa gcccctaagg      420
agcatttgtt tcggagttat acgtatggat attttattat atgggacgag agataaagaa      480
tacttcttaa gtaatccctt taaaataat gtcaggctgg agaaatggtt tcatgggtaa      540
gcaagtgtga gagatgagcg cagaccccca ggacctgtgt agacttaatg cagaggtgga      600
```

-continued

```
tgcacgcctg taatctcagc atgcctacag ccagatagga gatggggaca gagaagtgtg    660
ggggccaact agcctggtgt ctacagcctg gtgtcaacag cagcctccta cctcaaacaa    720
ggtggaaggt aagggctgat acctgagatc gttgtctgac ctccacacac attgtgctta    780
tactttacac acatactcac actcacacat acatacacat atatacctgg tctccattag    840
gcttctattg ctgtgataaa gattacgacc gaggtctttc caaagactaa gcagttttgt    900
ttgcagctag ttttttgaggc ttctgcccac caccatggag gagccattag agaaatcgac    960
ccagttgtgg acccagaaac tcctcagacg aaagatgaaa aggacgcatc cgctgattca   1020
gaagtcgtaa gccagaaaca ctagtaaagg tcatgaaaac gctagccctg aaccccagtg   1080
ccaagcggtc agcacatcgt cgcagcctcc gtctccggat tcagagaaga cctgtggaga   1140
acagaagtga aagaatttcg agggaagttc aaagcgcttt acccaagaga agggtccgca   1200
cgttgttgtc ggtgctgaga gatcctatag caaggatgag aagacttgtt gggattgagc   1260
agagacaaca caggctggaa ggaaatgagt agaaacggaa gagtgtgcca ttcagactca   1320
ctgtgctttc tgccattatc agagacggga tccgtctgag aacgctaaaa tcggaagca   1380
ttaggacagc ttagattgta cactgtcctt gtgttaatga tgccatgcag cagacctgaa   1440
agctggcttt tgcttttttaa gattaacctt ttcctggtgc tggggactct tctaacttgt   1500
taacctttaa attatatagg gtgcgtgatg tttggattca tgtgaatgac ttaaatttac   1560
ccaaagaatt gagaaggagt caaagcattc tgtgaatttt tgaagcctca agcccggggc   1620
cgagaaacaa tgttaataga atttggaata gtttggttta aaggtaatt gggatagatc   1680
tctgaattttt ctagtttgca aaacaaaaa caaaaaaaa gactaaaaaa acaactgggg   1740
aggagtaagg ttatttcagc ctccatgtct tgatcccagt ccatcatgaa aggaagtcag   1800
gacaggaact caagtcagga ccgtggaagt aggtagcatc tgaagcagag acttctggga   1860
tgaaagcgct gcttcctgac tcgctcccca caaattggtc cctgagcctt cttgtccacc   1920
ctcggacccc ttgcctaggg ttggcaccac ccacaatggg ctgagccttc ccatgtcaat   1980
cactaattaa gaaaatgctg tacagcgttg cctacaaacc agtcttaagg aggcgttttc   2040
tccattgtgg ctctctcttc tctgataact ctagcttgtg tcaaattgac aaccaaccag   2100
ccagcacaca aacanttaaa aagatagaaa taatgttagt gnntcncatc gagcaagagt   2160
c                                                                  2161
```

<210> SEQ ID NO 9
<211> LENGTH: 21688
<212> TYPE: DNA
<213> ORGANISM: Rattus sp

<400> SEQUENCE: 9

```
tttatgattt taaaagttta attctggact ggagaaatgg ctcagtggtt aagagtagta     60
actgctcttc cagaggtcct gagttcaagt cccagcaacc catggtggc tcacaaccat    120
ctgtaatgag atctgatgcc ctcttctggt gtgtgaagac agctacagtg tattcacata    180
cataaaataa ataagtaagt ctttaaaaaa aaagtttaat tgtgtgtgtg tgtgtgtgtg    240
tgtgtgtgtg taagcttgca ataagagga caactttgag gagctgatac tcttgttcta    300
ctgtgtaggg accaacagtt gaactcaggt tgtccggctt atgcaacaag ctttttttact    360
tgtcttcgcc agcccaccag tcctgtgtaa agctgcatac agctcacgtt gtaacatgct    420
tgtctagtac ttgcaggaca taaactagca agcacttggg tgaaaacggg aggatcagaa    480
```

```
gttcaatact atccttggct acttaacaag tttaaggcta taggaatagg gatataggaa    540
accctaagaa agtaaaattt atttactgtg ctttaggtga tcaaacctac agctttgcat    600
gtgatagaca aatgttctac cactaagcta catcctcagt gttctttatt atctattttt    660
ttaataaatc ttttttttta aacattgttg tgagccaccg tgtggttgct gagaattgaa    720
ctcgggacct ctggaaaagc agtcaaggaa gccagagtgg ccggaactcc tgaaaatgga    780
gtaacaacag gttgttgtga gggtaattga actcaggtcc tatgcaagag caacaagagg    840
tcttagccct ttattatttt ttaatatcta attattttt tattttttta tttttattta    900
tttattatat ataagtacac tgtagctgtc ttcagataca ccagaagagg gcatcagatc    960
tctttacaga tggttgtgag ccaccatgtg gttgctggga attgaactca tgacctctgg   1020
aagagcagtc gggtgctctt aaccactgag ccatctctcc agccctaatt atttatttta   1080
tgtatgtgag tacactgtag ttgtcttaag acaccagaga agagggcatc gggtatcaga   1140
tcaccattac agatggttgt gagccaccat gtggttgctg gaattgaac tcaggacctc    1200 tgaagagcag tcagcattct aacgactga gccatctctc cagcccaacc ccccctcca    1260 ttttttttaa taccaaaaag gagcttcctg caagagaaca tggccatata catccacccc   1320
tctttctttg aggttttgat agtgctgctg ctcctgctgc ttggaaaaga aaatcctcta   1380
ggactaagct aaaagagcca gatggatgga attgcggttg ccatggcaac accatctgag   1440
gatactgagc ctgctgtctc tcccagttat gttgacattt ggtgtggttt ccatgcttga   1500
acactgaagt gtctgtccac ctatgaaaga gaggccgttc ccagaggtct aatttatct    1560 gctccatcag tagcatttgg actgcttaca tttatgtctg acaaccatt ggccaggagg    1620 tagaaggagga tggaggaagg cccagacctg gctgggtact atcggatcta gtgaagctgt   1680
atagaatctg tctggggttt atttactccc aactggagca gaggcaggtg ctcaggaagg   1740
cagtaatgag atcgaccttta ccacaggaaa taaagtgact actgtggata ccatctggga   1800
tggatcaccg ctgagccact ccaccctcag aacaaagcta ccatatcgtt aaagtgtcct   1860
gagctcaggg gaaggcccct gctgcctgtg agtagagcca ggtaacctta caagccccta   1920
tctacacttc atcttaaggc attctgttac atacaaagaa ttctactctt taatgagcag   1980
actttaaaaa aaatgagcca acttacactt tcagaagttt gatccttgat tgcacatgcc   2040
tgagacagat ggccagtctc aaggacaggc ctcccacact gaagttagtc ttcagcagta   2100
tgtcatgtca cctaggcaac caataagagc tcacctaaga aatttccact ttacctggta   2160
aagagcgtat cttccctccc tttctctcca attagcatcc tcacttccag acttccctac   2220
taccgacttt aaaagatcaa agccaggcac gatagcacag gctgaggtcg gaaggcagaa   2280
gccagaaaga tctatgtgat tcccaggcta cttagcacca cacagttgag accctgtcta   2340
acaaatggag gtgggaggca tggcagtaac ctgaacctac aaatttatca aaatttcaat   2400
taagaacatt ttgttttgtt tttgaggcag aatctcacta cgtagagtgg cttacaccc   2460 agttccaatt aagaacattt taagggctgg agagatggct cagctgttaa gagcactggc   2520
cactcttccc aaggtcctga gtacaattcc cagcaaccac atgatggctc acaaccatct   2580
gtaatgaggc ctgatgccct cttctcttgt gtctgaagac agctacagtg tcctcattta   2640
aataaaaaaa catttaaat agaaaatcca acagggaggc tgatgagaaa cgacataacc   2700
tttgtccagg agtgtggtta aggggaatgg aaccatagta gagtccattt ctttttctct   2760
tttgagccaa aaaagtttta tttattcatg tcttccattt gaagtactcc ttggtggcat   2820
cctaagcctg agattctttg ccatacgtag ttcttaacca ctacccaact gcaaccaact   2880
```

```
gttttctgtg gcatccctct tgatgacttt tacacagggg ttggggatttt agctcagtgg    2940
tagagcgctt gcctaggaag cacaaggccc tgggttcggt ccccagctcc ggaaaaaaaa    3000
aagattttta cacgggcaca cccactccac tagtttctca tgatcaagta taatcagatt    3060
gatctggtgc tcggcacaaa gtgcctcctc cagctcgaca cacacgagct catcacagtc    3120
ggattcgagc acacagatgg gtttggcact tgtctaaggc ttcaggagct ttgtgtttgc    3180
caacgtgctg ggctatcgtg gatgagggcg tcttcagca cctcttgtag agcagtgttg    3240
acatccacac ctccagtggc agtgccctgc tccgctctcg gaagctgagg tggaatagca    3300
agtcagtttc ttctctcatt tcccagacac cattatggat gcctcagtgt cagctgttca    3360
tttgtcactt acttttcaca attgtgttat tattattgat agattattgt ctctgtcact    3420
agctaccgag gcagggtctc acaggactta tccaattgtt tctgcctccc tcgagctaag    3480
cctgaaggca tatatgaatc atctcaccaa gcagcatcag cttttaagag tttctgaacg    3540
tcaacacgtt aacactgggg ccatattatg tacgatgtaa ttaatcctcg agcaactggc    3600
cacacagccc taaagaaaaa aaaatccag aaccaaacaa accaaaaaca ggcacgaatg    3660
gtggcacaca ccttcaatct ttacacttgg aaggtggatc caggaggagt aggaattcga    3720
agccggccta gagtaccagt agttgaaggc cagcatctgt ctcaaagcaa caacgataa    3780
taaagtactt gtttcagctg ggaggtggtg gtacattgtg gagggagagg cagaccttga    3840
acactgggtt caaggccagc ctggtctaga gatcagatcc ccaaaacagc cagggataga    3900
cagagaagcc ctgtctcaaa cgtgaggct ggagagatgg cttagtggtt aagagcactg    3960
actgctcttc tagagatcct gagttcaatt cccagcagct atatggtggc tcacaaccat    4020
ctgtaatggg atctgatgcc ctcttctgtg tgtctgaaga cagctacagt gtacttatat    4080
acatgaaata aatctaaaaa taataataac gtgcacaatg ttctgcctgc ctatatgcct    4140
gcaagccatc cctccaaccc aataaataaa tattaaaaaa aaaaaaagc acaaaaccaa    4200
accaaaagta aaataaataa acaacttttta ttcctaccaa gagaagacac atttccttga    4260
gaactaagga caacatgttt atggttagaa cacagaagag aataagagca cagctcagct    4320
ggaagaaaca aagtgttctg gggacaagga gccttcttcc ctgcccccat aacagtggcc    4380
agattgaacc tctggtacga cagtcaagtt ggtgctgagt tcaagttgga aagtcacact    4440
ttctaaatca ggatcaaagc aagctggagg ctccctcact cagctcacaa gtcctgtgaa    4500
atcaggaaaa aaatatcagt tagacactga gttcccaggc agccaaaaac caaagatttc    4560
ccaccaccaa agacaaggta tcttggattt ccaagggaac agaatgagaa cttatatctc    4620
tgactggcat ttaaatccta cagccatccc ctctccagca catcctttct ccagggaatg    4680
gtcccagcac ccatgtcagg cactcaccca agtagtcatc catcagagag ccaatagcaa    4740
actgcgagag gaaagggaga aaggatggtg aggtgggggcc ccaccccatt ccgagccttc    4800
tgtcatctat tccctgctca tggacacaga gcacagagcc cccaacaact gtggatggca    4860
agaggtcaac agcgcagatg gggaaagagc ttgctccaac cctgatgacc tgacctccac    4920
ccccaaaatc cacagcagca tgcgatgacc tgaaggcggt ctaaatgtca cactgtggcg    4980
agtgtgtatg cccacacatc cacataaata tgttctacaa aagaaacgag aaacccacag    5040
ctgtcagctg tgaatgatga ctttggatta tttataatcc tactcccag gaggctaagg    5100
caggccagtc aagcaagaga ctcacaatgt cattcttgtc tacacgtgtc cctacaatct    5160
tcaagcgtat ctcatcgtcc tgctgaatta caatgtcctg tggaaggag agagcagggt    5220
```

```
catcaagcag actcaggcct ggtcctcatc cctctcacca actcctcctc attcgctcac   5280
ctcatccatg gtcttgtaac aagggggtt cgaatttgga tcaaactcca tctctgaagg    5340
gatggactag aaggaaattg acacaaaggt tagcatttca aatagctgca tcaaaggatg   5400
agagtcaggg gctggtttct cctcctcggc ctcaccccac acgcccagac tcacgtgtcg   5460
agagatgaag caggacatgg gcccaatttc tgtgaaaagt ccaacctaga aggaaaatga   5520
ccgtgcttca aacgctctga agcatcttta cctgatttct aggcacatta ttcatgtttc   5580
ttaacagttt aaattgtagc atttgtttta atttctctct gtgtaatctt tcatttcttt   5640
acatttttgt tcttcattat ttttatgtgt aagaatattc tgacctcaca tgtgcctgtg   5700
caccatgtac ctgcagtgcc catggaagcc aggagagggt attgggaccc tgcagaatta   5760
ggagttacag attattgtga gccattggct gggtgctggg agtcaaaccc aggtcttata   5820
gaaccagtag gtgctctaaa ccactgagct atagacccct tagcctttaa gaaacttaat   5880
ttctgaggct agagagatag ctcagtggtt aagagcactg actgctcttc catgggtcct   5940
gagttcaatt cccagcaacc acatggtggc tcacaaccat ctgtaatgag atctgatgcc   6000
ctcttctggt gtgtctgaag agagctcagg aggagtgtgt ataataaata aatcaggggc   6060
tagagagatg gctcagcggt taagagcact gattgctctt ccaatgatca tgagttcaat   6120
tctcagcaat cacatagtgg ctcataatca tctgtaatgg gatctgatgc cctcttctga   6180
tgtgtctgaa gacaacagtg tactcatata aataaaaata aacaaacaaa ccttaaaaaa   6240
aaaaaaaaaa aaaagaaaag aaaacccaaa actaagataa aataaaataa atcttgacaa   6300
ccacaaaagg cttaaggcaa ctaataagtg gactgggaat tgaactctca ccttaggaaa   6360
taccccgtaa cctttctttt tttttttttt tttttcttc ttttttttcg gagctgagga   6420
ccgaacccag gaccttgcac ttcctaggca agcgctctac cactgagcca aatccccaac   6480
cccataacct ttctataaat aatactctta ccttgttgac ctgagtgacc acagcatcca   6540
ccacttcccc tttaaagggc cggaaaacaa tagctttgta tttcactgga taaagaacaa   6600
aacctcggcc cggctggatc acaccagcac caatattgtc gatggtagtg acagcaatca   6660
caaagccata tctgcaggaa agatgaaaaa agacagctac tgtatgtgaa gagcctctaa   6720
aaagccacca gcaatagtct gcgtgtgatg gaacctctgc tcgaacagct cgatgaccaa   6780
gaagagacag aactcagatt agcacctgaa atattaaatg gtgctctcac aattgtacag   6840
taaatgccca agaaggcaca gatatgctga catacaccta ttctctcagt accaggactt   6900
gccaggtcag tggtgagaca ggtctttcga aaaccacaaa tcagacagaa aattgtgacg   6960
aaaaccttta atcccagcac tcagtggcag gcagttctct gaattagagg ccagcttggt   7020
ccacatagtg aggccatctc gaaacccaaa acatttgcat aataacggtc tgatctcgca   7080
taagcgaaga aaatttggtt tagcaacctt ttagaaggcc caaaataggc aaaaactggc   7140
tgcttcggat gcctggagtg gtgaaagagt tcctcagagt aagtaacaag ccctgactga   7200
aggagtgaag tagaggttac agagtagcgt tattgtgcct gcattcagca gacgacactg   7260
tgaatcagac acttacttcc cagtgcaggt cccctccacc tcggtgaaca gcttctgctt   7320
caccgtgttg agcaagttgg gaccaaagta gcgtgggtgc agtaggatct cgtgctccag   7380
ggaaatctgc agagaaagga agatgaagac tccgccagcc acactgagaa caggaggcga   7440
cccgtcggcc ctccaggctc ctcctgtccc tgccctcacc gctacccgc gtccagctca    7500 catgataaaa catcttctgc agaagcttgg accgcagagg ccagaactcc ccaggaaggg   7560
acctcgccgg aagcactagc agaagtccca ccaagtctcc gcagtcgctt ccgcagattt   7620
```

```
gagtcttaac gccatgggcg gggaaacgtg aagccccgcc cctcaggcct tcccatcagc    7680
gctcatcagc acagccagga ttacacagaa aaacccggtc tcgaaaaacc ttaaaaaaaa    7740
aaaaaaaaaa aaaaaaaaaa ggttaagagg tctggcttgt cgccacatgc ctttaaaccc    7800
agccgtggca gacagatctc taaattcaag gctaagccac atctacaaag tgagttccag    7860
gataaccaag actgtgtata caaaccctat aaaaaatttt gttttggggg ttggggattt    7920
ggctcagagg tagagcgctt gcctagcaac cgcaaggccc tgggttcggt ccccagctcc    7980
gaaaaagaga aaaaaaaatt gttttttaaa ttttatttta ggggctgaag aattagctca    8040
gtccttaaga gcacttgcca gcccccacag gatagctcac aatcttatct gtaactacag    8100
ttcagagaga actgacaccc tcttctggct tcattcagca ctgcatgcta gtggtacaca    8160
gacataatgc aggcagaaca ccgatgcttg taaaataaaa ataaagatga ggtagttggg    8220
gagattgctc aacagttaaa atcaatggtt gctcctccga aggatccagg tttgattcct    8280
agaacaaaca tggtaactca actagctata tttcaatcct aggggatcca gtgccatctg    8340
gggcctccat ggacacttct cccttgtggt gaacaggcat agatacagcc agaacattca    8400
tacatataaa ataaaaataa aggtttttac acataaaata aaaataaagc tctcgaagag    8460
gacctgagtt caattactaa cactgcaccc gaggtctcac aactccagct cgaaggggat    8520
ctgaaacttt ctcattgcct caggaggtac cagcacttgt gggcttgtac tcacatacag    8580
ataacagaca tcattgagta cacctaatta agaagaagtc acttggaagt gtggcacacg    8640
ccttaaatcc caatattcag gaacaaaagg caggtgggtc ttcaagttca aggccaacct    8700
ggtctacagc atgagttcca gaacagccag ggatacatta aaatgaagg tgtcggggtt    8760 ggggatttag ctcagcggta gagcgcttgc ctagcaagtg caaggccctg ggttcggtcc    8820
ccagctccgg aaaaaaaaaa tgaaagtgtc ttgttaaaca aaacaaaaag acaacaagca    8880
aaaagattac ttatgtgggc acgcactggg cttactttct tttctatttg agggacggtt    8940
ttattatgtg accatggatg acctgagatt tgctttgtag agtaagcttg ccctgaactt    9000 tttttttcccc tggagctgag gacctaaccc agggtggtgg gtttataggc aagcgctcta    9060
ccactgagct aaatccccaa ccccccaccc ttcacttttta ggataccaag cagactcctt    9120
ggtctaggaa caacctcagc ctcgggactt ttttttttt tacactaggt tccgctcctg    9180
ttagactaga ctcttccacc cctcagtaca ttatactact aggacactag gacaaaccat    9240
agcaaatctg tcacagcacc agtgacagcc ctaagcctga ctccatcttt tcttttcttt    9300
ttttaaatat tatttatttt atgtatatga gtacactgtc attgttctca gacacaccag    9360
aagagggcat cggatcccat tacagatggt tgtgagccac catgtggttg ctgggaattg    9420
aactcaggac ctctgggaga gcagtcagtg ctcttaaccg ctgagccatc tctccagccc    9480
ccactgaaga cttttgatct ggttaccatc tgaccccaat ctcttgcaaa gcctcccttt    9540
cctccttcga agaaactctt acgtcttta tgtccttggc ccatgacttt gtattaaatc    9600
agcaacaatg acaagacctg tatgtctctc cctagctcag aagacagatc cttgttcctt    9660
gttaatgttt tgattttctg gtctgtccgt ggggacagtc tgatagttct aagactgata    9720
gctttgaggg attctaaact cacaacaggg ctattgttac cgatgggcac aatacaaggc    9780
tgccattgct ttggagtggg accattatct tgacagaaag aattaccata aaccctagct    9840
gtgattgctc cggagtccca tgctaatgaa acactgccca cggccttcag gaaacttctc    9900
acagagtgct gcctcttgga atgactgtgt gaactctcta ctgtccacct gcagcagcca    9960
```

```
taccgaaata cagtctaata acctctcaac ttctgcattc ttagtcttgg tgaactcttt    10020
cgcctccaat gtcatgacct ttcaaagtca cctcacatag cagtctgcag cgagaacagg    10080
taattcaggg gctggggatt tagctcagtg gtagagcgct tacctaggaa gcgcaaggcc    10140
ctgggttcgg tccccagctc cggaaaaaaa aaagaaccaa aaaaaaaaa aaaagagaga    10200 acagtaattt cagctaagac tggtgacaca agtgtaattt taatacttag gaggttgagg    10260
cgagcgcatc tggagtttgg attaacctgg actccatagt gaatattggg ctagcttagg    10320
ctacataagc aagcctctct ctctctctgt ctgtgtctct gtctctatct ctgtctctgt    10380
ctctcaacca caaagagag aacgaaaaa aggaagaaat taagagaaag aaaaacaaaa    10440
gaaatttctc taagcaaagc atatttattt atttatttat tgttttttcaa gacagtgttt    10500 gtctatgtag cattggctgt cctagaacaa tcgttgtagg ccaagctggc cttgaactca    10560
taggcctgcc tttgccttcc aaatactgga attgaagcct tgtggcagca ctgcccagcg    10620
acacctggaa ttttttaaaa tttatttatt tatttattta tttatttatt tatttattta    10680
tttatacact ccagatatta ttcccctctt ggtccatccc ccaactgttc cacatgtcat    10740
accttccccc acccccagt ctccacaagg atgtctccaa cccacccacc ctctctaatt    10800
tttattgtac attcctcttt ctttcttttt ttttttttt tttttgggt ctttttttcc    10860 ggagctgggg accgaaccca gggccttgcg cttcctaggt aagcgctcta ccactgagct    10920
aagtccccag cccctacatt cctctttcta acttctttgg cacagcatct tggagggtgc    10980
aaatcaagag acagcttttc ttttcttttg tgatgccaac tttcaagcat ttacattttg    11040
ggttgggttg ggttgtgatt tttttttgt cttcgaaatc tgcattttt ttctttcctt    11100 ttttttttt tttcagagct ggggacctaa cccaggggct tgcgcttgct aggcaagcgc    11160
taaaacactg agctaaatcc ccaactccta aatctgtatt tttatttgta caactgtat    11220 ttctttttct atatcctta actctggagt tttcatttct tccctcctgc ccccataact    11280
atagtcacag ttaaactgtg ttatcaggaa attcaggaaa ggtgccttga tgaacagatc    11340
aggacaggag ctctgaccag tagtcactgt cttcctcttc cttagaataa gtaaaaatga    11400
aaccaaccaa actttcttct ctttcttttct ttcttttttt ttttttttt tttgacgtgt    11460 ctcctgtgct ttgtcagtag catgaattc atttttttt tttttttttg gtttaaaaaa    11520
ggcaacctca aaacccaaac ctctttattg tcagggaaaa gggaactgca atgacttgaa    11580
tttgaggatg tgggtactgc ctcactcaca cacattctca gactgtgtga tgccctgcac    11640
acctgtagaa cagttacatg tatgtgcacc tgtatttgtg cctattagaa caggacctgc    11700
agggaagtct acctaacccg aaactcccca gtggaacagg cagggtgggt ggagggctgg    11760
gacagacaag gactcggcgc acacatacag taccacataa aacagtacag tgaaggtggg    11820
ctcaagaccc aggcagcttc cttcttttca gtaacagggc ccaggctgcc tttcacagca    11880 caacccccaca gctgaaccca ggtctctctt caaaaccagc catctcactc agcagcgcca    11940
aaggaaaagt agatgtagcc tccctgcaga gaaacagctt ttcttgttgt tttaaataa    12000 gtaagtaaat ccaccatccc tctgctccaa gatggctgat gttacacttt tctaccagat    12060
tggtgcctgc ttagctcact aacagtgctg cctccgccgg ctgtggcaga gtttccagtg    12120
tggtgttttc aagcctcacc cactcatcct ctcattccca acattcagt gccctcctca    12180 cttaggggtt ttcgaaatgt ttaaattttg tattactta aatatatatt tgttttattt    12240
tcatgcgtct gtgtgtatgc ttgtgagttt cacacatgct gtgtgtgcac aggaatctat    12300
gaaagccaga acagggcatc agatctacag gaagaaacca agtgtccaaa aagggaagaa    12360
```

```
acgagatcca tctgcctctg tggtgctgga attgaaggtg tacatcacta caaccaccgg    12420
ggatgggtat gtatgtatat atatatatat atatatatgt gtgtgtgtgt gtgtgtgtgt    12480
gtgtgtgtgt gtgtaagggt gtcagacctt ctggaactgg agttagacag ttgtgagctg    12540
ccatgtgggt gctgggaatg aaccctggcc ctctagaaga acagctgatg ctcttaactg    12600
ctgagccatc tctccggccc cttattttt atttgtgtga gagagtggag gtcaggggac    12660
aaactgagag acttggttct ctccttctgc catgtgaatg ccagggattg aatgcaggtt    12720
gttagccttg gcagtgagtg cttttccccgc agggccatct tgtcagctct ttgattacat    12780
tgtaaaccct ggcactgtgt tatttgctgg gaaatgtttt tagttgtggg atgactcagc    12840
tttagcacat gcctttaatc cgagagcttt ctgcttgtat attgtaagca ggattaaata    12900
aagtcaaatc ttaggtcaag agatggagca agcaaagagt tgacaggaaa tgaacataga    12960
attattgaga aaaacatat aggggttggg gatttggctc agtggtagag cgcttaccta    13020
ggaagcgcaa ggtcctgggt tcggtcccca gcaccggaaa aaaaaaaaa aaacatatag    13080 agtaaggggg agtcgggttt aaactgtaca gaagtctcca tgtcttattt ataatgtaag    13140
caggtctgca aaagcctgcc gttgtgtcct gttgcctttc ttctggcagt gaagaggatc    13200
agttttgaag gcaggcagaa taggtgcgga gagatggctt ggcagttaag agtatatgct    13260
gctcttgcag aggacctgca tgcaactgcc agcacccaca cagtggttcg tagctacctg    13320
taacttcgtt ccatgggatc cgatgccttc ttctgacctc tgagagcacc gaccatgcac    13380
atagtgcatg aacatacatg cgggtgaaag actcacataa agtaaagtga atacatctaa    13440
ttaaaataaa gaccacttta tgggctggag agatggctca gcggttaaga gcactgactg    13500
ctcttcctga ggttctgagt taaattccca gcaacagatg gtggctcaca accatctgta    13560
atgagatgtg atccctctt cctggtgtgt gtgaagacag ctcccagtgt actcaataca    13620
cccctcccct ccctgaatgg gaaaaaaaaa aaaaagcct ggggttgggg atttggctca    13680
gtggtaaaaa aaataccttat gaagcacaag gtcctgggtt cggtcccagc cccgaaaaa    13740 aaaaaagaaa aaaaaaaag accactttac acgtaaaaaa taaagatgg gcagattagg    13800 ccctgtacta aacaggattc tttagaggaa ctgaaatgag tgtgtgtgtg tgtgtattca    13860 tttttttaa agatttattt attttatgta tatgaagaca ctgttgctat cttcagacac    13920
accagaagag ggcatcagat cgccttaaag atggctgtga gccatcatgt gggtactggg    13980
atttgaactc aggacctctg gaaaagcagc ccgtgtgta ctcatttat atatgaaata    14040 tatacacaca tacacacgtg tgtgttagat tggcttcctt gatggtccag gtaattcatc    14100
aatgagaatc agtagttact cagtctacaa agctgaatgt cgcgacaatt ctgatctggc    14160
actttagacc tagaggactc ctggagagtc tacatgggaa tcctggacat ctggagatcc    14220
tacacaaaat ccctgccatt cccaccaagg gcagctgtga atggcgtgg ggaaacattc    14280 cttaagctaa gcctgaagac ctaaatccaa tccctggaac ccgtgtggta gatggagaga    14340
actgacttct gtttcatctg acctccactg gtgtagccgc acatacatgc atgcaaaaca    14400
gtcgtgataa ataaatctaa aaaaagttag agcacctgtc aatagataag tataacttaa    14460
aagtgaaacg aagcctatgc ttttaaatcg taaggactgg gaggcagtca ggcacatatc    14520
caggttccag accagcctga tgtatgtaat gagttccaga ccaattaggg ctatatcatg    14580
agaccatgtc tcaaaaccaa aaaacaaaag aaaagaagaa aaaagaagaa catcaagtca    14640
agcatgataa atcacataat cctataatcc taataatggg gaggctgaag cagaatggcc    14700
```

```
atgcctttga gcttagcctg ggcaggacaa ccaactgggc tacacaggaa tacataatac    14760
actgccatta gaaaaaaaag catggctgac ttcgtcactg ctagttgggg cttgggttta    14820
ggtcttttca aacactaagc aatttggttc ggagctagtt tttgagccct ctgcccaccg    14880
ccatggagga gccaccagag aaagtcgacc cagttgtagt cccagaagct cctcaaatga    14940
aagatgacga ggacgcgtcc gctgattcag aagtcctaca accagaaaca ctagtaaagg    15000
tcatgaaaac gctaaccctg aaccccagtg ccgaacggtc agcacgtcat cacagcctca    15060
gtgtccggat tcagggcagg cctgtggaga acagatgtga aggaatcttg agggaagttc    15120
aaagcctttc ccaagagaag ggtccacaca ttgttggtgg tgctgagaga tgccggagca    15180
aggatgagaa gatttgttgg gattgagcag agacaacaaa ggcttgaagg aaatgagtag    15240
gaagggaaga gtgagccact cagacgtctc tgtgcttcct gccatcgtca gagatggaat    15300
ccgtctaaga aagctaaaat ccggaagaat taggacagtc ggtttatgta cactatcctt    15360
gctgctcatg atgccatgca gcagacctga aaactggttt ttgtttttta aagataaaac    15420
ttttcctggt gctggggaac acgtcttgtt aacctttcaa ctatgtagga agtgtgacgg    15480
ttgaattcat gtgaaggact taaatttacc caaagtatgg agaatgagtt aaagcattct    15540
gtgaacttta gaagcctcaa gctgggggct gagaaacact gtaactagaa tttggggtag    15600
tttgctttag aaggtaattg gaataggcct ttggattttc tagtttgcag aaatgtgtaa    15660
taaaggcaat tttgttatct ttaacaaaca cacagaacag attagaatga gccattggag    15720 atgggggggtt gttttttacag gagcacgtgt gggtgcgcac actcctgatg tccagagttc    15780
```

```
aatgtgtgtt gctaaccctg tttatttctg ctccaggcag ggtctccatg agcctagcca    15840
gtctctcagc tcgtggtcct gcctcccttg ttgcccaagt tttgacgcca caggcttgac    15900
agcaagatct agaaaatgct tgtcttgatt ttgtgtttgt tcatgctgtg taataaaaag    15960
aacaattggt tgatgtattc ctaaatttaa aaaaaaaaaa aaaagcacca ggtgatggtg    16020
gctcacccct ttaatcccaa cgctcagaag gcagagacgg gtggatctct gaattcatgg    16080
ccagccaggg ctacacagca aaaccctgtc ttgagaaaag agacttgtgg ggttggggat    16140
ttggctcagt ggtagagcgc ttgctaccct gggttcggtc cccagctccg aaaaaaagaa    16200
tagaaaaaaa aagaaaaaag aaaaaagaga ctcgtaagca agcaaagctt ggtagtctaa    16260
agaaatgaga aatccttaga gctaccttag agctagaaaa ggcaggacat ttcaggcaga    16320
gagctggtac ggcaagccca aaggctcagg gcccggttta taccatgtaa ggttatcctg    16380
aggggctgga gaagaaatgc acagcaacac taacacgtca tactgtctgg ccaagtatca    16440
actaccatgg ctttatagat cctgctcttg aggaaagggg tagatcaagg ggtaatcaag    16500
gatagattac ccctttggca ataggacgga gggtggctag atccctccaa cagtgtgagt    16560
aggtccaaga gtatgaatca tctatggctc taataaaca ctgctaggct aatttaccat    16620
tgagctacat cccaaatatc aaaagttgtt ttgggagagg ggatgcatgg gagacaggtt    16680
ctaatgtgaa tcttactgtc ctggaactcc ctccatagac cgtgctggct ttgaacttac    16740
agagttctca caggagactt aactgccttt gtctccaaag tgctgggatc aaaggcgtgc    16800
accaccacat ccagccttat tttaattaat tataatcaat tattaattaa ttataatcat    16860 aatttttaatt agttttgatc atatttatcg atgtattatg gaagtggggc cttgcatgtc    16920
attcttgttg gtaaaggtca ggagataaaa atactacttg gtaaataaga aaacccaagt    16980
taagaaagat ggagaaaaaa aaacaatatt atagttaaaa aaaaaaaaac ttggtctttt    17040
aaaaataaaa tacaggggggc tggggattta gctcagtggt agagcgctta cctaggaagc    17100
```

```
acaaggccct gggttcggtc cccagctctg aaaaaaagaa ccaaaaaaaa aaaaagaaaa   17160
aagaaaatac agggctggag agatgctcag cggctaagag cactgactgc tcttccagag   17220
gtcctgagtt caattcccag caaccacatg gtggctcaca accatttgta atgggatctg   17280
atgccctctt ctggtgtgtc tgaagacagc tacagtgtac atgaatacat aaataaattc   17340
tttaaaaaaa tgaaaaataa aatacatgtc atatgattta tcaaaaaaaa aatactactt   17400
ggacagggtt ggagatttag ctcagtggcc gagcacttgc ctagcaagtg caagaccctg   17460
ggttcggtcc tcagctctga aaaaaaaaat tactacttgg agaagtaggt tctcccctcc   17520
cactcaagtt gtagaaatcc aacttagatg tcaggaggca agctctcgta ccaacggaac   17580
ttaagatttt ggttttgaa gtcttgtaga gaccaggcta tcctgaaatc aagatttaat   17640
ttacccagct ccaaaaaaaa aaaaaaaaga tttaatttaa agtagctgtt ccatgccttt   17700
gatcccagca ctctggacaa gagaggcaga tgcaggttgg tgtgtgagtt tgagatcagt   17760
ctcaaagctt ggtccacatg gaaagttcta gaacagccaa ggcttcatga gatcgtgtct   17820
caaaacagca aagacagtga cgatgacgtg atgatgatga gcaacataga ctcaagcgtg   17880
ctaggccaaa acaccactag atctgctccc tagcccctga caagtaattt gctaacaaca   17940
tgcatagtgg ttattcttcc aatttctcct tctccttctc cttctcctcc ttctccttct   18000
tcttctgttt atttatttat gtgagtacac tgtagctgtc ctcagacaca ccagaagagg   18060
gcatcggatc tcattacaga tggctgtgag ccaccatgtg gttgctggga tttgaactca   18120
ggacctctgg aagagcagtc agtgctctta gctgctgagc gtctctccag ccccccaattt   18180 cttcttttaa aattacataa tcaccactag gtggggtggc acatgcaggc agatctctgt   18240
gggtttgagg tctgcctggt cttggtattg agttccaggt cagccagagc tatattctga   18300
gaccctgtct caaaaagaca gaaatagaag taaaaaagaa aacggaaaat taaaaaacac   18360
agggaggcgg tggtgacaca cttttgatccc agtactgcat ttgggaggca gaggcaggtg   18420
gatctctttg tattacaggc cagcctggtc tacagagaat tccaggacat caagtactat   18480
gcagagaaac tctgtctcaa aacaccaata aacaaacaaa caaacaaaca agtaaaaata   18540
aataaataaa aattaaaaaa ggaaaagaaa aacgaaaaag aaagaagaga ataaaattgt   18600
attgcttatc atgaatgctc caactcgtgt gtttaggtca gaagcaaact aacaggaatc   18660
cttttttctc tggtatcaaa ctcgtgggtc ttaggaatcg aactcacata cttcggttgg   18720
gcggcaagcg atttaccccg ctgatccatg acacaggccc tctttaattt ctaaagccct   18780
acatgcgggt ctggacttta ttcacggtgg gtgggtcttc ttcctgtcag tttccgtccg   18840
cagatgtccc cgcccaccag gaaggatctt tcgggctctc gtcggcaccc gtccaccctg   18900
tctccacgtg acacaaacag acagggcact tccgcttccc gtccactctc ctcactcagt   18960
gtctacaccc cccgtccccg ggtccccgc ccggtgagtt agcgagcgcc gggagggcgg   19020
cgtcgcgggc ggagtcgccc cgggctgacc cttgccgcct tccttcttct caccgcaggt   19080
ccccgcggta gcggaggcgg gcgccatggc ggagctgacg gctctggaga gcctcatcga   19140
gatgggcttt cccaggggac gcgcgtaagg gaacctcccc tctagcctgt ggtgggaggc   19200
cgcgggcctg ccgggcctca ctgtcaccat ggctggtggg cgctattcac ggtgtttctg   19260
ccctcaggga gaaggctctg gccctcacag ggaaccaggg catcgaggct gcgatggact   19320
ggtgagcgac tggcacgggt ggaggaagtt tgggggcctc tgggaaaggc ggcctcaagg   19380 ctaacccccct gccaacttc tctgcccagg cttatggagc atgaagacga ccccgatgtg   19440
```

```
gacgagcctc tagagactcc tctcagccat atcctgggac gagaacccac gccctcagag   19500
caagttggtc ctgaaggtcc tgactgggag acatcttgtg attctagcta tctagtgagg   19560
gcctgaggaa accagaatgc tttcactata aataataata ctagttgctt gtttgtagga   19620
tctgggtctg ctgctggaga aagcaaaccc gttttgactg aagaggagag gcaagaacag   19680
actaagaggt aactgtgcaa gttcagtgtg tgtgtgtgtg tgtgtgtgtg tgtgtgtgtg   19740
tgtgtgtgtg tgtgtgtgtg tgtgtgtttt gtttggagcc tgcctcactc ctgtccaggc   19800
tgaactctgg atcctgctgc ctcagcctcc agagtgctgg gattacaggt cttcaccact   19860
gtgccctgta ttatttttg agacagggtc tagctgtgta cctcaggctg gcctggaacc   19920
taggctaaat gcaacgccac attcttctga gtgttgtgat caccatagct agcccattaa   19980
cacactttcc caagggtcat gggtcatctt cctttcttct caaatacaaa cacaagtcag   20040
gacagacctg gccttttccag ttagtggatg ttggggagt caccaggaaa catctcatac   20100
agcacaagac tgtctaaact cctgcgtggc tgcagactcc cctgaaatcc caattctctg   20160 gccctactt tgcaagtgca gggactgtag gtattcacca ccgtgcctgg ctcttgtctg   20220 cccttttaa aaaacaaaa acaaaaagg ccccatgcat aatgtatgtg ctctaacact   20280
gagctacctt ttttttttc ttttggtttt ggttttgttt tttcaagcc agagtctgtc   20340 tctatcccg ctgtccttaa actggctcta tagacctggc tggactgaaa ctcaagaaat   20400
ccacctgcct ctgccttctg agcactgagg ggtgcactgt caccacctag cttgcccttt   20460
ttatgttact gtcttggctt tgttttttttt tttcttttt ttttcttttt tttggagctg   20520
gggaccgaac ccagggcctt gtgcttgcta ggtaagcgct ctaccatcga gctaaacccc   20580
caaccgggct ttgttttctt ttatctgtct tggaacacaa tcctttaatc tgttaattct   20640
ctgtttaaac tcaccttccc actccatatc cagcttcagc ttttcttct ctgcaaaaca   20700 gaatgttgga acttgtggcg cagaagcagc gggaacgtga agaaagagag gagcgagaag   20760
ctttagaacg agagaagcag cggaggagac aagggcaaga gctgtcagct gcacgacaga   20820
aactacagga agatgagata cgccgggctg ctgaggagcg caggagggag aaggctgaag   20880
agctagctgc caggtctgaa gactcatagg tcactaacgg aggaagaaat gaagacttgc   20940
cttgcccatg tctgacctat cttcctcctg tctctcttct agacaaaggg ggcgagagaa   21000
aattgaaagg gacaaagcag agagagccca gaaggtgggt gatgaggaag tctgtgggta   21060
taatggagta ggggggtgcg gggccgtggg ggcgtgcggg cgaggggggg gggggggggc   21120
gcgggtgggc gggggacgga gaggggcgg ggcaggcggg gggggggcgc ggaggtgcgg   21180
ggggtttctc acgggtggag gaggggcggg ggggggggga ggtggggtcg tgcggttgat   21240
ggtgcggcgg ggttgataga cgccgtgcga gttggcggcg ggggcgggc ggtggagggg   21300 cggctgagac gggggggcagg gggtgcgttg ggggtggagg gcagtggggc gggtgcggtt   21360 gctggcgcg cggcgcgga acggtagccg gggcgcgcgg gagcgcgcgc gcgcgctcgc   21420 gaggggggtgc ggccggagag gggtgcggag gtccggtgag ctgactgacg atgcccggta   21480
gctgctggcg cgtgggcgac gcgtcatgcc gtggcgcggg tggggcgggc gcggtgcatg   21540
cgcgagcgtc ctcggtctgg cgaccgtagc gcgctctctg tcggggccgc ggaccggcgg   21600
tgagggtcgg gggcggggggt gcgtggtggc tggaaggcga gtggtgtcgg gtagagggcg   21660 gcgataggg gcgcgcgtga tgtgatat                                      21688
```

<210> SEQ ID NO 10
<211> LENGTH: 17

```
<212> TYPE: PRT
<213> ORGANISM: Mus musculus

<400> SEQUENCE: 10

Ala Ser Gly Gly Gln Pro Pro Asn Tyr Glu Arg Ile Lys Glu Tyr
1               5                   10                  15
Glu

<210> SEQ ID NO 11
<211> LENGTH: 16
<212> TYPE: PRT
<213> ORGANISM: Mus musculus

<400> SEQUENCE: 11

Arg Asp Arg Lys Met Val Gly Asp Val Thr Gly Ala Gln Ala Tyr Ala
1               5                   10                  15

<210> SEQ ID NO 12
<211> LENGTH: 16
<212> TYPE: PRT
<213> ORGANISM: Mus musculus

<400> SEQUENCE: 12

Met Glu Glu Pro Ser Glu Lys Val Asp Pro Met Lys Asp Pro Glu Thr
1               5                   10                  15

<210> SEQ ID NO 13
<211> LENGTH: 17
<212> TYPE: PRT
<213> ORGANISM: Mus musculus

<400> SEQUENCE: 13

Cys His Tyr Gln Arg Trp Asp Pro Ser Glu Asn Ala Lys Ile Gly Lys
1               5                   10                  15
Asn

<210> SEQ ID NO 14
<211> LENGTH: 60
<212> TYPE: DNA
<213> ORGANISM: Artificial
<220> FEATURE:
<223> OTHER INFORMATION: AL1 PCR Primer
<220> FEATURE:
<221> NAME/KEY: misc_feature
<222> LOCATION: (1)..(60)
<223> OTHER INFORMATION: AL1 Primer

<400> SEQUENCE: 14
attggatcca ggccgctctg gacaaaatat gaatcctttt tttttttttt tttttttttt      60

<210> SEQ ID NO 15
<211> LENGTH: 22
<212> TYPE: DNA
<213> ORGANISM: Artificial Sequence
<220> FEATURE:
<223> OTHER INFORMATION: BMP4 5' Primer

<400> SEQUENCE: 15
gccatacctt gacccgcaga ag                                               22

<210> SEQ ID NO 16
<211> LENGTH: 22
<212> TYPE: DNA
<213> ORGANISM: Artificial Sequence
<220> FEATURE:
```

```
<223> OTHER INFORMATION: BMP4 3' Primer

<400> SEQUENCE: 16
aaatggcact cagttcagtg gg                                          22

<210> SEQ ID NO 17
<211> LENGTH: 24
<212> TYPE: DNA
<213> ORGANISM: Artificial Sequence
<220> FEATURE:
<223> OTHER INFORMATION: TNAP 5' Primer

<400> SEQUENCE: 17
cccaaagcac cttattttc tacc                                         24

<210> SEQ ID NO 18
<211> LENGTH: 21
<212> TYPE: DNA
<213> ORGANISM: Artificial Sequence
<220> FEATURE:
<223> OTHER INFORMATION: TNAP 3' Primer

<400> SEQUENCE: 18
ttggcgagtc tctgcaattg g                                           21

<210> SEQ ID NO 19
<211> LENGTH: 21
<212> TYPE: DNA
<213> ORGANISM: Artificial Sequence
<220> FEATURE:
<223> OTHER INFORMATION: Oct4 5' Primer

<400> SEQUENCE: 19
cactctactc agtcccttt c                                            21

<210> SEQ ID NO 20
<211> LENGTH: 22
<212> TYPE: DNA
<213> ORGANISM: Artificial Sequence
<220> FEATURE:
<223> OTHER INFORMATION: Oct4 3' Primer

<400> SEQUENCE: 20
tgtgtcccag tctttattta ag                                          22

<210> SEQ ID NO 21
<211> LENGTH: 21
<212> TYPE: DNA
<213> ORGANISM: Artificial Sequence
<220> FEATURE:
<223> OTHER INFORMATION: Hoxb1 5' Primer

<400> SEQUENCE: 21
aactcatcag aggtcgaagg a                                           21

<210> SEQ ID NO 22
<211> LENGTH: 21
<212> TYPE: DNA
<213> ORGANISM: Artificial Sequence
<220> FEATURE:
<223> OTHER INFORMATION: Hoxb1 3' Primer

<400> SEQUENCE: 22
cggtgctatt gtaaggtctg c                                           21
```

<210> SEQ ID NO 23
<211> LENGTH: 19
<212> TYPE: DNA
<213> ORGANISM: Artificial Sequence
<220> FEATURE:
<223> OTHER INFORMATION: GCR1 5' Primer

<400> SEQUENCE: 23
ctactccgtg aagtctagg                                            19

<210> SEQ ID NO 24
<211> LENGTH: 21
<212> TYPE: DNA
<213> ORGANISM: Artificial Sequence
<220> FEATURE:
<223> OTHER INFORMATION: GCR1 3' Primer

<400> SEQUENCE: 24
aatgagtgtt acacctgcgt g                                         21

<210> SEQ ID NO 25
<211> LENGTH: 21
<212> TYPE: DNA
<213> ORGANISM: Artificial Sequence
<220> FEATURE:
<223> OTHER INFORMATION: GCR2 5' Primer

<400> SEQUENCE: 25
gccattcaga tgtctctgca c                                         21

<210> SEQ ID NO 26
<211> LENGTH: 21
<212> TYPE: DNA
<213> ORGANISM: Artificial Sequence
<220> FEATURE:
<223> OTHER INFORMATION: GCR2 3' Primer

<400> SEQUENCE: 26
ctcacagctt gaggcttcta a                                         21

<210> SEQ ID NO 27
<211> LENGTH: 137
<212> TYPE: PRT
<213> ORGANISM: Mus musculus

<400> SEQUENCE: 27

Met Asn His Thr Ser Gln Ala Phe Ile Thr Ala Ala Ser Gly Gly Gln
1               5                   10                  15

Pro Pro Asn Tyr Glu Arg Ile Lys Glu Glu Tyr Glu Val Ala Glu Met
            20                  25                  30

Gly Ala Pro His Gly Ser Ala Ser Val Arg Thr Thr Val Ile Asn Met
        35                  40                  45

Pro Arg Glu Val Ser Val Pro Asp His Val Val Trp Ser Leu Phe Asn
    50                  55                  60

Thr Leu Phe Met Asn Phe Cys Cys Leu Gly Phe Ile Ala Tyr Ala Tyr
65                  70                  75                  80

Ser Val Lys Ser Arg Asp Arg Lys Met Val Gly Asp Val Thr Gly Ala
                85                  90                  95

Gln Ala Tyr Ala Ser Thr Ala Lys Cys Leu Asn Ile Ser Thr Leu Val
            100                 105                 110

Leu Ser Ile Leu Met Val Val Ile Thr Ile Val Ser Val Ile Ile Ile
        115                 120                 125

```
Val Leu Asn Ala Gln Asn Leu His Thr
    130                 135
```

<210> SEQ ID NO 28
<211> LENGTH: 106
<212> TYPE: PRT
<213> ORGANISM: Mus musculus

<400> SEQUENCE: 28

```
Met Pro Lys Glu Gln Glu Val Val Leu Gly Ser Pro His Ile
1               5                   10                  15

Ser Thr Ser Ala Thr Ala Thr Thr Ile Asn Met Pro Glu Ile Ser Thr
            20                  25                  30

Pro Asp His Val Val Trp Ser Leu Phe Asn Thr Leu Phe Met Asn Phe
        35                  40                  45

Cys Cys Leu Gly Phe Val Ala Tyr Ala Tyr Ser Val Lys Ser Arg Asp
50                  55                  60

Arg Lys Met Val Gly Asp Thr Thr Gly Ala Gln Ala Phe Ala Ser Thr
65                  70                  75                  80

Ala Lys Cys Leu Asn Ile Ser Ser Leu Phe Phe Thr Ile Leu Thr Ala
            85                  90                  95

Ile Val Val Ile Val Val Cys Ala Ile Arg
            100                 105
```

<210> SEQ ID NO 29
<211> LENGTH: 144
<212> TYPE: PRT
<213> ORGANISM: Mus musculus

<400> SEQUENCE: 29

```
Met Ser His Asn Ser Gln Ala Phe Leu Ser Thr Asn Ala Gly Leu Pro
1               5                   10                  15

Pro Ser Tyr Glu Thr Ile Lys Glu Glu Tyr Gly Val Thr Glu Leu Gly
            20                  25                  30

Glu Pro Ser Asn Ser Ala Val Val Arg Thr Thr Val Ile Asn Met Pro
        35                  40                  45

Arg Glu Val Ser Val Pro Asp His Val Val Trp Ser Leu Phe Asn Thr
50                  55                  60

Leu Phe Phe Asn Ala Cys Cys Leu Gly Phe Val Ala Tyr Ala Tyr Ser
65                  70                  75                  80

Val Lys Ser Arg Asp Arg Lys Met Val Gly Asp Val Val Gly Ala Gln
            85                  90                  95

Ala Tyr Ala Ser Thr Ala Lys Cys Leu Asn Ile Ser Ser Leu Ile Phe
            100                 105                 110

Ser Ile Leu Met Val Ile Ile Cys Ile Ile Phe Ser Thr Thr Ser
            115                 120                 125

Val Val Val Phe Gln Ser Phe Ala Gln Arg Thr Pro His Ser Gly Phe
            130                 135                 140
```

<210> SEQ ID NO 30
<211> LENGTH: 134
<212> TYPE: PRT
<213> ORGANISM: Mus musculus

<400> SEQUENCE: 30

```
Met Asp Thr Ser Tyr Pro Arg Glu Asp Pro Arg Ala Pro Ser Ser Arg
1               5                   10                  15

Lys Ala Asp Ala Ala Ala His Thr Ala Leu Ser Met Gly Thr Pro Gly
```

-continued

```
                        20                  25                  30
Pro Thr Pro Arg Asp His Met Leu Trp Ser Val Phe Ser Thr Met Tyr
            35                  40                  45

Leu Asn Leu Cys Cys Leu Gly Phe Leu Ala Leu Val His Ser Val Lys
 50                      55                      60

Ala Arg Asp Gln Lys Met Ala Gly Asn Leu Glu Ala Ala Arg Gln Tyr
 65                  70                  75                  80

Gly Ser Lys Ala Lys Cys Tyr Asn Ile Leu Ala Ala Met Trp Thr Leu
                85                  90                  95

Val Pro Pro Leu Leu Leu Gly Leu Val Val Thr Gly Ala Leu His
             100                 105                 110

Leu Ser Lys Leu Ala Lys Asp Ser Ala Ala Phe Phe Ser Thr Lys Phe
             115                 120                 125

Asp Glu Glu Asp Tyr Asn
             130

<210> SEQ ID NO 31
<211> LENGTH: 104
<212> TYPE: PRT
<213> ORGANISM: Mus musculus

<400> SEQUENCE: 31

Met Val Lys Arg Asp Pro Asp Ser Ala Pro Val Pro Ser Thr Val Val
 1               5                  10                  15

Cys Ile Asn Ser Asp Val Ile Gln Pro Asp His Ile Thr Trp Ser Thr
                20                  25                  30

Phe Asn Thr Val Phe Met Asn Gly Cys Cys Leu Gly Phe Ile Ala Tyr
            35                  40                  45

Ile Tyr Ser Val Lys Ser Arg Asp Arg Lys Met Val Gly Asp Met Thr
 50                  55                  60

Gly Ala Gln Ser His Ala Ser Thr Ala Lys Ile Leu Asn Ile Leu Ala
 65                  70                  75                  80

Leu Val Ile Ser Leu Ile Phe Tyr Ile Met Leu Ile Val Leu Tyr Ser
                85                  90                  95

Phe Asn Leu Leu Gly Asn Gln Arg
             100

<210> SEQ ID NO 32
<211> LENGTH: 125
<212> TYPE: PRT
<213> ORGANISM: Homo sapiens

<400> SEQUENCE: 32

Met His Lys Glu Glu His Glu Val Ala Val Leu Gly Ala Pro Pro Ser
 1               5                  10                  15

Thr Ile Leu Pro Arg Ser Thr Val Ile Asn Ile His Ser Glu Thr Ser
                20                  25                  30

Val Pro Asp His Val Val Trp Ser Leu Phe Asn Thr Leu Phe Leu Asn
            35                  40                  45

Trp Cys Cys Leu Gly Phe Ile Ala Phe Ala Tyr Ser Val Lys Ser Arg
 50                  55                  60

Asp Arg Lys Met Val Gly Asp Val Thr Gly Ala Gln Ala Tyr Ala Ser
 65                  70                  75                  80

Thr Ala Lys Cys Leu Asn Ile Trp Ala Leu Ile Leu Gly Ile Leu Met
                85                  90                  95

Thr Ile Gly Phe Ile Leu Leu Val Phe Gly Ser Val Thr Val Tyr
```

```
                100                 105                 110
His Ile Met Leu Gln Ile Ile Gln Glu Lys Arg Gly Tyr
        115                 120                 125

<210> SEQ ID NO 33
<211> LENGTH: 132
<212> TYPE: PRT
<213> ORGANISM: Homo sapiens

<400> SEQUENCE: 33

Met Asn His Ile Val Gln Thr Phe Ser Pro Val Asn Ser Gly Gln Pro
1               5                   10                  15

Pro Asn Tyr Glu Met Leu Lys Glu Glu Gln Glu Val Ala Met Leu Gly
            20                  25                  30

Gly Pro His Asn Pro Ala Pro Pro Thr Ser Thr Val Ile His Ile Arg
        35                  40                  45

Ser Glu Thr Ser Val Pro Asp His Val Val Trp Ser Leu Phe Asn Thr
50                  55                  60

Leu Phe Met Asn Thr Cys Cys Leu Gly Phe Ile Ala Phe Ala Tyr Ser
65                  70                  75                  80

Val Lys Ser Arg Asp Arg Lys Met Val Gly Asp Val Thr Gly Ala Gln
                85                  90                  95

Ala Tyr Ala Ser Thr Ala Lys Cys Leu Asn Ile Trp Ala Leu Ile Leu
            100                 105                 110

Gly Ile Phe Met Thr Ile Leu Leu Val Ile Pro Val Leu Val Val
        115                 120                 125

Gln Ala Gln Arg
    130

<210> SEQ ID NO 34
<211> LENGTH: 133
<212> TYPE: PRT
<213> ORGANISM: Homo sapiens

<400> SEQUENCE: 34

Met Ser His Thr Val Gln Thr Phe Ser Pro Val Asn Ser Gly Gln
1               5                   10                  15

Pro Pro Asn Tyr Glu Met Leu Lys Glu Glu His Glu Val Ala Val Leu
            20                  25                  30

Gly Gly Pro His Asn Pro Ala Pro Pro Thr Ser Thr Val Ile His Ile
        35                  40                  45

Arg Ser Glu Thr Ser Val Pro Asp His Val Val Trp Ser Leu Phe Asn
    50                  55                  60

Thr Leu Phe Met Asn Pro Cys Cys Leu Gly Phe Ile Ala Phe Ala Tyr
65                  70                  75                  80

Ser Val Lys Ser Arg Asp Arg Lys Met Val Gly Asp Val Thr Gly Ala
                85                  90                  95

Gln Ala Tyr Ala Ser Thr Ala Lys Cys Leu Asn Ile Trp Ala Leu Ile
            100                 105                 110

Leu Gly Ile Leu Met Thr Ile Leu Leu Ile Val Ile Pro Val Leu Ile
        115                 120                 125

Phe Gln Ala Tyr Gly
    130

<210> SEQ ID NO 35
<211> LENGTH: 132
<212> TYPE: PRT
```

<213> ORGANISM: Homo sapiens

<400> SEQUENCE: 35

Met Asp Thr Ala Tyr Pro Arg Glu Asp Thr Arg Ala Pro Thr Pro Ser
1               5                   10                  15

Lys Ala Gly Ala His Thr Ala Leu Thr Leu Gly Ala Pro His Pro Pro
            20                  25                  30

Pro Arg Asp His Leu Ile Trp Ser Val Phe Ser Thr Leu Tyr Leu Asn
        35                  40                  45

Leu Cys Cys Leu Gly Phe Leu Ala Leu Ala Tyr Ser Ile Lys Ala Arg
    50                  55                  60

Asp Gln Lys Val Val Gly Asp Leu Glu Ala Ala Arg Arg Phe Gly Ser
65                  70                  75                  80

Lys Ala Lys Cys Tyr Asn Ile Leu Ala Ala Met Trp Thr Leu Val Pro
                85                  90                  95

Pro Leu Leu Leu Leu Gly Leu Val Val Thr Gly Ala Leu His Leu Ala
            100                 105                 110

Arg Leu Ala Lys Asp Ser Ala Ala Phe Phe Ser Thr Lys Phe Asp Asp
        115                 120                 125

Ala Asp Tyr Asp
        130

<210> SEQ ID NO 36
<211> LENGTH: 146
<212> TYPE: PRT
<213> ORGANISM: Bos primigenius

<400> SEQUENCE: 36

Met Asn Arg Thr Ser Gln Leu Leu Leu Thr Gly Ala His Gly Ala Val
1               5                   10                  15

Pro Pro Ala Tyr Glu Val Leu Lys Glu Glu His Glu Val Ala Val Leu
            20                  25                  30

Gly Ala Pro Gln Ser Gln Ala Pro Leu Thr Thr Thr Val Ile Asn Ile
        35                  40                  45

Arg Ser Asp Thr Ala Val Pro Asp His Ile Val Trp Ser Leu Phe Asn
    50                  55                  60

Thr Ile Phe Met Asn Trp Cys Cys Leu Gly Phe Val Ala Phe Ala Tyr
65                  70                  75                  80

Ser Val Lys Ser Arg Asp Arg Lys Met Val Gly Asp Ile Thr Gly Ala
                85                  90                  95

Gln Ser Tyr Ala Ser Thr Ala Lys Cys Leu Asn Ile Cys Ser Leu Val
            100                 105                 110

Leu Gly Ile Leu Leu Thr Val Val Leu Ile Val Leu Val Ser Asn Gly
        115                 120                 125

Ser Leu Met Ile Val Gln Ala Val Ser Glu Leu Met Gln Asn Tyr Gly
    130                 135                 140

Gly His
145

<210> SEQ ID NO 37
<211> LENGTH: 125
<212> TYPE: PRT
<213> ORGANISM: Bos primigenius

<400> SEQUENCE: 37

Met Ile Lys Glu Glu His Glu Val Ala Val Leu Gly Ala Pro Gln Ser
1               5                   10                  15

```
Arg Arg Pro Leu Thr Thr Thr Val Ile Asn Ile Arg Ser Asp Thr Ala
            20                  25                  30

Val Pro Asp His Ile Val Trp Ser Leu Phe Asn Thr Ile Phe Leu Asn
        35                  40                  45

Trp Cys Cys Leu Gly Phe Val Ala Phe Ala Tyr Ser Val Lys Ser Arg
    50                  55                  60

Asp Arg Lys Met Val Gly Asp Ile Thr Gly Ala Gln Ser Tyr Ala Ser
65                  70                  75                  80

Thr Ala Lys Cys Leu Asn Ile Trp Ala Leu Val Leu Gly Ile Leu Leu
                85                  90                  95

Thr Ile Gly Ser Ile Val Leu Leu Ile Phe Gly Tyr Met Ala Val Tyr
                100                 105                 110

Gln Thr Val Phe Leu Leu Met Gln Glu Lys Arg Gly His
                115                 120                 125
```

<210> SEQ ID NO 38
<211> LENGTH: 137
<212> TYPE: PRT
<213> ORGANISM: Rattus sp

<400> SEQUENCE: 38

```
Met Asn His Thr Ser Gln Ala Phe Val Asn Ala Thr Gly Gly Gln
1               5                   10                  15

Pro Pro Asn Tyr Glu Arg Ile Lys Glu Glu Tyr Glu Val Ser Glu Leu
            20                  25                  30

Gly Ala Pro His Gly Ser Ala Ser Val Arg Thr Thr Val Ile Asn Met
        35                  40                  45

Pro Arg Glu Val Ser Val Pro Asp His Val Val Trp Ser Leu Phe Asn
    50                  55                  60

Thr Leu Phe Met Asn Phe Cys Cys Leu Gly Phe Ile Ala Tyr Ala Tyr
65                  70                  75                  80

Ser Val Lys Ser Arg Asp Arg Lys Met Val Gly Asp Met Thr Gly Ala
                85                  90                  95

Gln Ala Tyr Ala Ser Thr Ala Lys Cys Leu Asn Ile Ser Ser Leu Val
                100                 105                 110

Leu Ser Ile Leu Met Val Ile Ile Thr Ile Val Thr Val Ile Ile
                115                 120                 125

Ala Leu Asn Ala Pro Arg Leu Gln Thr
        130                 135
```

<210> SEQ ID NO 39
<211> LENGTH: 137
<212> TYPE: PRT
<213> ORGANISM: Rattus sp

<400> SEQUENCE: 39

```
Met Asn His Thr Ser Gln Ala Phe Ala Thr Val Ala Thr Gly Gly Gln
1               5                   10                  15

Pro Pro Asn Tyr Glu Arg Ile Lys Glu Glu Tyr Glu Val Ser Glu Leu
            20                  25                  30

Gly Ala Pro His Gly Ser Ala Ser Val Arg Thr Thr Val Ile Asn Met
        35                  40                  45

Pro Arg Glu Val Ser Val Pro Asp His Val Val Trp Ser Leu Phe Asn
    50                  55                  60

Thr Leu Phe Met Asn Phe Cys Cys Leu Gly Phe Ile Ala Tyr Ala Tyr
65                  70                  75                  80
```

```
Ser Val Lys Ser Arg Asp Arg Lys Met Val Gly Asp Met Thr Gly Ala
                85                  90                  95

Gln Ala Tyr Ala Ser Thr Ala Lys Cys Leu Asn Ile Ser Ser Leu Val
            100                 105                 110

Leu Ser Ile Leu Met Val Ile Ile Thr Ile Val Thr Val Val Ile Ile
        115                 120                 125

Ala Leu Asn Ala Pro Arg Leu Gln Thr
    130                 135

<210> SEQ ID NO 40
<211> LENGTH: 144
<212> TYPE: PRT
<213> ORGANISM: Rattus sp

<400> SEQUENCE: 40

Met Ser His Asn Ser Gln Ala Phe Leu Pro Ala Asn Ala Gly Leu Pro
1               5                   10                  15

Pro Ser Tyr Glu Thr Ile Lys Glu Glu Tyr Gly Val Thr Glu Leu Gly
            20                  25                  30

Glu Pro Asn Asn Ser Ala Val Val Arg Thr Thr Val Ile Asn Met Pro
        35                  40                  45

Arg Glu Val Ser Val Pro Asp His Val Val Trp Ser Leu Phe Asn Thr
50                  55                  60

Leu Phe Phe Asn Ala Cys Cys Leu Gly Phe Ile Ala Tyr Ala Tyr Ser
65                  70                  75                  80

Val Lys Ser Arg Asp Arg Lys Met Val Gly Asp Val Ile Gly Ala Gln
                85                  90                  95

Ala Tyr Ala Ser Thr Ala Lys Cys Leu Asn Ile Ser Ser Leu Ile Phe
            100                 105                 110

Ser Val Leu Met Val Ile Ile Cys Ile Ile Phe Ser Thr Thr Ser
        115                 120                 125

Ala Val Val Phe Gln Ser Leu Ser Gln Arg Thr Pro His Ser Gly Phe
    130                 135                 140

<210> SEQ ID NO 41
<211> LENGTH: 93
<212> TYPE: PRT
<213> ORGANISM: Rattus sp

<400> SEQUENCE: 41

Met Asn His Thr Ser Gln Ala Phe Val Asn Ala Thr Gly Gly Gln
1               5                   10                  15

Pro Pro Asn Tyr Glu Arg Ile Lys Glu Glu Tyr Glu Val Ser Glu Leu
            20                  25                  30

Gly Ala Pro His Gly Ser Ala Ser Val Arg Thr Thr Val Ile Asn Met
        35                  40                  45

Pro Arg Glu Val Ser Val Pro Asp His Val Val Trp Ser Leu Phe Asn
50                  55                  60

Thr Leu Phe Met Asn Phe Cys Cys Leu Gly Phe Ile Ala Tyr Ala Tyr
65                  70                  75                  80

Ser Val Lys Val Ser Val Leu Glu Val Gly Val Met Val
                85                  90

<210> SEQ ID NO 42
<211> LENGTH: 155
<212> TYPE: PRT
<213> ORGANISM: Artificial Sequence
```

```
<220> FEATURE:
<223> OTHER INFORMATION: Consensus Fig. 10A-B
<220> FEATURE:
<221> NAME/KEY: MISC_FEATURE
<222> LOCATION: (9)..(11)
<223> OTHER INFORMATION: "X" is an undefined amino acid in the alignment
<220> FEATURE:
<221> NAME/KEY: MISC_FEATURE
<222> LOCATION: (13)..(13)
<223> OTHER INFORMATION: "X" is an undefined amino acid in the alignment
<220> FEATURE:
<221> NAME/KEY: MISC_FEATURE
<222> LOCATION: (22)..(23)
<223> OTHER INFORMATION: "X" is an undefined amino acid in the alignment
<220> FEATURE:
<221> NAME/KEY: MISC_FEATURE
<222> LOCATION: (30)..(31)
<223> OTHER INFORMATION: "X" is an undefined amino acid in the alignment
<220> FEATURE:
<221> NAME/KEY: MISC_FEATURE
<222> LOCATION: (36)..(37)
<223> OTHER INFORMATION: "X" is an undefined amino acid in the alignment
<220> FEATURE:
<221> NAME/KEY: MISC_FEATURE
<222> LOCATION: (42)..(44)
<223> OTHER INFORMATION: "X" is an undefined amino acid in the alignment
<220> FEATURE:
<221> NAME/KEY: MISC_FEATURE
<222> LOCATION: (51)..(52)
<223> OTHER INFORMATION: "X" is an undefined amino acid in the alignment
<220> FEATURE:
<221> NAME/KEY: MISC_FEATURE
<222> LOCATION: (54)..(54)
<223> OTHER INFORMATION: "X" is an undefined amino acid in the alignment
<220> FEATURE:
<221> NAME/KEY: misc_feature
<222> LOCATION: (73)..(73)
<223> OTHER INFORMATION: Xaa can be any naturally occurring amino acid
<220> FEATURE:
<221> NAME/KEY: MISC_FEATURE
<222> LOCATION: (96)..(96)
<223> OTHER INFORMATION: "X" is an undefined amino acid in the alignment
<220> FEATURE:
<221> NAME/KEY: MISC_FEATURE
<222> LOCATION: (112)..(113)
<223> OTHER INFORMATION: "X" is an undefined amino acid in the alignment
<220> FEATURE:
<221> NAME/KEY: MISC_FEATURE
<222> LOCATION: (115)..(115)
<223> OTHER INFORMATION: "X" is an undefined amino acid in the alignment
<220> FEATURE:
<221> NAME/KEY: MISC_FEATURE
<222> LOCATION: (117)..(117)
<223> OTHER INFORMATION: "X" is an undefined amino acid in the alignment
<220> FEATURE:
<221> NAME/KEY: MISC_FEATURE
<222> LOCATION: (121)..(121)
<223> OTHER INFORMATION: "X" is an undefined amino acid in the alignment
<220> FEATURE:
<221> NAME/KEY: MISC_FEATURE
<222> LOCATION: (123)..(124)
<223> OTHER INFORMATION: "X" is an undefined amino acid in the alignment
<220> FEATURE:
<221> NAME/KEY: MISC_FEATURE
<222> LOCATION: (127)..(132)
<223> OTHER INFORMATION: "X" is an undefined amino acid in the alignment
<220> FEATURE:
<221> NAME/KEY: MISC_FEATURE
<222> LOCATION: (134)..(149)
<223> OTHER INFORMATION: "X" is an undefined amino acid in the alignment
<220> FEATURE:
<221> NAME/KEY: MISC_FEATURE
<222> LOCATION: (152)..(153)
<223> OTHER INFORMATION: "X" is an undefined amino acid in the alignment

<400> SEQUENCE: 42

Met Asn His Thr Ser Gln Ala Phe Xaa Xaa Xaa Ala Xaa Gly Gly Gln
1               5                   10                  15
```

```
Pro Pro Asn Tyr Glu Xaa Xaa Lys Glu Glu Tyr Glu Val Xaa Xaa Leu
            20                  25                  30

Gly Ala Pro Xaa Xaa Arg Lys Ser Ala Xaa Xaa Xaa Thr Thr Val Ile
        35                  40                  45

Asn Met Xaa Xaa Glu Xaa Ser Val Pro Arg Asp His Val Val Trp Ser
    50                  55                  60

Leu Phe Asn Thr Leu Phe Met Asn Xaa Cys Cys Leu Gly Phe Ile Ala
65                  70                  75                  80

Tyr Ala Tyr Ser Val Lys Ser Arg Asp Arg Lys Met Val Gly Asp Xaa
                85                  90                  95

Thr Gly Ala Gln Ala Tyr Ala Ser Thr Ala Lys Cys Leu Asn Ile Xaa
            100                 105                 110

Xaa Leu Xaa Leu Xaa Ile Leu Met Xaa Ile Xaa Xaa Ile Val Xaa Xaa
        115                 120                 125

Xaa Xaa Xaa Xaa Leu Xaa Xaa Xaa Xaa Xaa Xaa Xaa Xaa Xaa Xaa Xaa
        130                 135                 140

Xaa Xaa Xaa Xaa Xaa Phe Asp Xaa Xaa Asp Tyr
145                 150                 155

<210> SEQ ID NO 43
<211> LENGTH: 150
<212> TYPE: PRT
<213> ORGANISM: Mus musculus

<400> SEQUENCE: 43

Met Glu Glu Pro Ser Glu Lys Val Asp Pro Met Lys Asp Pro Glu Thr
1               5                   10                  15

Pro Gln Lys Lys Asp Glu Glu Asp Ala Leu Asp Asp Thr Asp Val Leu
            20                  25                  30

Gln Pro Glu Thr Leu Val Lys Val Met Lys Lys Leu Thr Leu Asn Pro
        35                  40                  45

Gly Val Lys Arg Ser Ala Arg Arg Ser Leu Arg Asn Arg Ile Ala
    50                  55                  60

Ala Val Pro Val Glu Asn Lys Ser Glu Lys Ile Arg Arg Glu Val Gln
65                  70                  75                  80

Ser Ala Phe Pro Lys Arg Arg Val Arg Thr Leu Leu Ser Val Leu Lys
                85                  90                  95

Asp Pro Ile Ala Lys Met Arg Arg Leu Val Arg Ile Glu Gln Arg Gln
            100                 105                 110

Lys Arg Leu Glu Gly Asn Glu Phe Glu Arg Asp Ser Glu Pro Phe Arg
        115                 120                 125

Cys Leu Cys Thr Phe Cys His Tyr Gln Arg Trp Asp Pro Ser Glu Asn
    130                 135                 140

Ala Lys Ile Gly Lys Asn
145                 150

<210> SEQ ID NO 44
<211> LENGTH: 158
<212> TYPE: PRT
<213> ORGANISM: Rattus sp

<400> SEQUENCE: 44

Met Asp Glu Pro Ser Glu Lys Val Asp Pro Val Val Asn Pro Glu Thr
1               5                   10                  15

Gln Met Tyr Asp Gly Ser Gln Arg Glu Asp Gly Asp Ser Pro Asp
            20                  25                  30
```

```
Asp Ser Glu Ile Leu Gln Pro Glu Thr Leu Val Lys Val Met Lys Lys
            35                  40                  45

Leu Thr Leu Asn Pro Ser Ala Lys Pro Thr Lys Tyr His Arg Arg Gln
 50                  55                  60

Arg Val Arg Leu Gln Val Lys Ser Gln Pro Val Glu Asn Arg Ser Glu
 65                  70                  75                  80

Arg Ile Met Arg Glu Val Gln Ser Ala Phe Pro Arg Arg Arg Val Arg
                 85                  90                  95

Thr Leu Leu Ser Val Leu Lys Asp Pro Ile Ala Arg Met Arg Arg Phe
                 100                 105                 110

Val Arg Ile Glu Gln Arg Gln Arg Gln Leu Glu Gly Asn Glu Arg Arg
                 115                 120                 125

Asp Glu Pro Phe Arg Cys Leu Cys Thr Phe Cys His Tyr Gln Arg Trp
            130                 135                 140

Asp Pro Ser Glu Asn Ala Lys Ile Gly Gln Asn Gln Lys Asn
145                 150                 155

<210> SEQ ID NO 45
<211> LENGTH: 159
<212> TYPE: PRT
<213> ORGANISM: Homo sapiens

<400> SEQUENCE: 45

Met Asp Pro Ser Gln Phe Asn Pro Thr Tyr Ile Pro Gly Ser Pro Gln
 1               5                   10                  15

Met Leu Thr Glu Glu Asn Ser Arg Asp Asp Ser Gly Ala Ser Gln Ile
                 20                  25                  30

Ser Ser Glu Thr Leu Ile Lys Asn Leu Ser Asn Leu Thr Ile Asn Ala
            35                  40                  45

Ser Ser Glu Ser Val Ser Pro Leu Ser Glu Ala Leu Leu Arg Arg Glu
 50                  55                  60

Ser Val Gly Ala Ala Val Leu Arg Glu Ile Glu Asp Glu Trp Leu Tyr
 65                  70                  75                  80

Ser Arg Arg Gly Val Arg Thr Leu Leu Ser Val Gln Arg Glu Lys Met
                 85                  90                  95

Ala Arg Leu Arg Tyr Met Leu Leu Gly Gly Val Arg Thr His Glu Arg
                 100                 105                 110

Arg Pro Thr Asn Lys Glu Pro Lys Gly Val Lys Lys Glu Ser Arg Pro
            115                 120                 125

Phe Lys Cys Pro Cys Ser Phe Cys Val Ser Asn Gly Trp Asp Pro Ser
            130                 135                 140

Glu Asn Ala Arg Ile Gly Asn Gln Asp Thr Lys Pro Leu Gln Pro
145                 150                 155

<210> SEQ ID NO 46
<211> LENGTH: 21
<212> TYPE: DNA
<213> ORGANISM: Artificial Sequence
<220> FEATURE:
<223> OTHER INFORMATION: stella Primer

<400> SEQUENCE: 46
ctcacagctt gaggcttcta a                                          21

<210> SEQ ID NO 47
<211> LENGTH: 21
<212> TYPE: DNA
```

```
<213> ORGANISM: Artificial Sequence
<220> FEATURE:
<223> OTHER INFORMATION: stella Primer

<400> SEQUENCE: 47
gcgattcaga tgtctctgca c                                              21

<210> SEQ ID NO 48
<211> LENGTH: 24
<212> TYPE: DNA
<213> ORGANISM: Artificial Sequence
<220> FEATURE:
<223> OTHER INFORMATION: fragilis Primer

<400> SEQUENCE: 48
gttatcacca ttgttagtgt catc                                           24

<210> SEQ ID NO 49
<211> LENGTH: 21
<212> TYPE: DNA
<213> ORGANISM: Artificial Sequence
<220> FEATURE:
<223> OTHER INFORMATION: fragilis Primer

<400> SEQUENCE: 49
aatgagtgtt acacctgcgt g                                              21

<210> SEQ ID NO 50
<211> LENGTH: 22
<212> TYPE: DNA
<213> ORGANISM: Artificial Sequence
<220> FEATURE:
<223> OTHER INFORMATION: fragilis3 Primer

<400> SEQUENCE: 50
gatcttcagc atccttatgg tc                                             22

<210> SEQ ID NO 51
<211> LENGTH: 22
<212> TYPE: DNA
<213> ORGANISM: Artificial Sequence
<220> FEATURE:
<223> OTHER INFORMATION: fragilis3 Primer

<400> SEQUENCE: 51
gaaggtaaca tttgcatacg cg                                             22

<210> SEQ ID NO 52
<211> LENGTH: 20
<212> TYPE: DNA
<213> ORGANISM: Artificial Sequence
<220> FEATURE:
<223> OTHER INFORMATION: fragilis2 Primer

<400> SEQUENCE: 52
ccttccttat tctcactctg                                                20

<210> SEQ ID NO 53
<211> LENGTH: 20
<212> TYPE: DNA
<213> ORGANISM: Artificial Sequence
<220> FEATURE:
<223> OTHER INFORMATION: fragilis2 Primer

<400> SEQUENCE: 53
gttgcaagac atctcacatc                                                20
```

<210> SEQ ID NO 54
<211> LENGTH: 21
<212> TYPE: DNA
<213> ORGANISM: Artificial Sequence
<220> FEATURE:
<223> OTHER INFORMATION: fragilis4 Primer

<400> SEQUENCE: 54
aacttggagg ctgcaaggca g                                          21

<210> SEQ ID NO 55
<211> LENGTH: 22
<212> TYPE: DNA
<213> ORGANISM: Artificial Sequence
<220> FEATURE:
<223> OTHER INFORMATION: fragilis4 Primer

<400> SEQUENCE: 55
ctcggaactc ttagttatag tc                                         22

<210> SEQ ID NO 56
<211> LENGTH: 20
<212> TYPE: DNA
<213> ORGANISM: Artificial Sequence
<220> FEATURE:
<223> OTHER INFORMATION: fragilis5 Primer

<400> SEQUENCE: 56
tgctctggtc atctccctca                                            20

<210> SEQ ID NO 57
<211> LENGTH: 20
<212> TYPE: DNA
<213> ORGANISM: Artificial Sequence
<220> FEATURE:
<223> OTHER INFORMATION: fragilis5 Primer

<400> SEQUENCE: 57
caggataagg ggcaactctg                                            20

<210> SEQ ID NO 58
<211> LENGTH: 12
<212> TYPE: DNA
<213> ORGANISM: Artificial Sequence
<220> FEATURE:
<223> OTHER INFORMATION: Interferon stimulable response elements
<220> FEATURE:
<221> NAME/KEY: misc_feature
<222> LOCATION: (6)..(7)
<223> OTHER INFORMATION: n is C, A, G or T

<400> SEQUENCE: 58
ggaaanngaa ac                                                    12

<210> SEQ ID NO 59
<211> LENGTH: 22
<212> TYPE: DNA
<213> ORGANISM: Artificial Sequence
<220> FEATURE:
<223> OTHER INFORMATION: STELLA Primer

<400> SEQUENCE: 59
caatttgagg ctctgtcatc ag                                         22

<210> SEQ ID NO 60

-continued

```
<210> SEQ ID NO 61
<211> LENGTH: 21
<212> TYPE: DNA
<213> ORGANISM: Artificial Sequence
<220> FEATURE:
<223> OTHER INFORMATION: STELLA primer

<400> SEQUENCE: 60
ttcatctcac tgactttggg c                                                 21

<210> SEQ ID NO 61
<211> LENGTH: 20
<212> TYPE: DNA
<213> ORGANISM: Artificial Sequence
<220> FEATURE:
<223> OTHER INFORMATION: ribosomal protein L32 Primer

<400> SEQUENCE: 61
agttcctggt ccacaacgtc                                                   20

<210> SEQ ID NO 62
<211> LENGTH: 20
<212> TYPE: DNA
<213> ORGANISM: Artificial Sequence
<220> FEATURE:
<223> OTHER INFORMATION: ribosomal protein L32 Primer

<400> SEQUENCE: 62
tgcacatgag ctgcctactc                                                   20

<210> SEQ ID NO 63
<211> LENGTH: 21
<212> TYPE: DNA
<213> ORGANISM: Artificial Sequence
<220> FEATURE:
<223> OTHER INFORMATION: exon 2-specific Primer

<400> SEQUENCE: 63
agacgtccta caaccagaaa c                                                 21

<210> SEQ ID NO 64
<211> LENGTH: 21
<212> TYPE: DNA
<213> ORGANISM: Artificial Sequence
<220> FEATURE:
<223> OTHER INFORMATION: exon 2-specific Primer

<400> SEQUENCE: 64
ccgaacaagt cttctcatct t                                                 21
```

US 7,884,193 B2

ANTIBODIES FOR IDENTIFICATION OF MURINE FRAGILIS EXTRACELLULAR DOMAIN AND METHODS FOR IDENTIFYING PLURIPOTENT CELLS

CROSS REFERENCE TO RELATED APPLICATIONS

This application is a divisional of U.S. application Ser. No. 10/646,390, filed Aug. 21, 2003, now U.S. Pat. No. 7,226,994, as a continuation-in-part of U.S. application Ser. No. 10/621,911, filed Jul. 17, 2003, now abandoned, and as a continuation-in-part of International Application No. PCT/GB02/00215, filed Jan. 18, 2002, which claims priority from GB Patent Application No. 0101300.2, filed Jan. 18, 2001. All of the above referenced applications are herein incorporated by reference.

FIELD

The present invention relates to the fields of development, molecular biology and genetics. More particularly, the invention relates to genes which are expressed exclusively in the earliest populations of primordial germ cells (PGCs) and the use of such genes and the products thereof in identification of pluripotent and multipotent cells such as PGCs, pluripotent embryonic stem cells (ES) and pluripotent embryonic germ cells (EG), in cell populations. They are also markers for a change in the sate of cells from being non pluripotent to becoming pluripotent, and in being able to confer this state on a non pluripotent cell.

INTRODUCTION

Post fertilisation, the early mammalian embryo undergoes four rounds of cleavage to form a morula of 16 cells. These cells, following further rounds of division, develop into a blastocyst in which the cells can be divided into two distinct regions; the inner cell mass, which will form the embryo, and the trophectoderm, which will form extra-embryonic tissue, such as the placenta.

The cells that form part of the embryo up until the formation of the blastocyst are totipotent; in other words, each of the cells has the ability to give rise to a complete individual embryo, and to all the extra-embryonic tissues required for its development. After blastocyst formation, the cells of the inner cell mass are no longer totipotent, but are pluripotent, in that they can give rise to a range of different tissues. A known marker for such cells is the expression of the enzyme alkaline phosphatase and Oct4.

Primordial germ cells (PGCs) are pluripotent cells that have the ability to differentiate into all three primary germ layers. In mammals, the PGCs migrate from the base of the allantois, through the hindgut epithelium and dorsal mesentery, to colonise the gonadal anlague. The PGC-derived cells have a characteristically low cytoplasm/nucleus ratio, usually with prominent nucleoli. PGCs may be isolated from the embryos by removing the genital ridge of the embryo, dissociating the PGCs from the gonadal anlague, and collecting the PGCs. The earliest PGC population is reported to consist of a cluster of some 45 (forty-five) alkaline phosphatase positive cells, found at the base of the emerging allantois, 7.25 days post-fertilisation (Ginsburg et al., (1990) Development 110: 521-528).

PGCs have many applications in modern biotechnology and molecular biology. They are useful in the production of transgenic animals, where embryonic germ (EG) cells derived from PGCs may be used in much the same manner as embryonic stem (ES) cells (Labosky et al., (1994) Development 120:3197-3204). Moreover, they are useful in the study of foetal development and the provision of pluripotent stem cells for tissue regeneration in the therapy of degenerative diseases and repopulation of damaged tissue following trauma. Above all, PGCs while having some specialised properties, retain an underlying pluripotency, which is lost from the neighbouring cells that surround the founder population of PGCs that acquire a somatic cell fate. PGCs and the surrounding somatic cells share a common ancestry. However, the founder PGCs are few in number and difficult to isolate from embryonic tissue and the surrounding somatic cells, which complicates their study and the development of techniques which make use thereof.

Little is known in the art about the expression of genes in the founder population of PGCs and the relationship between PGC-specific gene expression and the retention of pluripotency in these cells. Certain markers for PGCs are known—for example, the expression of tissue non-specific alkaline phosphatase (TNAP) has been used as a marker for early PGCs (Ginsburg et al., (1990) Development 110:521-528). Oct4 is known to be expressed in PGCs, but not somatic cells (Yoem et al., (1996) Development 122:881-894). Other markers, such as BMP4, are known to be expressed primarily in somatic tissues (Lawson et al., (1999) Genes & Dev. 13:424-436). However, none of these genes is specific for PGCs, since they are also expressed in other tissue types. There is therefore a need in the art for the identification of genes which may be used as markers for PGCs and which may provide an insight into the biology of germ cell development and the nature of the pluripotent state.

SUMMARY

We disclose the sequences of two genes which are expressed specifically in PGCs and other pluripotent cells. The sequence of the genes from mouse is set forth in SEQ ID NO: 1 (GCR1 or Fragilis) and SEQ ID NO: 3 (GCR2, or Stella). Corresponding amino acid sequences for mouse GCR1 and GCR2 are set out in SEQ ID NO: 2 and SEQ ID NO: 4 respectively. Nucleic acid sequences of rat GCR2 homologues are set out in SEQ ID NO: 5, SEQ ID NO: 6, SEQ ID NO: 7, SEQ ID NO: 8, and SEQ ID NO: 9.

According to a first aspect of the present invention, we provide a GCR1 polypeptide, or a fragment, homologue, variant or derivative thereof. Preferably, the polypeptide has at least 50%, 60%, 70%, 80%, 90% or 95% homology to a sequence shown in SEQ ID NO: 2.

There is provided, according to a second aspect of the present invention, GCR2 polypeptide, or a fragment, homologue, variant or derivative thereof. Preferably, the polypeptide has at least 50%, 60%, 70%, 80%, 90% or 95% homology to a sequence shown in SEQ ID NO: 4.

We provide, according to a third aspect of the present invention, a nucleic acid encoding a polypeptide according to any preceding claim.

As a fourth aspect of the present invention, there is provided a nucleic acid having at least 90% homology with the sequence set forth in SEQ ID NO: 1, or a fragment, variant or derivative thereof.

We provide, according to a fifth aspect of the present invention, a nucleic acid having at least 75% homology with the sequence set forth in SEQ ID NO: 3, SEQ ID NO: 5, SEQ ID NO: 6, SEQ ID NO: 7, SEQ ID NO: 8 or SEQ ID NO: 9, or a fragment, variant or derivative thereof.

The present invention, in a sixth aspect, provides a nucleic acid comprising a sequence of 25 contiguous nucleotides of a nucleic acid according to the third, fourth or fifth aspect of the invention.

In a seventh aspect of the present invention, there is provided a nucleic acid comprising a sequence of 15 contiguous nucleotides of a nucleic acid according to the third, fourth, fifth or sixth aspect of the invention.

According to an eighth aspect of the present invention, we provide a complement of a nucleic acid sequence according to any of the third to seventh aspect of the invention.

Preferably, such a nucleic acid comprises one or more nucleotide substitutions, wherein such substitutions do not alter the coding specificity of said nucleic acid as a result of the degeneracy of the genetic code.

We provide, according to a ninth aspect of the invention, a polypeptide encoded by a nucleic acid according to any preceding aspect of the invention.

Preferably, the polypeptide comprises a sequence shown in SEQ ID NO: 2 or SEQ ID NO: 4.

There is provided, in accordance with a tenth aspect of the present invention, a method for identifying a pluripotent cell, comprising detecting the presence of a polypeptide according to the first, second, ninth or tenth aspect of the invention or the expression of a nucleic acid according to any of the third to eighth aspect of the invention, or a homologue thereof.

Preferably, the method comprises the steps of amplifying nucleic acids from a putative pluripotent cell using 5' and 3' primers specific for GCR1 (Fragilis) and/or GCR2 (Stella), and detecting amplified nucleic acid thus produced. Preferably, the expression of the nucleic acid sequence is detected by in situ hybridisation.

The expression of the nucleic acid sequence may be determined by detecting the protein product encoded thereby. Alternatively or in addition, the protein product may be detected by immunostaining.

As an eleventh aspect of the invention, we provide an antibody specific for a polypeptide according to the first, second, ninth or tenth aspect of the invention. preferably, the antibody is capable of specifically binding to an extracellular domain of GCR1.

We provide, according to a twelfth aspect of the invention, there is provided use of such an antibody for the identification and/or isolation of a pluripotent cell.

We further provide, according to a thirteenth aspect of the invention, a pluripotent cell identified by a method as set out previously.

There is provided, according to a fourteenth aspect of the present invention, a method for isolating a gene specifically expressed in a pluripotent cell, comprising the steps of: (a) providing a population of cells containing a pluripotent cell; (b) isolating one or more pluripotent cells therefrom and providing single-cell pluripotent cell isolates; (c) amplifying the transcribed nucleic acid present in a single pluripotent cell; (d) conducting a subtractive hybridisation screen to identify transcripts present in pluripotent cells but not in somatic cells; and (e) probing a nucleic acid library with one or more transcripts identified in (d) to clone one or more genes which are specifically expressed in pluripotent cells.

In a highly preferred embodiment, the pluripotent cell is selected from the group consisting of: a primordial germ cell (PGC), an embryonic stem cell (ES) and an embryonic germ cell (EG). Preferably, the pluripotent cell comprises a primordial germ cell.

BRIEF DESCRIPTION OF THE FIGURES

FIG. 1: Nucleotide and deduced amino acid sequence of Fragilis. Predicted positions of the two transmembrane domains (TM I and TM II) are underlined and indicated by bold letters. The poly(A) signal is underlined.

FIG. 2: Nucleotide and deduced amino acid sequence of Stella. Three nuclear localization signals are underlined. A potential nuclear export signal is underlined twice, and the hydrophobic residues are indicated in bold. Helical structures in a motif with similarity to SAP domain (a.a.28 to a.a.63) are underlined in red, and the conserved residues are indicated by blue. A splicing factor-like motif is underlined and the conserved residues are indicated in green. Poly(A) signals are also underlined.

FIG. 16. Knockout strategy of stella and confirmation of correct targeting by Southern-blot and RT-PCR. a, The targeting vector was designed to delete exon 2 and replace it with an IRES-LacZ/MC-neo reporter-selection cassette. HSV-TK was used for negative selection against non-homologous recombination. 5', 3' and neo-probes were used to confirm correct targeting of ES-cells. b, Southern blot analysis of genomic DNA derived from littermate mice born from a stellar$^{+/-}$ intercross. The example shows a NcoI digest hybridised with the 3' probe, indicating the absence of the wild-type allele in stella$^{-/-}$ mice. c, RT-PCR of testis (te) or ovary (ov) RNA from male or female mice, respectively using exon 2-specific primers. The wild-type stella transcript is reduced in stella$^{+/-}$ mice compared to stella$^{+/+}$ mice and absent in stella$^{-/-}$ mice. Gapdh was used as a control for equivalent quality and amount of RNA.-Rt, without reverse transcriptase; 0, water control.

DETAILED DESCRIPTION

GCR1 (Fragilis) and GCR2 (Stella)

Figure 3:
FIG. 3: Expression of Fragilis in embryonic stem (ES) cells. ES cells are fixed in 4% paraformaldehyde in PBS for 10 min. at room temperature and processed for immunohistochemistry as described by Saitou et al., (1998). *J Cell Biol* 141, 397-408. (1998). Fragilis expression is similarly detected in E6.5 proximal epiblast cells, which are germ cell competent cells, and in newly specified germ cells. The expression declines after E8.5 following completion of the specification of germ cells fate.

The disclosure provides generally for GCR1 (Fragilis) and GCR2 (Stella) nucleic acids, polypeptides, as well as fragments, homologues, variants and derivatives thereof.

The names "GCR1" and "Fragilis" should be understood as synonymous with each other, and likewise, "GCR2" and "Stella" should be considered synonyms. Nucleic acid and amino acid sequences of GCR1/Fragilis are set out in SEQ ID NO: 1 and 2, while nucleic acid sequences of GCR2/Stella are set out in SEQ ID NO: 3, 5, 6, 7, 8 and 9, with an amino acid sequence of GCR2/Stella shown in SEQ ID NO: 4.

In preferred embodiments, however, GCR1/Fragilis should be taken to refer to the nucleic acid sequence shown in SEQ ID NO: 1, or the amino acid sequence shown in SEQ ID NO: 2, as the context requires. Furthermore, in preferred embodiments, GCR2/Stella should be taken to refer to the nucleic acid sequence shown in SEQ ID NO: 3, or the amino acid sequence shown in SEQ ID NO: 4, as the context requires.

GCR1 and GCR2 are PGC-specific transcripts. GCR1 is upregulated during the process of lineage commitment of PGCs, while GCR2 is upregulated after GCR1, and marks commitment to the PGC fate. The first gene, GCR1 (Germ cell restricted-1, Fragilis), encodes a 137 amino acid protein with a predicted molecular weight of 15.0 kD. The best fit model of the EMBL program PredictProtein predicts two transmembrane domains, both N and C terminus ends being located outside. The BLASTP search revealed that Fragilis is a novel member of the interferon-inducible protein family. One prototype member, human 9-27 (identical to Leu-13 antigen), is inducible by interferon in leukocytes and endothelial cells, and is located at the cell surface as a component of a multimeric complex involved in the transduction of antiproliferative and homotypic adhesion signals (Deblandre, 1995). The BLASTN search revealed that the Fragilis sequence was found in ESTs derived from many different tissues both from embryos and adults, indicating that Fragilis may play a common role in different developmental and cell biological contexts. Database searches reveal a sequence match with the rat interferon-inducible protein (sp:INIB RAT, pir:JC1241) with unknown function. The GCR1 sequence appears six times in our screen, indicating high level expression in PGCs.

The second gene, GCR2, (Stella) encodes a 150 amino acid protein, of 18 kD. It has no sequence homology with any known protein, contains several nuclear localisation consensus sequences and is highly basic pI (pI=9.67, the content of basic residues=23.3%), indicating a possible affinity to DNA. Furthermore a potential nuclear export signal was identified, indicating that Stella may shuttle between the nucleus and the cytoplasm. BLASTN analysis revealed that the Stella sequence was found only in the preimplantation embryo and germ line (newborn ovary, female 12.5 mesonephros and gonad etc.) ESTs indicating its predominant expression in totipotent and pluripotent cells. Interestingly, we found that Stella contains in its N terminus a modular domain which has some sequence similarity with the SAP motif. This motif is a putative DNA-binding domain involved in chromosomal orgainisation. Furthermore, the SMART program revealed the presence of a splicing factor motif-like structure in its C-terminus, These findings indicate a possible involvement of Stella in chromosomal organisation and RNA processing.

Antibodies may be raised against the GCR1 and/or GCR2 polypeptides. In particular, antibodies may be raised against the extracellular domain of GCR1, which is a transmembrane polypeptide.

Antibodies and nucleic acids disclosed here are useful for the identification of PGCs in cell populations. The methods and compositions described here therefore provide a means to isolate PGCs, useful for example for the study of germ tissue development and the generation of transgenic animals, and PGCs when isolated by a method described here.

Homologues of GCR1 and GCR2 may also be used to identify PGCs and other pluripotent cells, such as ES or EG cells.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing. Essential Techniques*, John Wiley & Sons; J. M. Polak and James O'D. McGee, 1990, *In Situ Hybridization: Principles and Practice*; Oxford University Press; M. J. Gait (Editor), 1984, *Oligonucleotide Synthesis: A Practical Approach*, Irl Press; and, D. M. J. Lilley and J. E. Dahlberg, 1992, *Methods of Enzymology: DNA Structure Part A: Synthesis and Physical Analysis of DNA* Methods in Enzymology, Academic Press. Each of these general texts is herein incorporated by reference.

Polypeptides

It will be understood that polypeptide sequences disclosed here are not limited to the particular sequences set forth in SEQ ID NO: 2 and SEQ ID NO: 4, or fragments thereof, or sequences obtained from GCR1 or GCR2 protein, but also include homologous sequences obtained from any source, for example related cellular homologues, homologues from other species and variants or derivatives thereof.

This disclosure therefore encompasses variants, homologues or derivatives of the amino acid sequences set forth in SEQ ID NO: 2 and SEQ ID NO: 4, as well as variants, homologues or derivatives of the amino acid sequences encoded by the nucleotide sequences disclosed here.

Homologues

The polypeptides disclosed include homologous sequences obtained from any source, for example related viral/bacterial proteins, cellular homologues and synthetic peptides, as well as variants or derivatives thereof. Thus polypeptides also include those encoding homologues of GCR1 and/or GCR2 from other species including animals such as mammals (e.g. mice, rats or rabbits), especially primates, more especially humans. More specifically, homologues include human homologues.

In the context of the present document, a homologous sequence or homologue is taken to include an amino acid sequence which is at least 60, 70, 80 or 90% identical, preferably at least 95 or 98% identical at the amino acid level over at least 30, preferably 50, 70, 90 or 100 amino acids with GCR1 or GCR2, for example as shown in the sequence listing herein. In the context of this document, a homologous sequence is taken to include an amino acid sequence which is at least 15, 20, 25, 30, 40, 50, 60, 70, 80 or 90% identical, preferably at least 95 or 98% identical at the amino acid level, preferably over at least 50 or 100, preferably 200, 300, 400 or 500 amino acids with the sequence of GCR1 or GCR2, for example GCR1 (SEQ ID NO: 2) and GCR2 (SEQ ID NO: 4). Although homology can also be considered in terms of similarity (i.e. amino acid residues having similar chemical properties/functions), in the context of the present document it is preferred to express homology in terms of sequence identity.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence directly compared with the corresponding amino acid in the other sequence, one residue at a time. This is called an "ungapped" alignment. Typically, such ungapped alignments are performed only over a relatively short number of residues (for example less than 50 contiguous amino acids).

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package (see below) the default gap penalty for amino acid sequences is −12 for a gap and 4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software than can perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Bestfit program.

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). It is preferred to use the public default values for the GCG package, or in the case of other software, the default matrix, such as BLOSUM62.

Once the software has produced an optimal alignment, it is possible to calculate % homology, preferably % sequence identity. The software typically does this as part of the sequence comparison and generates a numerical result.

Variants and Derivatives

The terms "variant" or "derivative" in relation to the amino acid sequences as described here includes any substitution of, variation of, modification of, replacement of, deletion of or addition of one (or more) amino acids from or to the sequence. Preferably, the resultant amino acid sequence retains substantially the same activity as the unmodified sequence, preferably having at least the same activity as the GCR1 and/or GCR2 polypeptides shown in the sequence listings. Thus, the key feature of the sequences—namely that they are specific for PGCs and other pluripotent cells, such as ES or EG cells, and can serve as a marker for these cells in a cell population— is preferably retained.

Polypeptides having the amino acid sequence shown in the Examples, or fragments or homologues thereof may be modified for use in the methods and compositions described here. Typically, modifications are made that maintain the biological activity of the sequence. Amino acid substitutions may be made, for example from 1, 2 or 3 to 10, 20 or 30 substitutions provided that the modified sequence retains the biological activity of the unmodified sequence. Amino acid substitutions may include the use of non-naturally occurring analogues, for example to increase blood plasma half-life of a therapeutically administered polypeptide.

Natural variants of GCR1 and GCR2 are likely to comprise conservative amino acid substitutions. Conservative substitutions may be defined, for example according to the Table below. Amino acids in the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

Fragments

Polypeptides disclosed here and useful as markers also include fragments of the above mentioned full length polypeptides and variants thereof, including fragments of the sequences set out in SEQ ID NO:2 and SEQ ID NO: 4.

Polypeptides also include fragments of the full length sequence of any of the GCR1 and/or GCR2 polypeptides. Preferably fragments comprise at least one epitope. Methods of identifying epitopes are well known in the art. Fragments will typically comprise at least 6 amino acids, more preferably at least 10, 20, 30, 50 or 100 amino acids.

Included are fragments comprising, preferably consisting of, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145 or 150, or more residues from a GCR1 and/or GCR2 amino acid sequence.

Polypeptide fragments of the GCR proteins and allelic and species variants thereof may contain one or more (e.g. 5, 10, 15, or 20) substitutions, deletions or insertions, including conserved substitutions. Where substitutions, deletion and/or insertions occur, for example in different species, preferably less than 50%, 40% or 20% of the amino acid residues depicted in the sequence listings are altered.

GCR1 and/GCR2, and their fragments, homologues, variants and derivatives, may be made by recombinant means. However, they may also be made by synthetic means using techniques well known to skilled persons such as solid phase synthesis. The proteins may also be produced as fusion proteins, for example to aid in extraction and purification. Examples of fusion protein partners include glutathione-S-transferase (GST), 6×His, GAL4 (DNA binding and/or transcriptional activation domains) and β-galactosidase. It may also be convenient to include a proteolytic cleavage site between the fusion protein partner and the protein sequence of interest to allow removal of fusion protein sequences. Preferably the fusion protein will not hinder the function of the protein of interest sequence. Proteins may also be obtained by purification of cell extracts from animal cells.

The GCR1 and/or GCR2 polypeptides, variants, homologues, fragments and derivatives disclosed here may be in a substantially isolated form. It will be understood that such polypeptides may be mixed with carriers or diluents which will not interfere with the intended purpose of the protein and still be regarded as substantially isolated. A GCR1/GCR2 variant, homologue, fragment or derivative may also be in a substantially purified form, in which case it will generally comprise the protein in a preparation in which more than 90%, e.g. 95%, 98% or 99% of the protein in the preparation is a protein.

The GCR1/GCR2 polypeptides, variants, homologues, fragments and derivatives disclosed here may be labelled with a revealing label. The revealing label may be any suitable label which allows the polypeptide, etc to be detected. Suitable labels include radioisotopes, e.g. $^{125}$I, enzymes, antibodies, polynucleotides and linkers such as biotin. Labelled polypeptides may be used in diagnostic procedures such as immunoassays to determine the amount of a polypeptide in a sample. Polypeptides or labelled polypeptides may also be used in serological or cell-mediated immune assays for the detection of immune reactivity to said polypeptides in animals and humans using standard protocols.

GCR1/GCR2 polypeptides, variants, homologues, fragments and derivatives disclosed here, optionally labelled, my also be fixed to a solid phase, for example the surface of an immunoassay well or dipstick. Such labelled and/or immobilised polypeptides may be packaged into kits in a suitable container along with suitable reagents, controls, instructions and the like. Such polypeptides and kits may be used in methods of detection of antibodies to the polypeptides or their allelic or species variants by immunoassay.

Immunoassay methods are well known in the art and will generally comprise: (a) providing a polypeptide comprising an epitope bindable by an antibody against said protein; (b) incubating a biological sample with said polypeptide under conditions which allow for the formation of an antibody-antigen complex; and (c) determining whether antibody-antigen complex comprising said polypeptide is formed.

The GCR1/GCR2 polypeptides, variants, homologues, fragments and derivatives disclosed here may be used in in vitro or in vivo cell culture systems to study the role of their corresponding genes and homologues thereof in cell function, including their function in disease. For example, truncated or modified polypeptides may be introduced into a cell to disrupt the normal functions which occur in the cell. The polypeptides may be introduced into the cell by in situ expression of the polypeptide from a recombinant expression vector (see below). The expression vector optionally carries an inducible promoter to control the expression of the polypeptide.

The use of appropriate host cells, such as insect cells or mammalian cells, is expected to provide for such post-translational modifications (e.g. myristolation, glycosylation, truncation, lapidation and tyrosine, serine or threonine phosphorylation) as may be needed to confer optimal biological activity on recombinant expression products. Such cell culture systems in which the GCR1/GCR2 polypeptides, variants, homologues, fragments and derivatives disclosed here are expressed may be used in assay systems to identify candidate substances which interfere with or enhance the functions of the polypeptides in the cell.

GCR1/GCR2 Nucleic Acids

The methods and compositions described here provide generally for a number of GCR1 and GCR2 nucleic acids, together with fragments, homologues, variants and derivatives thereof. These nucleic acid sequences preferably encode the polypeptide sequences disclosed here, and particularly in the sequence listings. Preferably, the polynucleotides comprise Stella and/or Fragilis nucleic acids, preferably selected from the group consisting of: SEQ ID NO: 1, 3, 5, 6, 7, 8 or 9, fragments, homologues, variants and derivatives thereof.

In particular, we provide for nucleic acids which encode any of the GCR1 and/or GCR2 polypeptides disclosed here. Thus, the terms "GCR nucleic acid", "GCR1 nucleic acid" and "GCR2 nucleic acid" should be construed accordingly. Preferably, however, such nucleic acids comprise any of the sequences set out as SEQ ID NO: 1, 3, 5, 6, 7, 8 or 9 or a sequence encoding any of the polypeptides SEQ ID NO: 2 and 4, and a fragment, homologue, variant or derivative of such a nucleic acid. The above terms therefore preferably should be taken to refer to these sequences.

As used here in this document, the terms "polynucleotide", "nucleotide", and nucleic acid are intended to be synonymous with each other. "Polynucleotide" generally refers to any polyribonucleotide or polydeoxribonucleotide, which may be unmodified RNA or DNA or modified RNA or DNA. "Polynticleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

It will be understood by a skilled person that numerous different polynucleotides and nucleic acids can encode the same polypeptide as a result of the degeneracy of the genetic code. In addition, it is to be understood that skilled persons may, using routine techniques, make nucleotide substitutions that do not affect the polypeptide sequence encoded by the polynucleotides described here to reflect the codon usage of any particular host organism in which the polypeptides are to be expressed.

Variants, Derivatives and Homologues

The polynucleotides described here may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the present document, it is to be understood that the polynucleotides described herein may be modified by any method available in the art. Such modifications may be carried out in order to enhance the in vivo activity or life span of polynucleotides.

Where the polynucleotide is double-stranded, both strands of the duplex, either individually or in combination, are encompassed by the methods and compositions described here. Where the polynucleotide is single-stranded, it is to be understood that the complementary sequence of that polynucleotide is also included.

The terms "variant", "homologue" or "derivative" in relation to a nucleotide sequence include any substitution of, variation of, modification of, replacement of, deletion of or addition of one (or more) nucleotides from or to the sequence providing the resultant nucleotide sequence is specific for pluripotent cells, preferably specific for PGCs, ES cells or EG cells. Most preferably, the resultant nucleotide sequence is specific for PGCs.

As indicated above, with respect to sequence identity, a "homologue" has preferably at least 5% identity, at least 10% identity, at least 15% identity, at least 20% identity, at least 25% identity, at least 30% identity, at least 35% identity, at least 40% identity, at least 45% identity, at least 50% identity, at least 55% identity, at least 60% identity, at least 65% identity, at least 70% identity, at least 75% identity, at least 80% identity, at least 85% identity, at least 90% identity, or at least 95% identity to the relevant sequence shown in the sequence listings.

More preferably there is at least 95% identity, more preferably at least 96% identity, more preferably at least 97% identity, more preferably at least 98% identity, more preferably at least 99% identity. Nucleotide homology comparisons may be conducted as described above. A preferred sequence comparison program is the GCG Wisconsin Bestfit program described above. The default scoring matrix has a match value of 10 for each identical nucleotide and −9 for each mismatch. The default gap creation penalty is −50 and the default gap extension penalty is −3 for each nucleotide.

Hybridisation

We further describe nucleotide sequences that are capable of hybridising selectively to any of the sequences presented herein, or any variant, fragment or derivative thereof, or to the complement of any of the above. Nucleotide sequences are preferably at least 15 nucleotides in length, more preferably at least 20, 30, 40 or 50 nucleotides in length.

The term "hybridisation" as used herein shall include "the process by which a strand of nucleic acid joins with a complementary strand through base pairing" as well as the process of amplification as carried out in polymerase chain reaction technologies.

Polynucleotides capable of selectively hybridising to the nucleotide sequences presented herein, or to their complement, will be generally at least 70%, preferably at least 80 or 90% and more preferably at least 95% or 98% homologous to the corresponding nucleotide sequences presented herein over a region of at least 20, preferably at least 25 or 30, for instance at least 40, 60 or 100 or more contiguous nucleotides.

The term "selectively hybridisable" means that the polynucleotide used as a probe is used under conditions where a target polynucleotide is found to hybridize to the probe at a level significantly above background. The background hybridization may occur because of other polynucleotides present, for example, in the cDNA or genomic DNA library being screening. In this event, background implies a level of signal generated by interaction between the probe and a non-specific DNA member of the library which is less than 10 fold, preferably less than 100 fold as intense as the specific interaction observed with the target DNA. The intensity of interaction may be measured, for example, by radiolabelling the probe, e.g. with $^{32}$P.

Hybridisation conditions are based on the melting temperature (Tm) of the nucleic acid binding complex, as taught in Berger and Kimmel (1987, Guide to Molecular Cloning Techniques, Methods in Enzymology, Vol 152, Academic Press, San Diego Calif.), and confer a defined "stringency" as explained below.

Maximum stringency typically occurs at about Tm–5° C. (5° C. below the Tm of the probe); high stringency at about 5° C. to 10° C. below Tm; intermediate stringency at about 10° C. to 20° C. below Tm; and low stringency at about 20° C. to 25° C. below Tm. As will be understood by those of skill in the art, a maximum stringency hybridisation can be used to identify or detect identical polynucleotide sequences while an intermediate (or low) stringency hybridisation can be used to identify or detect similar or related polynucleotide sequences.

In a preferred aspect, we disclose nucleotide sequences that can hybridise to a GCR1/GCR2 nucleic acid, or a fragment, homologue, variant or derivative thereof, under stringent conditions (e.g. 65° C. and 0.1×SSC {1×SSC=0.15 M NaCl, 0.015 M Na$_3$ Citrate pH 7.0}).

Where a polynucleotide is double-stranded, both strands of the duplex, either individually or in combination, are encompassed by the present disclosure. Where the polynucleotide is single-stranded, it is to be understood that the complementary sequence of that polynucleotide is also disclosed and encompassed.

Polynucleotides which are not 100% homologous to the sequences disclosed here but fall within the disclosure can be obtained in a number of ways. Other variants of the sequences described herein may be obtained for example by probing DNA libraries made from a range of individuals, for example individuals from different populations. In addition, other viral/bacterial, or cellular homologues particularly cellular homologues found in mammalian cells (e.g. rat, mouse, bovine and primate cells, including human cells), may be obtained and such homologues and fragments thereof in general will be capable of selectively hybridising to the sequences shown in the sequence listing herein. Such sequences may be obtained by probing cDNA libraries made from or genomic DNA libraries from other animal species, and probing such libraries with probes comprising all or part of SEQ ID NOs: 1 or 3 under conditions of medium to high stringency. Similar considerations apply to obtaining species homologues and allelic variants of GCR1 and GCR2.

The polynucleotides described here may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides as used herein. Preferred fragments are less than 500, 200, 100, 50 or 20 nucleotides in length.

Polynucleotides such as a DNA polynucleotides and probes may be produced recombinantly, synthetically, or by any means available to those of skill in the art. They may also be cloned by standard techniques.

In general, primers will be produced by synthetic means, involving a step wise manufacture of the desired nucleic acid sequence one nucleotide at a time. Techniques for accomplishing this using automated techniques are readily available in the art.

Longer polynucleotides will generally be produced using recombinant means, for example using PCR (polymerase chain reaction) cloning techniques. This will involve making a pair of primers (e.g. of about 15 to 30 nucleotides) flanking a region of the sequence which it is desired to clone, bringing the primers into contact with mRNA or cDNA obtained from an animal or human cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector Nucleotide Vectors The polynucleotides can be incorporated into a recombinant replicable vector. The vector may be used to replicate the nucleic acid in a compatible host cell. Thus in a further embodiment, we provide a method of making polynucleotides by introducing a polynucleotide into a replicable vector, introducing the vector into a compatible host cell, and growing the host cell under conditions which bring about replication of the vector. The vector may be recovered from the host cell. Suitable host cells include bacteria such as *E. coli*, yeast, mammalian cell lines and other eukaryotic cell lines, for example insect Sf9 cells.

Preferably, a polynucleotide in a vector is operably linked to a control sequence that is capable of providing for the expression of the coding sequence by the host cell, i.e. the vector is an expression vector. The term "operably linked" means that the components described are in a relationship permitting them to function in their intended manner. A regulatory sequence "operably linked" to a coding sequence is ligated in such a way that expression of the coding sequence is achieved under condition compatible with the control sequences.

The control sequences may be modified, for example by the addition of further transcriptional regulatory elements to make the level of transcription directed by the control sequences more responsive to transcriptional modulators.

Vectors may be transformed or transfected into a suitable host cell as described below to provide for expression of a protein. This process may comprise culturing a host cell transformed with an expression vector as described above under conditions to provide for expression by the vector of a coding sequence encoding the protein, and optionally recovering the expressed protein.

The vectors may be for example, plasmid or virus vectors provided with an origin of replication, optionally a promoter for the expression of the said polynucleotide and optionally a regulator of the promoter. The vectors may contain one or more selectable marker genes, for example an ampicillin resistance gene in the case of a bacterial plasmid or a neomycin resistance gene for a mammalian vector. Vectors may be used, for example, to transfect or transform a host cell.

Control sequences operably linked to sequences encoding the protein include promoters/enhancers and other expression regulation signals. These control sequences may be selected to be compatible with the host cell for which the expression vector is designed to be used in. The term "promoter" is well-known in the art and encompasses nucleic acid regions ranging in size and complexity from minimal promoters to promoters including upstream elements and enhancers.

The promoter is typically selected from promoters which are functional in mammalian cells, although prokaryotic promoters and promoters functional in other eukaryotic cells may be used. The promoter is typically derived from promoter sequences of viral or eukaryotic genes. For example, it may be a promoter derived from the genome of a cell in which expression is to occur. With respect to eukaryotic promoters, they may be promoters that function in a ubiquitous manner (such as promoters of α-actin, β-actin, tubulin) or, alternatively, a tissue-specific manner (such as promoters of the genes for pyruvate kinase). They may also be promoters that respond to specific stimuli, for example promoters that bind steroid hormone receptors. Viral promoters may also be used, for example the Moloney murine leukaemia virus long terminal repeat (MMLV LTR) promoter, the Rous sarcoma virus (RSV) LTR promoter or the human cytomegalovirus (CMV) IE promoter.

It may also be advantageous for the promoters to be inducible so that the levels of expression of the heterologous gene can be regulated during the life-time of the cell. Inducible means that the levels of expression obtained using the promoter can be regulated.

In addition, any of these promoters may be modified by the addition of further regulatory sequences, for example enhancer sequences. Chimeric promoters may also be used comprising sequence elements from two or more different promoters described above.

Host Cells

Vectors and polynucleotides disclosed here may be introduced into host cells for the purpose of replicating the vectors/polynucleotides and/or expressing the proteins. Although the proteins may be produced using prokaryotic cells as host cells, it is preferred to use eukaryotic cells, for example yeast, insect or mammalian cells, in particular mammalian cells.

Vectors/polynucleotides may introduced into suitable host cells using a variety of techniques known in the art, such as transfection, transformation and electroporation. Where vectors/polynucleotides as disclosed here are to be administered to animals, several techniques are known in the art, for example infection with recombinant viral vectors such as retroviruses, herpes simplex viruses and adenoviruses, direct injection of nucleic acids and biolistic transformation.

Protein Expression and Purification

Host cells comprising polynucleotides disclosed here may be used to express proteins. Host cells may be cultured under suitable conditions which allow expression of the proteins. Expression of the proteins described here may be constitutive such that they are continually produced, or inducible, requiring a stimulus to initiate expression. In the case of inducible expression, protein production can be initiated when required by, for example, addition of an inducer substance to the culture medium, for example dexamethasone or IPTG.

Proteins can be extracted from host cells by a variety of techniques known in the art, including enzymatic, chemical and/or osmotic lysis and physical disruption.

Recombinant Stella and Fragilis Proteins

Nucletide sequences of Stella and Fragilis are cloned into a TRI-system vector (Qiagen). Stella sequence comprising the second codon onwards (i.e., an N terminal fragment of Stella without the first ATG codon) is cloned into a pQE vector using appropriate restriction enzyme sites, and according to the manufacturers instructions. QIAexpress pQE vectors enable high-level expression of 6×His-tagged proteins in E. coli.

A His tag is placed in the N terminal portion of the Stella gene. Recombinant protein is purified by affinity chromatography on a Ni-NTA column, according to manufacturer's instructions. The His tag is cleaved using a suitable protease.

Recombinantly expressed Stella and Fragilis protein are found to be biologically active.

Transgenic Animals

We further describe transgenic animals capable of expressing natural or recombinant Stella and/or Fragilis, or a homologue, variant or derivative, at elevated or reduced levels compared to the normal expression level. Included are transgenic animals ("Stella knockout"s or "Fragilis knockout"s) which do not express functional Stella and/or Fragilis, as the case may be. The Stella and Fragilis knockouts may arise as a result of functional disruption of the Stella and/or Fragilis gene or any portion of that gene, including one or more loss of function mutations, including a deletion or replacement, of the Stella and/or Fragilis gene. The mutations include single point mutations, and may target coding or non-coding regions of Stella and/or Fragilis.

Preferably, such a transgenic animal is a non-human mammal, such as a pig, a sheep or a rodent. Most preferably the transgenic animal is a mouse or a rat. Such transgenic animals may be used in screening procedures to identify agonists and/or antagonists of Stella and/or Fragilis, as well as to test for their efficacy as treatments for diseases in vivo.

Mice which are null for Stella and/or Fragilis may be used for various purposes. For example, transgenic animals that have been engineered to be deficient in the production of Stella and/or Fragilis may be used in assays to identify agonists and/or antagonists of Stella and/or Fragilis. One assay is designed to evaluate a potential drug (aa candidate ligand or compound) to determine if it produces a physiological response in the absence Stella and/or Fragilis. This may be accomplished by administering the drug to a transgenic animal as discussed above, and then assaying the animal for a particular response.

Tissues derived from the Stella and/or Fragilis knockout animals may be used in binding assays to determine whether the potential drug (a candidate ligand or compound) binds to Stella or Fragilis, as the case may be. Such assays can be conducted by obtaining a first Stella and/or Fragilis preparation from the transgenic animal engineered to be deficient in Stella and/or Fragilis production and a second Stella and/or Fragilis preparation from a source known to bind any identified ligands or compounds. In general, the first and second preparations will be similar in all respects except for the source from which they are obtained. For example, if brain tissue from a transgenic animal (such as described above and below) is used in an assay, comparable brain tissue from a normal (wild type) animal is used as the source of the second preparation. Each of the preparations is incubated with a ligand known to bind to Stella and/or Fragilis, both alone and in the presence of the candidate ligand or compound. Preferably, the candidate ligand or compound will be examined at several different concentrations.

The extent to which binding by the known ligand is displaced by the test compound is determined for both the first and second preparations. Tissues derived from transgenic animals may be used in assays directly or the tissues may be processed to isolate Stella and/or Fragilis proteins, which are themselves used in the assays. A preferred transgenic animal is the mouse. The ligand may be labeled using any means compatible with binding assays. This would include, without limitation, radioactive, enzymatic, fluorescent or chemiluminescent labeling (as well as other labelling techniques as described in further detail above).

Furthermore, antagonists of Stella and/or Fragilis may be identified by administering candidate compounds, etc, to wild type animals expressing functional Stella and/or Fragilis, and animals identified which exhibit any of the phenotypic characteristics associated with reduced or abolished expression of Stella and/or Fragilis function.

Methods for generating non-human transgenic animal are known in the art, and are described in further detail in the Examples below. Transgenic gene constructs can be introduced into the germ line of an animal to make a transgenic mammal. For example, one or several copies of the construct may be incorporated into the genome of a mammalian embryo by standard transgenic techniques.

In an exemplary embodiment, the transgenic non-human animals described here are produced by introducing transgenes into the germline of the non-human animal. Embryonal target cells at various developmental stages can be used to introduce transgenes. Different methods are used depending on the stage of development of the embryonal target cell. The specific line(s) of any animal used to produce transgenic animals are selected for general good health, good embryo yields, good pronuclear visibility in the embryo, and good reproductive fitness. In addition, the haplotype is a significant factor.

Introduction of the transgene into the embryo can be accomplished by any means known in the art such as, for example, microinjection, electroporation, or lipofection. For example, the Stella or Fragilis transgene can be introduced into a mammal by microinjection of the construct into the pronuclei of the fertilized mammalian egg(s) to cause one or more copies of the construct to be retained in the cells of the developing mammal(s). Following introduction of the transgene construct into the fertilized egg, the egg may be incubated in vitro for varying amounts of time, or reimplanted into the surrogate host, or both. In vitro incubation to maturity is also included. One common method in to incubate the embryos in vitro for about 1-7 days, depending on the species, and then reimplant them into the surrogate host.

The progeny of the transgenically manipulated embryos can be tested for the presence of the construct by Southern blot analysis of the segment of tissue. If one or more copies of the exogenous cloned construct remains stably integrated into the genome of such transgenic embryos, it is possible to establish permanent transgenic mammal lines carrying the transgenically added construct.

The litters of transgenically altered mammals can be assayed after birth for the incorporation of the construct into the genome of the offspring. Preferably, this assay is accomplished by hybridizing a probe corresponding to the DNA sequence coding for the desired recombinant protein product or a segment thereof onto chromosomal material from the progeny. Those mammalian progeny found to contain at least one copy of the construct in their genome are grown to maturity.

For the purposes of this document, a zygote is essentially the formation of a diploid cell which is capable of developing into a complete organism. Generally, the zygote will be comprised of an egg containing a nucleus formed, either naturally or artificially, by the fusion of two haploid nuclei from a gamete or gametes. Thus, the gamete nuclei must be ones which are naturally compatible, i.e., ones which result in a viable zygote capable of undergoing differentiation and developing into a functioning organism. Generally, a euploid zygote is preferred. If an aneuploid zygote is obtained, then the number of chromosomes should not vary by more than one with respect to the euploid number of the organism from which either gamete originated.

In addition to similar biological considerations, physical ones also govern the amount (e.g., volume) of exogenous genetic material which can be added to the nucleus of the zygote or to the genetic material which forms a part of the zygote nucleus. If no genetic material is removed, then the amount of exogenous genetic material which can be added is limited by the amount which will be absorbed without being physically disruptive. Generally, the volume of exogenous genetic material inserted will not exceed about 10 picoliters. The physical effects of addition must not be so great as to physically destroy the viability of the zygote. The biological limit of the number and variety of DNA sequences will vary depending upon the particular zygote and functions of the exogenous genetic material and will be readily apparent to one skilled in the art, because the genetic material, including the exogenous genetic material, of the resulting zygote must be biologically capable of initiating and maintaining the differentiation and development of the zygote into a functional organism.

The number of copies of the transgene constructs which are added to the zygote is dependent upon the total amount of exogenous genetic material added and will be the amount which enables the genetic transformation to occur. Theoretically only one copy is required; however, generally, numerous copies are utilized, for example, 1,000-20,000 copies of the transgene construct, in order to insure that one copy is functional. There will often be an advantage to having more than one functioning copy of each of the inserted exogenous DNA sequences to enhance the phenotypic expression of the exogenous DNA sequences.

Any technique which allows for the addition of the exogenous genetic material into nucleic genetic material can be utilized so long as it is not destructive to the cell, nuclear membrane or other existing cellular or genetic structures. The exogenous genetic material is preferentially inserted into the nucleic genetic material by microinjection. Microinjection of cells and cellular structures is known and is used in the art.

Reimplantation is accomplished using standard methods. Usually, the surrogate host is anesthetized, and the embryos are inserted into the oviduct. The number of embryos implanted into a particular host will vary by species, but will usually be comparable to the number of off spring the species naturally produces.

Transgenic offspring of the surrogate host may be screened for the presence and/or expression of the transgene by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically, DNA is prepared from tail tissue and analyzed by Southern analysis or PCR for the transgene. Alternatively, the tissues or cells believed to express the transgene at the highest levels are tested for the presence and expression of the transgene using Southern analysis or PCR, although any tissues or cell types may be used for this analysis.

Alternative or additional methods for evaluating the presence of the transgene include, without limitation, suitable biochemical assays such as enzyme and/or immunological assays, histological stains for particular marker or enzyme activities, flow cytometric analysis, and the like. Analysis of the blood may also be useful to detect the presence of the transgene product in the blood, as well as to evaluate the effect of the transgene on the levels of various types of blood cells and other blood constituents.

Progeny of the transgenic animals may be obtained by mating the transgenic animal with a suitable partner, or by in vitro fertilization of eggs and/or sperm obtained from the transgenic animal. Where mating with a partner is to be performed, the partner may or may not be transgenic and/or a knockout; where it is transgenic, it may contain the same or a different transgene, or both. Alternatively, the partner may be a parental line. Where in vitro fertilization is used, the fertilized embryo may be implanted into a surrogate host or incubated in vitro, or both. Using either method, the progeny may be evaluated for the presence of the transgene using methods described above, or other appropriate methods.

The transgenic animals produced in accordance the methods described here will include exogenous genetic material. As set out above, the exogenous genetic material will, in certain embodiments, be a DNA sequence which results in the production of a Stella and/or Fragilis protein. Further, in such embodiments the sequence will be attached to a transcriptional control element, e.g., a promoter, which preferably allows the expression of the transgene product in a specific type of cell.

It will be appreciated that it is possible to manipulate the control elements (promoters or enhancers) to regulate the spatial or temporal expression, or both, of Stella or Fragilis (as the case may be). For example, specific control elements may be deleted from the endogenous Stella and/or Fragilis locus so that expression is restricted to only certain tissues. Alternatively, it is possible to prepare transgenes which only contain one, some, or more, of the control elements. Transgenic animals made this way for Stella and/or Fragilis and having properties of ectopic expression, temporally or spatially, or both, will be useful for investigation of Stella and/or Fragilis gene function.

Retroviral infection can also be used to introduce transgene into a non-human animal. The developing non-human embryo can be cultured in vitro to the blastocyst stage. During this time, the blastomeres can be targets for retroviral infection (Jaenich, R. (1976) PNAS 73:1260-1264). Efficient infection of the blastomeres is obtained by enzymatic treatment to remove the zona pellucida (Manipulating the Mouse Embryo, Hogan eds. (Cold Spring Harbor Laboratory Press, Cold Spring Harbor, 1986). The viral vector system used to introduce the transgene is typically a replication-defective retrovirus carrying the transgene (Jahner et al. (1985) PNAS 82:6927-6931; Van der Putten et al. (1985) PNAS 82:6148-6152). Transfection is easily and efficiently obtained by culturing the blastomeres on a monolayer of virus-producing cells (Van der Putten, supra; Stewart et al. (1987) EMBO J. 6:383-388). Alternatively, infection can be performed at a later stage. Virus or virus-producing cells can be injected into the blastocoele (Jahner et al. (1982) Nature 298:623-628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

A third type of target cell for transgene introduction is the embryonal stem cell (ES). ES cells are obtained from pre-implantation embryos cultured in vitro and fused with embryos (Evans et al. (1981) Nature 292:154-156; Bradley et al. (1984) Nature 309:255-258; Gossler et al. (1986) PNAS 83: 9065-9069; and Robertson et al. (1986) Nature 322:445-448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) Science 240:1468-1474.

We also provide non-human transgenic animals, where the transgenic animal is characterized by having an altered Stella and/or Fragilis gene, preferably as described above, as models for Stella or Fragilis function, as the case may be. Alterations to the gene include deletions or other loss of function mutations, introduction of an exogenous gene having a nucleotide sequence with targeted or random mutations, introduction of an exogenous gene from another species, or a combination thereof. The transgenic animals may be either homozygous or heterozygous for the alteration. The animals and cells derived therefrom are useful for screening biologically active agents that may modulate Stella and/or Fragilis function. The screening methods are of particular use for determining the specificity and action of potential therapies for Stella and/or Fragilis associated diseases, as described above. The animals are useful as a model to investigate the role of Stella and/or Fragilis proteins in the body.

Another aspect pertains to a transgenic animal having a functionally disrupted endogenous Stella or Fragilis gene, or both, but which also carries in its genome, and expresses, a transgene encoding a heterologous Stella and/or Fragilis protein (i.e., a Stella and/or Fragilis gene from another species). Preferably, the animal is a mouse and the heterologous Stella or Fragilis is a human Stella or Fragilis. An animal, or cell lines derived from such an animal, which has been reconstituted with human Stella and/or Fragilis, can be used to identify agents that inhibit human Stella and/or Fragilis in vivo and in vitro. For example, a stimulus that induces signalling through human Stella and/or Fragilis can be administered to the animal, or cell line, in the presence and absence of an agent to be tested and the response in the animal, or cell line, can be measured. An agent that inhibits human Stella and/or Fragilis in vivo or in vitro can be identified based upon a decreased response in the presence of the agent compared to the response in the absence of the agent.

We also provide for a Stella and/or Fragilis deficient transgenic non-human animal (a "Stella/Fragilis knock-out" or a "Stella/Fragilis null"). Such an animal is one which expresses lowered or no Stella/Fragilis activity, preferably as a result of an endogenous Stella or Fragilis (as the case may be) genomic sequence being disrupted or deleted. The endogenous Stella or Fragilis genomic sequence may be replaced by a null allele, which may comprise non-functional portions of the wild-type Stella/Fragilis sequence. For example, the endogenous Stella/Fragilis genomic sequence may be replaced by an allele of Stella/Fragilis comprising a disrupting sequence which may comprise heterologous sequences, for example, reporter sequences and/or selectable markers. Preferably, the endogenous Stella/Fragilis genomic sequence in a Stella/Fragilis knock-out mouse is replaced by an allele of Stella or Fragilis in which one or more, preferably all, of the coding sequences is replaced by such a disrupting sequence, preferably a lacZ sequence and a neomycin resistance sequence. Preferably, the genomic Stella/Fragilis sequence which is functionally disrupted comprises a mouse Stella/Fragilis genomic sequence.

Preferably, such an animal expresses no Stella or Fragilis activity, or both. More preferably, the animal expresses no activity of the Stella or Fragilis proteins shown in the sequence listings. Stella/Fragilis knock-outs may be generated by various means known in the art, as described in further detail below. A specific description of the construction of a Stella knock-out mouse is disclosed in Example 20 et seq below.

We further disclose a nucleic acid construct for functionally disrupting a Stella/Fragilis gene in a host cell. The nucleic acid construct comprises: a) a non-homologous replacement portion; b) a first homology region located upstream of the non-homologous replacement portion, the first homology region having a nucleotide sequence with substantial identity to a first Stella/Fragilis gene sequence; and c) a second homology region located downstream of the non-homologous replacement portion, the second homology region having a nucleotide sequence with substantial identity to a second Stella/Fragilis gene sequence, the second Stella/Fragilis gene sequence having a location downstream of the first Stella/Fragilis gene sequence in a naturally occurring endogenous Stella/Fragilis gene. Additionally, the first and second homology regions are of sufficient length for homologous recombination between the nucleic acid construct and an endogenous Stella/Fragilis gene in a host cell when the nucleic acid molecule is introduced into the host cell. In a preferred embodiment, the non-homologous replacement portion comprises an expression reporter, preferably including lacZ and a positive selection expression cassette, preferably including a neomycin phosphotransferase gene operatively linked to a regulatory element(s).

Another aspect pertains to recombinant vectors into which the nucleic acid construct described above has been incorporated. Yet another aspect pertains to host cells into which the nucleic acid construct has been introduced to thereby allow homologous recombination between the nucleic acid construct and an endogenous Stella/Fragilis gene of the host cell, resulting in functional disruption of the endogenous Stella/Fragilis gene. The host cell can be a mammalian cell that normally expresses Stella/Fragilis from the liver, brain, spleen or heart, or a pluripotent cell, such as a mouse embryonic stem cell. Further development of an embryonic stem cell into which the nucleic acid construct has been introduced and homologously recombined with the endogenous Stella/Fragilis gene produces a transgenic nonhuman animal having cells that are descendant from the embryonic stem cell and thus carry the Stella/Fragilis gene disruption in their genome. Animals that carry the Stella/Fragilis gene disruption in their germline can then be selected and bred to produce animals having the Stella/Fragilis gene disruption in all somatic and germ cells. Such mice can then be bred to homozygosity for the Stella/Fragilis gene disruption.

Antibodies

Antibodies, as used herein, refers to complete antibodies or antibody fragments capable of binding to a selected target, and including Fv, ScFv, Fab' and F(ab')$_2$, monoclonal and polyclonal antibodies, engineered antibodies including chimeric, CDR-grafted and humanised antibodies, and artificially selected antibodies produced using phage display or alternative techniques. Small fragments, such as Fv and ScFv, possess advantageous properties for diagnostic and therapeutic applications on account of their small size and consequent superior tissue distribution.

The antibodies according described here are especially indicated for the detection of PGCs and other pluripotent cells, such as ES or EG cells. Accordingly, they may be altered antibodies comprising an effector protein such as a label. Especially preferred are labels which allow the imaging of the distribution of the antibody in vivo or in vitro. Such labels may be radioactive labels or radioopaque labels, such as metal particles, which are readily visualisable within an embryo or a cell mass. Moreover, they may be fluorescent labels or other labels which are visualisable on tissue samples.

Recombinant DNA technology may be used to improve the antibodies as described here. Thus, chimeric antibodies may be constructed in order to decrease the immunogenicity thereof in diagnostic or therapeutic applications. Moreover, immunogenicity may be minimised by humanising the antibodies by CDR grafting [see European Patent Application 0 239 400 (Winter)] and, optionally, framework modification [EP 0 239 400].

Antibodies may be obtained from animal serum, or, in the case of monoclonal antibodies or fragments thereof, produced in cell culture. Recombinant DNA technology may be used to produce the antibodies according to established procedure, in bacterial or preferably mammalian cell culture. The selected cell culture system preferably secretes the antibody product.

Therefore, we disclose a process for the production of an antibody comprising culturing a host, e.g. *E. coli* or a mammalian cell, which has been transformed with a hybrid vector comprising an expression cassette comprising a promoter operably linked to a first DNA sequence encoding a signal peptide linked in the proper reading frame to a second DNA sequence encoding said antibody protein, and isolating said protein.

Multiplication of hybridoma cells or mammalian host cells in vitro is carried out in suitable culture media, which are the customary standard culture media, for example Dulbecco's Modified Eagle Medium (DMEM) or RPMI 1640 medium, optionally replenished by a mammalian serum, e.g. foetal calf serum, or trace elements and growth sustaining supplements, e.g. feeder cells such as normal mouse peritoneal exudate cells, spleen cells, bone marrow macrophages, 2-aminoethanol, insulin, transferrin, low density lipoprotein, oleic acid, or the like. Multiplication of host cells which are bacterial cells or yeast cells is likewise carried out in suitable culture media known in the art, for example for bacteria in medium LB, NZCYM, NZYM, NZM, Terrific Broth, SOB, SOC, 2×YT, or M9 Minimal Medium, and for yeast in medium YPD, YEPD, Minimal Medium, or Complete Minimal Dropout Medium.

In vitro production provides relatively pure antibody preparations and allows scale-up to give large amounts of the desired antibodies. Techniques for bacterial cell, yeast or mammalian cell cultivation are known in the art and include homogeneous suspension culture, e.g. in an airlift reactor or in a continuous stirrer reactor, or immobilised or entrapped cell culture, e.g. in hollow fibres, microcapsules, on agarose microbeads or ceramic cartridges.

Large quantities of the desired antibodies can also be obtained by multiplying mammalian cells in vivo. For this purpose, hybridoma cells producing the desired antibodies are injected into histocompatible mammals to cause growth of antibody-producing tumours. Optionally, the animals are primed with a hydrocarbon, especially mineral oils such as pristane (tetramethyl-pentadecane), prior to the injection. After one to three weeks, the antibodies are isolated from the body-fluids of those mammals. For example, hybridoma cells obtained by fusion of suitable myeloma cells with antibody-producing spleen cells from Balb/c mice, or transfected cells derived from hybridoma cell line Sp2/0 that produce the desired antibodies are injected intraperitoneally into Balb/c mice optionally pre-treated with pristane, and, after one to two weeks, ascitic fluid is taken from the animals.

The foregoing, and other, techniques are discussed in, for example, Kohler and Milstein, (1975) Nature 256:495-497; U.S. Pat. No. 4,376,110; Harlow and Lane, Antibodies: a Laboratory Manual, (1988) Cold Spring Harbor, incorporated herein by reference. Techniques for the preparation of recombinant antibody molecules is described in the above references and also in, for example, EP 0623679; EP 0368684 and EP 0436597, which are incorporated herein by reference.

The cell culture supernatants are screened for the desired antibodies, preferentially by immunofluorescent staining of PGCs or other pluripotent cells, such as ES or EG cells, by immunoblotting, by an enzyme immunoassay, e.g. a sandwich assay or a dot-assay, or a radioimmunoassay.

For isolation of the antibodies, the immunoglobulins in the culture supernatants or in the ascitic fluid may be concentrated, e.g. by precipitation with ammonium sulphate, dialysis against hygroscopic material such as polyethylene glycol, filtration through selective membranes, or the like. If necessary and/or desired, the antibodies are purified by the customary chromatography methods, for example gel filtration, ion-exchange chromatography, chromatography over DEAE-cellulose and/or (immuno-) affinity chromatography, e.g. affinity chromatography with GCR1 or GCR2, or fragments thereof, or with Protein-A.

Hybridoma cells secreting the monoclonal antibodies are also provided. Preferred hybridoma cells are genetically stable, secrete monoclonal antibodies of the desired specificity and can be activated from deep-frozen cultures by thawing and recloning.

Also included is a process for the preparation of a hybridoma cell line secreting monoclonal antibodies directed to GCR1 and/or GCR2, characterised in that a suitable mammal, for example a Balb/c mouse, is immunised with a one or more GCR1 or GCR2 polypeptides, or antigenic fragments thereof; antibody-producing cells of the immunised mammal are fused with cells of a suitable myeloma cell line, the hybrid cells obtained in the fusion are cloned, and cell clones secreting the desired antibodies are selected. For example spleen cells of Balb/c mice immunised with GCR1 and/or GCR2 are fused with cells of the myeloma cell line PAI or the myeloma cell line Sp2/0-Ag14, the obtained hybrid cells are screened for secretion of the desired antibodies, and positive hybridoma cells are cloned.

Preferred is a process for the preparation of a hybridoma cell line, characterised in that Balb/c mice are immunised by injecting subcutaneously and/or intraperitoneally between 10 and $10^7$ and $10^8$ cells expressing GCR1 and/or GCR2 and a suitable adjuvant several times, e.g. four to six times, over several months, e.g. between two and four months, and spleen cells from the immunised mice are taken two to four days after the last injection and fused with cells of the myeloma cell line PAI in the presence of a fusion promoter, preferably polyethylene glycol. Preferably the myeloma cells are fused with a three- to twentyfold excess of spleen cells from the immunised mice in a solution containing about 30% to about 50% polyethylene glycol of a molecular weight around 4000. After the fusion the cells are expanded in suitable culture media as described hereinbefore, supplemented with a selection medium, for example HAT medium, at regular intervals in order to prevent normal myeloma cells from overgrowing the desired hybridoma cells.

Recombinant DNAs comprising an insert coding for a heavy chain variable domain and/or for a light chain variable domain of antibodies directed to GCR1 and/or GCR2 as described hereinbefore are also disclosed. By definition such DNAs comprise coding single stranded DNAs, double stranded DNAs consisting of said coding DNAs and of complementary DNAs thereto, or these complementary (single stranded) DNAs themselves.

Furthermore, DNA encoding a heavy chain variable domain and/or for a light chain variable domain of antibodies directed to GCR1 and/or GCR2 can be enzymatically or chemically synthesised DNA having the authentic DNA sequence coding for a heavy chain variable domain and/or for the light chain variable domain, or a mutant thereof. A mutant of the authentic DNA is a DNA encoding a heavy chain variable domain and/or a light chain variable domain of the above-mentioned antibodies in which one or more amino acids are deleted or exchanged with one or more other amino acids. Preferably said modification(s) are outside the CDRs of the heavy chain variable domain and/or of the light chain variable domain of the antibody. Such a mutant DNA is also intended to be a silent mutant wherein one or more nucleotides are replaced by other nucleotides with the new codons coding for the same amino acid(s). Such a mutant sequence is also a degenerated sequence. Degenerated sequences are degenerated within the meaning of the genetic code in that an unlimited number of nucleotides are replaced by other nucleotides without resulting in a change of the amino acid sequence originally encoded. Such degenerated sequences may be useful due to their different restriction sites and/or frequency of particular codons which are preferred by the specific host, particularly *E. coli*, to obtain an optimal expression of the heavy chain murine variable domain and/or a light chain murine variable domain.

The term mutant is intended to include a DNA mutant obtained by in vitro mutagenesis of the authentic DNA according to methods known in the art.

For the assembly of complete tetrameric immunoglobulin molecules and the expression of chimeric antibodies, the recombinant DNA inserts coding for heavy and light chain variable domains are fused with the corresponding DNAs coding for heavy and light chain constant domains, then transferred into appropriate host cells, for example after incorporation into hybrid vectors.

Also disclosed are recombinant DNAs comprising an insert coding for a heavy chain murine variable domain of an antibody directed to GCR1 and/or GCR2 fused to a human constant domain g, for example γ1, γ2, γ3 or γ4, preferably γ1 or γ4. Likewise we also describe recombinant DNAs comprising an insert coding for a light chain murine variable domain of an antibody directed to GCR1 and/or GCR2 fused to a human constant domain κ or λ, preferably κ.

In another embodiment, we disclose recombinant DNAs coding for a recombinant polypeptide wherein the heavy chain variable domain and the light chain variable domain are linked by way of a spacer group, optionally comprising a signal sequence facilitating the processing of the antibody in the host cell and/or a DNA coding for a peptide facilitating the purification of the antibody and/or a cleavage site and/or a peptide spacer and/or an effector molecule.

The DNA coding for an effector molecule is intended to be a DNA coding for the effector molecules useful in diagnostic or therapeutic applications. Thus, effector molecules which are toxins or enzymes, especially enzymes capable of catalysing the activation of prodrugs, are particularly indicated. The DNA encoding such an effector molecule has the sequence of a naturally occurring enzyme or toxin encoding DNA, or a mutant thereof, and can be prepared by methods well known in the art.

Anti-Peptide Stella and Fragilis Antibodies

Anti-peptide antibodies are produced against Stella and Fragilis peptide sequences. The sequences chosen are as follow:

```
GCR1 (Fragilis):
ASGGQPPNYERLIKEEYE (SEQ ID NO: 10)
and
RDRKMVGDVTGAQAYA (SEQ ID NO: 11)
```

```
        -continued
GCR2 (Stella):
MEEPSEKVDPMKDPET (SEQ ID NO: 12)
and
CHYQRWDPSENAKIGKN (SEQ ID NO: 13)
```

Antibodies are produced by injection into rabbits, and other conventional means, as described in for example, Harlow and Lane (supra).

Antibodies are checked by Elisa assay and by Western blotting, and used for immunostaining as described in the Examples.

Detection of Pluripotent Cells in Cell Populations

Polynucleotide probes or antibodies as described here may be used for the detection of pluripotent cells such as primordial germ cells (PGCs), stem cells such as embryonic stem (ES) and embryonic germ (EG) cells in cell populations. As used herein, a "cell population" is any collection of cells which may contain one or more PGCs, ES or EG cells. Preferably, the collection of cells does not consist solely of PGCs, but comprises at least one other cell type.

Cell populations comprise embryos and embryo tissue, but also adult tissues and tissues grown in culture and cell preparations derived from any of the foregoing.

Polynucleotides as described here may be used for detection of GCR1 and GCR2 transcripts in PGCs or other pluripotent cells, such as ES or EG cells, by nucleic acid hybridisation techniques. Such techniques include PCR, in which primers are hybridised to GCR1 and/or GCR2 transcripts and used to amplify the transcripts, to provide a detectable signal; and hybridisation of labelled probes, in which probes specific for an unique sequence in the GCR1 and/or GCR2 transcript are used to detect the transcript in the target cells.

As noted hereinbefore, probes may be labelled with radioactive, radioopaque, fluorescent or other labels, as is known in the art.

The antibodies may also be used to detect GCR1 and/or GCR2. GRC1, in particular, possesses an extracellular domain which may be targeted by an anti-GCR1 antibody and detected at the cell surface. Alternatively, intracellular scFv may be used to detect GCR1 and/or GCR2 within the cell.

Particularly indicated are immunostaining and FACS techniques. Suitable fluorophores are known in the art, and include chemical fluorophores and fluorescent polypeptides, such as GFP and mutants thereof (see WO 97/28261). Chemical fluorophores may be attached to immunoglobulin molecules by incorporating binding sites therefor into the immunoglobulin molecule during the synthesis thereof.

Preferably, the fluorophore is a fluorescent protein, which is advantageously GFP or a mutant thereof. GFP and its mutants may be synthesised together with the immunoglobulin or target molecule by expression therewith as a fusion polypeptide, according to methods well known in the art. For example, a transcription unit may be constructed as an in-frame fusion of the desired GFP and the immunoglobulin or target, and inserted into a vector as described above, using conventional PCR cloning and ligation techniques.

Antibodies may be labelled with any label capable of generating a signal. The signal may be any detectable signal, such as the induction of the expression of a detectable gene product. Examples of detectable gene products include bioluminescent polypeptides, such as luciferase and GFP, polypeptides detectable by specific assays, such as β-galactosidase and CAT, and polypeptides which modulate the growth characteristics of the host cell, such as enzymes required for metabolism such as HIS3, or antibiotic resistance genes such as G418. In a preferred aspect, the signal is detectable at the cell surface. For example, the signal may be a luminescent or fluorescent signal, which is detectable from outside the cell and allows cell sorting by FACS or other optical sorting techniques.

Preferred is the use of optical immunosensor technology, based on optical detection of fluorescently-labelled antibodies. Immunosensors are biochemical detectors comprising an antigen or antibody species coupled to a signal transducer which detects the binding of the complementary species (Rabbany et al., 1994 *Crit Rev Biomed Eng* 22:307-346; Morgan et al., 1996 *Clin Chem* 42:193-209). Examples of such complementary species include the antigen Zif 268 and the anti-Zif 268 antibody. Immunosensors produce a quantitative measure of the amount of antibody, antigen or hapten present in a complex sample such as serum or whole blood (Robinson 1991 *Biosens Bioelectron* 6:183-191). The sensitivity of immunosensors makes them ideal for situations requiring speed and accuracy (Rabbany et al., 1994 *Crit Rev Biomed Eng* 22:307-346).

Detection techniques employed by immunosensors include electrochemical, piezoelectric or optical detection of the immunointeraction (Ghindilis et al., 1998 *Biosens Bioelectron* 1:113-131). An indirect immunosensor uses a separate labelled species that is detected after binding by, for example, fluorescence or luminescence (Morgan et al., 1996 *Clin Chem* 42:193-209). Direct immunosensors detect the binding by a change in potential difference, current, resistance, mass, heat or optical properties (Morgan et al., 1996 *Clin Chem* 42:193-209). Indirect immunosensors may encounter fewer problems due to non-specific binding (Attridge et al., 1991 *Biosens Bioelecton* 6:201-214; Morgan et al., 1996 *Clin Chem* 42:193-209).

Further Aspects of the Invention

We provide a nucleic acid molecule which is at least 90% homologous to SEQ ID NO: 1 and a nucleic acid molecule which is at least 75% homologous to SEQ ID NO: No. 3.

We disclose polynucleotides which comprise a contiguous stretch of nucleotides from SEQ ID NO: 1 or SEQ ID NO: 3, or any of SEQ ID NOs: 5 to 9, or of a sequence at least 90% homologous thereto. Advantageously, this stretch of contiguous nucleotides is 50 nucleotides in length, preferably 40, 35, 30, 25, 20, 15 or 10 nucleotides in length.

The genes GCR1 and GCR2 encode novel polypeptides, the sequences of which are set forth in SEQ ID NO: 2 and SEQ ID NO: 4. We therefore disclose polypeptides encoded by the nucleic acids described here. Preferably, the polypeptides have the sequences set forth in SEQ ID NO: 2 and SEQ ID NO: 4.

Moreover, we provide a method by which genes specifically expressed in PGCs or other pluripotent cells, such as ES or EG cells, may be isolated, comprising the steps of: (a) providing a population of cells containing PGCs or other pluripotent cells, such as ES or EG cells; (b) isolating one or more PGCs or other pluripotent cells, such as ES or EG cells, therefrom and providing single-cell isolates; (c) amplifying the transcribed nucleic acid present in a single cell; (d) conducting a subtractive hybridisation screen to identify transcripts present in the PGCs or other pluripotent cells, such as ES or EG cells, but not in somatic cells; and (e) probing a nucleic acid library with one or more transcripts identified in d) to clone one or more genes which are specifically expressed.

Further aspects of the invention are now set out in the following numbered paragraphs; it is to be understood that the invention encompasses these aspects:

Paragraph 1. A nucleic acid having at least 90% homology with the sequence set forth in SEQ. ID. No. 1.

Paragraph 2. A nucleic acid having at least 75% homology with the sequence set forth in SEQ. ID. No. 3.

Paragraph 3. A nucleic acid comprising a sequence of 25 contiguous nucleotides of the nucleic acid of Paragraph 1 or Paragraph 2.

Paragraph 4. A nucleic acid comprising a sequence of 15 contiguous nucleotides of the nucleic acid of Paragraph 1 or Paragraph 2.

Paragraph 5. The complement of a nucleic acid sequence according to any preceding Paragraph.

Paragraph 6. A nucleic acid according to any one of Paragraphs 1 to 5, comprising one or more nucleotide substitutions, wherein such substitutions do not alter the coding specificity of said nucleic acid as a result of the degeneracy of the genetic code.

Paragraph 7. A polypeptide encoded by a nucleic acid according to any preceding Paragraph.

Paragraph 8. A method for identifying a primordial germ cell in a population of cells, comprising detecting the expression of a nucleic acid sequence according to Paragraph 1 or Paragraph 2, or a homologue thereof.

Paragraph 9. A method according to Paragraph 8, comprising the steps of amplifying nucleic acids from putative PGCs using 5' and 3' primers specific for GCR1 and/or GCR2, and detecting amplified nucleic acid thus produced.

Paragraph 10. A method according to Paragraph 8, wherein the expression of the nucleic acid sequence is detected by in situ hybridisation.

Paragraph 11. A method according to Paragraph 8, wherein the expression of the nucleic acid sequence is determined by detecting the protein product encoded thereby.

Paragraph 12. A method according to Paragraph 11, wherein the protein product is detected by immunostaining.

Paragraph 13. An antibody specific for a polypeptide according to Paragraph 7.

Paragraph 14. An antibody according to Paragraph 13, specific for the extracellular domain of GCR1.

Paragraph 15. Use of an antibody according to Paragraph 13 or Paragraph 14 for the identification of a PGC in a population of cells.

Paragraph 16. A PGC when identified by a method according to any one of Paragraphs 8 to 12.

Paragraph 17. A method for isolating a gene specifically expressed in PGCs, comprising the steps of: a) providing a population of cells containing PGCs; b) isolating one or more PGCs therefrom and providing single-cell PGC isolates; c) amplifying the transcribed nucleic acid present in a single PGC; d) conducting a subtractive hybridisation screen to identify transcripts present in PGCs but not in somatic cells; and e) probing a nucleic acid library with one or more transcripts identified in d) to clone one or more genes which are specifically expressed in PGCs.

Paragraph 18. A GCR1 polypeptide, or a fragment, homologue, variant or derivative thereof.

Paragraph 19. A polypeptide according to paragraph 18, which has at least 50%, 60%, 70%, 80%, 90% or 95% homology to a sequence shown in SEQ ID NO: 2.

Paragraph 20. A GCR2 polypeptide, or a fragment, homologue, variant or derivative thereof.

Paragraph 21. A polypeptide according to paragraph 20, which has at least 50%, 60%, 70%, 80%, 90% or 95% homology to a sequence shown in SEQ ID NO: 4.

Paragraph 22. A nucleic acid encoding a polypeptide according to any preceding paragraph.

Paragraph 23. A nucleic acid having at least 90% homology with the sequence set forth in SEQ ID NO: 1, or a fragment, variant or derivative thereof.

Paragraph 24. A nucleic acid having at least 75% homology with the sequence set forth in SEQ ID NO: 3, SEQ ID NO: 5, SEQ ID NO: 6, SEQ ID NO: 7, SEQ ID NO: 8 or SEQ ID NO: 9 or a fragment, variant or derivative thereof.

Paragraph 25. A nucleic acid comprising a sequence of 25 contiguous nucleotides of a nucleic acid according to paragraph 22, 23 or 24.

Paragraph 26. A nucleic acid comprising a sequence of 15 contiguous nucleotides of a nucleic acid according to any of paragraphs 22 to 25.

Paragraph 27. The complement of a nucleic acid sequence according to any of paragraphs 22 to 26.

Paragraph 28. A nucleic acid according to any of paragraphs 22 to 27, comprising one or more nucleotide substitutions, wherein such substitutions do not alter the coding specificity of said nucleic acid as a result of the degeneracy of the genetic code.

Paragraph 29. A polypeptide encoded by a nucleic acid according to any preceding paragraph.

Paragraph 30. A polypeptide according to paragraph 29, in which the polypeptide comprises a sequence shown in SEQ ID NO: 2 or SEQ ID NO: 4.

Paragraph 31. A method for identifying a pluripotent cell, comprising detecting the presence of a polypeptide according to any of paragraphs 18 to 21, 29 or 30 or the expression of a nucleic acid according to any of paragraphs 22 to 28, or a homologue thereof.

Paragraph 32. A method according to paragraph 31, comprising the steps of amplifying nucleic acids from a putative pluripotent cell using 5' and 3' primers specific for GCR1 and/or GCR2, and detecting amplified nucleic acid thus produced.

Paragraph 33. A method according to paragraph 31, wherein the expression of the nucleic acid sequence is detected by in situ hybridisation.

Paragraph 34. A method according to paragraph 25, wherein the expression of the nucleic acid sequence is determined by detecting the protein product encoded thereby.

Paragraph 35. A method according to paragraph 31 or paragraph 34, wherein the protein product is detected by immunostaining.

Paragraph 36. An antibody specific for a polypeptide according to any of paragraphs 18 to 21, 29 or 30.

Paragraph 37. An antibody according to paragraph 36, which is capable of specifically binding to an extracellular domain of GCR1.

Paragraph 38. Use of an antibody according to paragraph 36 or paragraph 37 for the identification and/or isolation of a pluripotent cell.

Paragraph 39. A pluripotent cell identified by a method according to any one of paragraphs 31 to 35 and 38.

Paragraph 40. A method for isolating a gene specifically expressed in a pluripotent cell, comprising the steps of (a) providing a population of cells containing a pluripotent cell; (b) isolating one or more pluripotent cells therefrom and providing single-cell pluripotent cell isolates; (c) amplifying the transcribed nucleic acid present in a single pluripotent cell; (d) conducting a subtractive hybridisation screen to identify transcripts present in pluripotent cells but not in somatic cells; and (e) probing a nucleic acid library with one or more transcripts identified in (d) to clone one or more genes which are specifically expressed in pluripotent cells.

Paragraph 41. A method according to any of paragraphs 31 to 35 or 40, a use according to paragraph 38, a pluripotent cell according to paragraph 40, in which the pluripotent cell is selected from the group consisting of a primordial germ cell (PGC), an embryonic stem cell (ES) and an embryonic germ cell (EG).

Paragraph 42. A transgenic non-human animal comprising a nucleic acid according to any of paragraphs 18 to 28.

Paragraph 43. A transgenic non-human animal according to paragaph 42 which is a mouse.

Paragraph 44. A cell or tissue from a transgenic non-human animal according to paragraph 42.

Paragraph 45. Use of a transgenic non-human animal according to claim 42, or a cell or tissue according to paragraph 44, in a method of identifying a compound which is capable of interacting specifically with a Stella or Fragilis protein.

Paragraph 46. A non-human transgenic animal, characterised in that the transgenic animal comprises an altered Stella gene or an altered Fragilis gene, or both.

Paragraph 47. A non-human transgenic animal according to claim 46, in which the alteration is selected from the group consisting of: a deletion of Stella and/or Fragilis, a mutation in Stella and/or Fragilis resulting in loss of function, introduction of an exogenous gene having a nucleotide sequence with targeted or random mutations into Stella and/or Fragilis, introduction of an exogenous gene from another species into Stella and/or Fragilis, and a combination of any of these.

Paragraph 48. A non-human transgenic animal having a functionally disrupted endogenous Stella and/or Fragilis gene, in which the transgenic animal preferably comprises in its genome and expresses a transgene encoding a heterologous Stella and/or Fragilis protein.

Paragraph 49. A nucleic acid construct for functionally disrupting a Stella and/or Fragilis gene in a host cell, the nucleic acid construct comprising: (a) a non-homologous replacement portion; (b) a first homology region located upstream of the non-homologous replacement portion, the first homology region having a nucleotide sequence with substantial identity to a first Stella and/or Fragilis gene sequence; and (c) a second homology region located downstream of the non-homologous replacement portion, the second homology region having a nucleotide sequence with substantial identity to a second Stella and/or Fragilis gene sequence, the second Stella and/or Fragilis gene sequence having a location downstream of the first Stella and/or Fragilis gene sequence in a naturally occurring endogenous Stella and/or Fragilis gene.

EXAMPLES

Example 1

Identification of Genes Specific to the Earliest Population of Primordial Germ Cells (PGCs) by Single Cell cDNA Differential Screening A method for single cell analysis is developed to identify genes that are involved in the specification of the germ cell lineage, which results in the establishment of a founder population of Primordial Germ Cells (PGCs). It is determined that the lineage specification of PGCs accompanies the expression of a unique set of genes, which are not expressed in somatic cells.

The method for the identification of the genes is mainly based on the differential screening of the libraries made from single cells from day 7.25 mouse embryonic fragments that contain PGCs. The single cell cDNA differential screen was originally described by Brady and Iscove (1993), and subsequently modified by Cathaline Dulac and Richard Axel which resulted in the successful identification of the pheromone receptor genes from rat (Dulac, C. and Axel, 1995). The method of Axel's group is employed, with slight modifications as described.

Construction of Single Cell cDNAs from Embryonic Fragment Bearing the Earliest Population of PGCs In the mouse, the earliest population of the PGCs is reported to consist of alkaline phosphatase positive cluster of some 40 cells, at the base of the emerging allantois at day 7.25 of gestation (Ginsburg, M., Snow, M. H. L., and McLaren, A. (1990)). The precise location of the PGC cluster in the inbred 129Sv and C57BL/6 strain is determined by microscopy using both whole-mount alkaline phosphatase staining and semi-thin sections stained by methylene blue. The earliest stage at which a cluster of PGCs can be detected is at the Late Streak stage (Downs, K. M., and Davies, T. (1993)), when a distinctively stained population of cells is found just beneath an epithelial lining from which the allantoic bud appears. This region is at the border between the extraembryonic and embryonic tissues just posterior to and above the most proximal part of the primitive streak. The cluster persists at this position at least until Early/Mid Bud stage. In the inbred 129Sv strain, the PGC cluster is found to contain a slightly larger number of the cells, which are more tightly packaged than in the C57BL/6 strain. The 129Sv strain is used for subsequent experiments, as a better recovery of the earliest PGCs is obtained.

129Sv embryos are isolated at E7.5 in DMEM plus 10% FCS buffered with 25 mM HEPES at room temperature and the developmental stage of each embryo is determined under a dissection microscope. The precise developmental stage can differ substantially even amongst embryos within the same litter. Embryos that are at the no bud or early bud (allantoic) stage are chosen for further dissection, which in part is dictated by the ease of identification of the region containing PGCs as seen under the dissection microscope. The fragment that is expected to contain the PGC cluster is cut out very precisely by means of solid glass needles. This region is dissociated it into single cells using 0.25% trypsin-1 mM EGTA/PBS treatment at 37° C. for 10 mm, followed by gentle pipetting with a mouth pipette. The dissected fragment usually contained between 250-300 cells. The procedure for cell dispersal with this gentle procedure left the visceral endoderm layer remained as an intact cellular sheet.

We picked single cells randomly from the cell suspension by a mouth pipette and put individual single cells (but avoiding generating air bubbles), into a thin-walled PCR tube containing 41 µl of ice-cold cell lysis buffer (50 mM Tris-HCl pH8.3, 75 mM KCl, 3 mM $MgCl_2$, 0.5% NP-40, containing 80 ng/ml pd(T)24, 5 µg/ml prime RNase inhibitor, 324 U/ml RNA guard, and 10 mM each of dATP, dCTP, dGTP, and dTTP). The volume of medium carried with the single cell is less than 0.5 µl. The tube is briefly centrifuged to ensure that the cell is indeed in the lysis buffer. During each separate experiment, we picked a total of 19 single cells, and left one tube without a cell, to serve as a negative control for the PCR amplification procedure. All the cells that are collected in tubes are kept on ice before starting the subsequent procedure.

The cells are lysed by incubating the tubes at 65° C. for 1 min, and then kept at room temperature for 1-2 min to allow the oligo dT to anneal the to RNA. First-strand cDNA synthesis is initiated by adding 50 U of Moloney murine leukaemia virus (MMLV) and 0.5 U of avian myeloblastosis virus (AMV) reverse transcriptase followed by incubation for 15 min at 37° C. The reverse transcriptases are inactivated for 10 min at 65° C. This reverse transcription reaction is restricted to 15 min, which allows the synthesis of relatively uniform size cDNAs of between 500 base-1000 bases in length from the C termini. This enables the subsequent PCR amplification to be fairly representative.

Next, in order to add the poly A tail to the 5 prime end of the synthesised first-strand cDNA, 4.5 µl of 2× tailing buffer (200 mM potassium cacodylate pH7.2, 4 mM $CoCl_2$, 0.4 mM DTT, 200 mM dATP containing 10 U of terminal transferase) is added to the reaction followed by incubation for 15 min at 37° C. The samples are heat inactivated for 10 min at 65° C. The reaction now contained synthesised cDNAs bearing poly T tail at their C termini and poly A stretch at their N termini, ready for the amplification by the PCR using the specific primer.

The contents of each tube is brought to 100 µl with a solution made of 10 mM TrisHCl pH8.3, 50 mM KCl, 2.5 mM $MgCl_2$, 100 µg/ml bovine serum albumin, 0.05% Triton-X 100, 1 mM of dATP, dCTP, dGTP, dTlP, IOU of Taq polymerase, and 5 µg of the AL1 primer. The AL1 sequence is ATT GGA TCC AGG CCG CTC TGG ACA AAA TAT GAA TCC $(T)_{24}$ (SEQ ID NO:14). The PCR amplification is performed according to the following schedule: 94° C. for 1 min, 42° C. for 2 min, and 72° C. for 6 min with 10 s extension per cycle for 25 cycles. Five additional units of Taq polymerase are added before performing 25 more cycles with the same programme but without the extension time. Each tube at this point contains amplified cDNA products derived from a single cell. The protein contents of the solution are extracted by phenol/chloroform treatment, and the amplified cDNAs are precipitated by ethanol and eventually suspended in 100 µl of TE pH8.0. 5 µl of the cDNA solution is run on a 1.5% agarose gel to check the success of the amplification. Most of the samples show a very intense 'smeared' band ranging mainly between 500 bp to 1200 bp, indicating the efficient amplification of the single cell cDNA. Only the successfully amplified samples are used for the subsequent 'cell typing' analysis.

Example 2

Identification of PGCs by Examination of the Expression of Marker Genes

The embryonic fragment which is excised theoretically contains three major components: the allantoic mesoderm, PGCs, and extraembryonic mesoderm surrounding PGCs. In order to identify the single cell CDNA of PGC origin amongst these samples, positive and negative selection of the constructed cDNAs is performed, by examining the expression of four marker genes (BMP4, TNAP, Hoxb1, and Oct4), which are known to be either expressed or repressed in various cell types in this region.

At the No/Early Bud stage, BMP4 is reported to be expressed in the emerging allantois and mesodermal components of the developing amnion, chorion, and visceral yolk sac (Lawson, K. A., Dunn, N. R., Roelen, B. A. J., Zeinstra, L. M., Davis, A. M., Wright, C. V. E., Korving, J. P. W. F. M., and Hogan, B. L. M. (1999)). The boundary of BMP4 expression is very sharp, and the expression is completely excluded in the mesodermal region beneath the epithelial lining continuous from the amnionic mesoderm where the putative PGCs are determined. Therefore, BMP4 is used as a negative marker for the selection. Primer pairs are designed for amplifying the C terminal portion of BMP4 (5': GCC ATA CCT TGA CCC GCA GAA G. 3' (SEQ ID NO:15): AAA TGG CAC TCA GTT CAG TGG G (SEQ ID NO:16)). The PCR amplification is performed using 0.5 µl of the cDNA solution as a template according to the following schedule: 95° C. for 1 min, 55° C. for 1 min, and 72° C. for 1 min for 20 cycles. Among 83 samples tested, 57 samples show the expected size of bands, indicating expression of BMP4 these single cells. These samples are considered to be of allantoic mesodermal origin, and therefore excluded from amongst the candidates representing cells of PGC origin.

The expression of tissue non-specific alkaline phosphatase (TNAP), which has, long been used as an early marker for PGCs (Ginsburg, M., Snow, M. H. L., and McLaren, A. (1990)), is then examined. Primer pairs are designed (5': CCC AAA GCA CCT TAT TTT TCT ACC, 3' (SEQ ID NO:17): TTG GCG AGT CTC TGC AAT TGG (SEQ ID NO:18)) and the same PCR reaction as above is performed. Amongst the 26 samples, 22 samples are judged to be positive for TNAP. From the alkaline phosphatase staining of the sectioned embryos, it is known that the somatic cells surrounding PGCs also express some amount of TNAP, although the level of expression is slightly lower than that in PGCs. Therefore, amongst these 22 positive samples there should be still be cells destined to become somatic cells as well as PGCs.

One of the genes known to be expressed in the totipotent PGCs but not in somatic cells is Oct4 (Yoem, Y. I I., Fuhrmann, G., Ovitt, C. E., Brehm, A., Ohbo, K., Gross, M., Hubner, K., and Scholer, H. R. (1996)). To examine the possibility that Oct4 can be used as a marker to distinguish PGCs from somatic cells at this stage, Oct4 expression is checked in the 22 samples by PCR (5': CAC TCT ACT CAG TCC CTT TTC, 3' (SEQ ID NO:19): TGT GTC CCA GTC TTT ATT TAA G (SEQ ID NO:20)). All the 22 samples express Oct4 at comparable levels, indicating that the somatic cells at this stage are still actively transcribing Oct4 RNA.

The amount of expression of TNAP is quantitated in 22 samples by Southern blot analysis (reverse northern blot analysis). Given the fairly representative amplification of the single cell method, confirmed by amplifying single ES cell cDNA, Southern blot analysis allows semi-quantitative measurement of the amount of the genes expressed in the original single cells, although it does not serve as a perfect indicator of cell identity. However, as a result of this TNAP analysis, 10 samples out of 22 show relatively stronger bands at an equivalent level, while the remaining 12 samples exhibit weaker signals. These results indicate that these 22 samples can be divided at least into two groups, one with stronger TNAP expression (therefore from putative PGCs) and the other with weaker TNAP.

The possibility that somatic cells surrounding PGCs start to express Hoxb1, while PGCs do not (personal communication from Dr. Kirstie Lawson) is also examined. Primer pairs are designed (5': AAC TCA TCA GAG GTC GAA GGA, 3' (SEQ ID NO:21): CGG TGC TAT TGT AAG GTC TGC (SEQ ID NO:22)) and the same PCR reaction as above is performed. Among the 22 samples tested, 12 are positive, and more importantly, these 12 samples perfectly match the ones which show weaker TNAP signals, by Southern blot analysis.

Taking all these results into consideration, it is concluded that 10 samples out of 83, which are Oct4 (+), TNAP (++), BMP4 (−), and Hoxb1(−), are of PGC origin. This ratio (10/83) is reasonable, considering the number of the founding population of PGCs as 40 and the number of cells in the fragment as 250-300.

Example 3

Differential Screening of Single Cell cDNA Libraries

As the efficiency of the amplification of cDNA differs in each tube, it is very important to select the samples with the most efficiently amplified cDNA for the construction of libraries. The amplification of six different genes (ribosomal protein S12, intermediate filament protein vimentin, β tubulin-5, α actin, Oct4, E-cadherin) is examined in the 10 PGC candidate samples, by Southern blot analysis. Judging from the overall profile of the amplification of all these six genes, three cDNA preparations are selected for the construction of libraries.

To obtain the maximum amount of double strand cDNA, an extension step is performed with 5 μl of cell cDNA in 100 μl of the PCR buffer described as above (including 1 μl of Amplitaq) according to the following schedule: 94° C. for 5 min, 42° C. for 5 min, 72° C. for 30 min. The solution is extracted by phenol/chloroform treatment, and the amplified cDNAs are precipitated by ethanol, suspended in TE, and completely digested with EcoRI. The PCR primer and excess amount of dNTPs are removed by QIAGEN PCR Purification Kit, and all the purified cDNAs are run on a 2% low melting agarose gel. cDNAs above 500 bp are cut and purified by QIAGEN Gel Purification Kit. The purified cDNAs are precipitated by ethanol and suspended in TE and ligated into λ ZAP II vector arms. The ligated vector is packaged, titered and the ratio of the successfully ligated clones is monitored by amplifying the inserts with T3 and T7 primers from 20 plaques. More than 95% of the phage are found to contain inserts.

The representation of the three genes, ribosomal protein SI12, β tubulin-5, Oct4, is quantitated by screening 5000 plaques, and the library of the best quality among the three (S12 0.62%, β tubulin 0.4%, Oct4 0.5%) is used for the differential screening. As a comparison partner with the PGC probe, one of the most efficiently amplified surrounding somatic cell cDNA (Oct4 (+), TNAP(+/−), BMP(−), and Hoxb1(+)) is selected by the similar Southern blot analysis.

The library is plated at a density of 1000 plaques per 15 cm dish to obtain large plaques (2 mm diameter) and two duplicate lifts are taken using Hybond N+ filters from Amersham. The filters are prehybridized at 65° C. in 0.5M sodium phosphate buffer (pH 7.3) containing 1% bovine serum albumin and 4% SDS. We prepared the cell cDNA probes by reamplifying for 10 cycles 1 pt of the original cell cDNA into 50 μl of total reaction with the AL1 primer, in the absence of cold dCTP and with 100 μCi of newly received $^{32}$PdCTP, followed by the purification using Amersham Nick™ Spin Column. The filters are hybridised for at least 16 hrs with $1.0 \times 10^7$ cpm/ml (The first filter is hybridised with somatic cell probe and the second filter is hybridised with the PGC probe). After the hybridisation, the filters are washed three times at 65° C. in 0.5×SSC, 0.5% SDS and exposed to X ray films until the appropriate signal is obtained (usually one to two days).

The positive plaques in the two duplicate filters are compared very carefully. Among 5000 plaques screened, 280 are picked as candidates representing the differentially expressed genes. The inserts of all the 280 plaques are amplified with T3 and T7 primers, run on 1.5% gels, and double sandwich Southern blotted. Each membrane is hybridised with the PGC and somatic cell probe, respectively, using the same conditions as the screening. 38 clones amongst the 280 are selected as differentially expressed genes. These clones are next hybridised with the second PGC and somatic cell cDNA probes, which resulted in 20 clones out of 38 to be common in both PGC cDNAs but they are either not included or less abundant in both somatic cell cDNAs. The sequences of all the 20 clones are determined.

Genes Highly Specific to the Earliest Population of PGCs

The 20 clones represent 11 different genes (two clones appear two times, one clone appears three times, and one clone appears 6 times). To further stringently check the specificity of expression, primer pairs are designed for these 11 clones and their expression checked in 10 different single PGC-Candidate cDNAs and 10 different single somatic cell cDNAs by PCR. Two of them show highly specific expression to PGC cDNAs.

The first gene, GCR1 (Germ cell restricted-1, Fragilis), encodes a 137 amino acid protein with a predicted molecular weight of 15.0 kD. Nucleotide and amino acid sequences of mouse Fragilis are shown in FIG. 1.

The best fit model of the EMBL program PredictProtein predicts two transmembrane domains, both N and C terminus ends being located outside. The BLASP search revealed that Fragilis is a novel member of the interferon-inducible protein family. One prototype member, human 9-27 (identical to Leu-13 antigen), is inducible by interferon in leukocytes and endothelial cells, and is located at the cell surface as a component of a multimeric complex involved in the transduction of antiproliferative and homotypic adhesion signals (Deblandre, 1995). The BLASTN search revealed that the Fragilis sequence was found in ESTs derived from many different tissues both from embryos and adults, indicating that Fragilis may play a common role in different developmental and cell biological contexts. Database searches reveal a sequence match with the rat interferon-inducible protein (sp:INIB RAT, pir:JC1241) with unknown function. The GCR1 sequence appears six times in our screen, indicating high level expression in PGCs.

The second gene, GCR2, (Stella) encodes a 150 amino acid protein, of 18 kD. Nucleotide and amino acid sequences of mouse Fragilis are shown in FIG. 2.

It has no sequence homology with any known protein, contains several nuclear localisation consensus sequences and is highly basic pI (pI=9.67, the content of basic residues=23.3%), indicating a possible affinity to DNA. Furthermore a potential nuclear export signal was identified, indicating that Stella may shuttle between the nucleus and the cytoplasm. BLASTN analysis revealed that the Stella sequence was found only in the preimplantation embryo and germ line (newborn ovary, female 12.5 mesonephros and gonad etc.) ESTs indicating its predominant expression in totipotent and pluripotent cells. Interestingly, we found that Stella contains in its N terminus a modular domain which has some sequence similarity with the SAP motif. This motif is a putative DNA-binding domain involved in chromosomal orgainisation. Furthermore, the SMART program revealed the presence of a splicing factor motif-like structure in its C-terminus, These findings indicate a possible involvement of Stella in chromosomal orgainistion and RNA processing.

Example 4

Identification of PGCs by Screening for GCR1 and GCR2 Expression

Although PGCs are identified in Example 2 by analysis of BMP4, TNAP, Hoxb1, and Oct4, no single one of these genes can be taken as a marker for the PGC state. However, both GCR1 and GCR2 may be used as such.

The expression of GCR1 is examined. Primer pairs are designed (5': CTACTCCGTGAAGTCTAGG, 3' (SEQ ID NO:23): AATGAGTGTTACACCTGCGTG (SEQ ID NO:24)) and the same PCR reaction as above is performed. GCR1 expression was detected in germ cell competent cells. The definitive PGCs were recruited from amongst this group of cells showing expression of GCR1.

The boundary of GCR2 expression in particular is well-defined, and the expression is substantially limited to PGCs. Therefore, GCR2 is used as a positive marker for the selection of PGCs. Primer pairs are designed for amplifying the C terminal portion of GCR2 (5': GCCATTCAGATGTCTCTG-CAC, 3' (SEQ ID NO:25): CTCACAGCTTGAGGCT-TCTAA (SEQ ID NO:26)). The PCR amplification is performed using 0.5 µl of the cDNA solution obtained from PGCs in Example 1 as a template according to the following schedule: 95° C. for 1 min, 55° C. for 1 min, and 72° C. for 1 min for 20 cycles. Among 83 samples tested, only those taken from PGCs show expression of GCR2. Hence, GCR2 is a positive marker for the PGC fate.

Antibodies against GCR1 and GCR2 can be similarly used to detect pluripotent cells. Preferably, antibodies against GCR1 are used to detect germ cell competent cells, and antibodies against GCR2 are used to detect PGCs.

Accordingly, both GCR1 and GCR2 are positive markers for the PGC fate which can be used to positively identify PGC.

Identification of PGC by ISH

The in vivo expression of the two genes is examined by in situ hybridisation. The expression of GCR1 starts very weakly in the entire epiblast at E6.0-E6.5 (PreStreak stage) and becomes strong in the few cell layers of the proximal rim of the epiblast. BMP4 that is expressed in the extraembryonic ectoderm is one signalling molecule that is important for the induction of germ cell competence and expression of GCR1. Other signals, such as interferons are likely to be involved in the induction of GCR1. The expression becomes more intense at the proximo-posterior end of the developing primitive streak at the Early/Mid Streak stage and becomes very strong at this position from Late Streak stage onward. The expression persists until Early Head Fold stage and eventually disappears gradually. No expression is detected in the migrating PGCs at E8.5.

The expression of GCR2 starts at the proximo-posterior end of the developing primitive streak at Mid/Late Streak stage and becomes gradually strong at the same position from the later stage onward. The expression is specific and individual single cells stained in a dotted manner can be seen in the region where PGCs are considered to start differentiating as a cluster of cells. At Late Bud/Early Head Fold stage, some cells considered to be migrating from the initial cluster are stained as well as cells in the cluster. At E8.5 and E9.5, a group of cells considered to be the migrating PGCs are very specifically stained.

From these results, it is concluded that GCR1 is a gene which is upregulated during the process of lineage specification and germ cell competence, and subsequently of PGCs, when GCR2 is turned on after GCR1 to fix the PGC fate.

Accordingly, expression of GCR1 may be detected in a method of detecting lineage specification, and/or pluripotency, such as germ cell competence. Similarly, expression of GCR2 may be detected to detect commitment to cell fate, for example, commitment to fate as a primordial germ cell.

Example 5

Expression of Fragilis and Stella During Germ Line Development

Antibodies against Stella and Fragilis are used to detect expression of these genes in early embryos. It is found that each of these genes is expressed in primordial germ cells. In particular, we find that Fragilis is the first gene to mark PGC competent cells at the time of germ cell allocation. Stella is expressed only in the lineage-restricted founder PGCs and thereafter in the germ cell lineage.

FIG. 3 shows expression of Fragilis in embryonic stem (ES) cells.

Fragilis is expressed in pluripotent ES and EG cells. During the derivation of EG cells from PGCs, it is found that Fragilis expression re-appears on EG cells. Late PGCs are negative for Fragilis after specification of these cells is completed.

Figure 5:
FIG. 5. Fragilis expression by whole-mount in situ hybridization in E7.2 mouse embryos.

FIG. 5 shows expression of Fragilis as detected by whole-mount in situ hybridization in E7.2 mouse embryos.

There is strong Fragilis expression at the base of incipient allantois where the founder PGC population differentiates in the E7.25 embryos. Fragilis expression persisted until E7.5, but it was not detected in migrating PGCs at E8.5. Fragilis is first detected in germ cell competent proximal epiblast cells. Fragilis expression can be induced in the epiblast cells when combined with the tissues extraembryonic ectoderm tissues, which is the source of BMP4. In the BMP4 mutant mice, there is no expression of Fragilis, consistent with the absence of PGCs in these embryos (Lawson et al., 1999).

Figure 4:
FIG. 4: Expression of Stella in PGCs. PGCs from E12.5 genital ridges are fixed in 4% paraformaldehyde in PBS for 10 min. at room temperature and processed for immunohistochemistry as described by Saitou et al., (1998). *J Cell Biol* 141, 397-408. (1998). Stella is detected in PGCs from E 7.25-13.5, as well as in pluripotent ES cells and in EG cells. Stella is also detected in the totipotent oocyte, zygote and in the totipotent and pluripotent blastomeres during preimplantation development and in developing gametes. When EG cells are derived from PGCs (Labosky et al., (1994) Development 120:3197-3204). Fragilis expression is again detected in the pluripotent EG cells as it is in ES cells. Therefore, Fragilis and Stella are also markers for the pluripotent stem cells.

FIG. 4 shows expression of Stella in PGCs.

Figure 7:
FIG. 7. Stella expression in PGCs in the process of migration into the gonads in E9.0 embryos.

Stella expression which is strong in PGCs is downregulated in EG cells. There is also low level expression of Stella in ES cells. Stella and Fragilis are detectable in ES and EG cells by Northern blot analysis. Stella is first detected at E7.0 in single cells within the distinctive cluster of lineage-restricted PGCs, and thereafter in migrating PGCs and subsequently when they enter the gonads. FIG. 7 shows Stella expression in PGCs in the process of migration into the gonads in E9.0 embryos. Stella is the only gene so far known to be a definitive marker for the founder population of PGCs.

Figure 6:
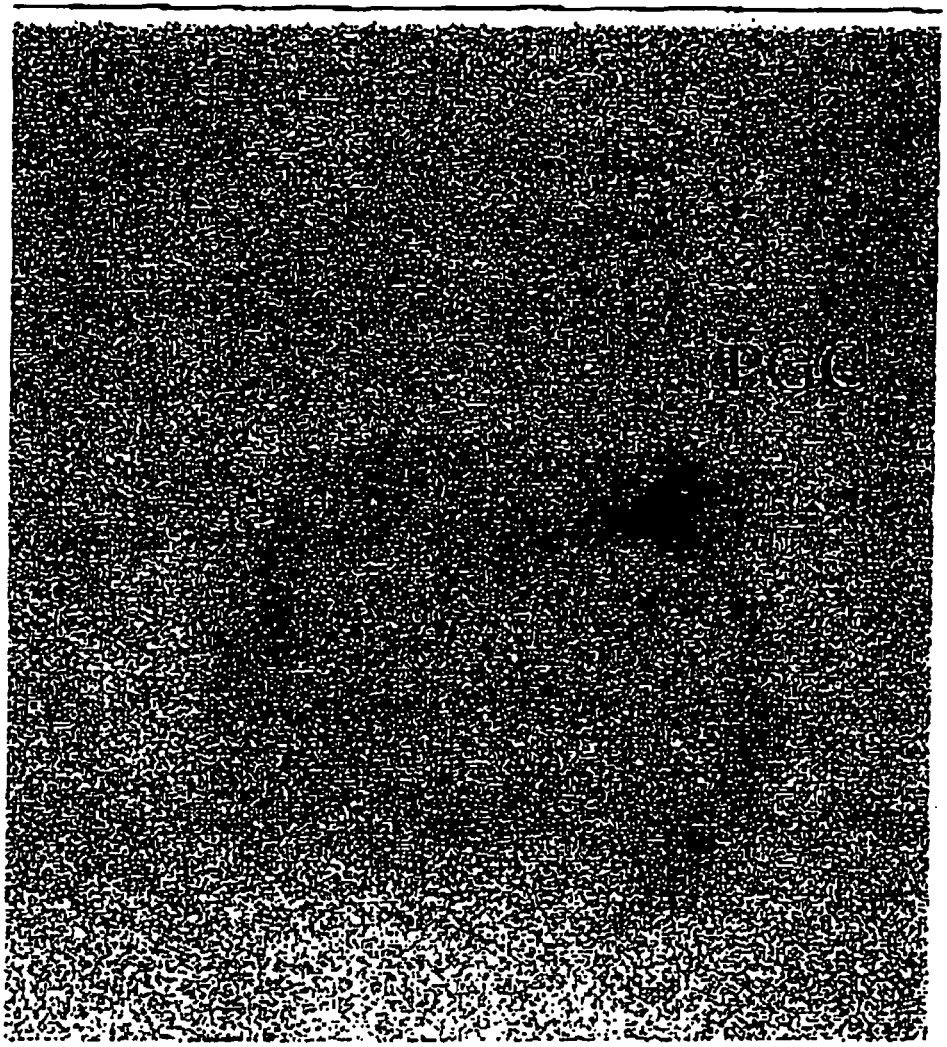
FIG. 6. Stella expression by whole mount in situ hybridisation in E 7.2 mouse embryos.

FIG. 6 shows expression of Stella as detected by whole-mount in situ hybridization in E7.2 mouse embryos.

FIG. 8. Expression of Fragilis and Stella in single cells detected by PCR analysis of single cell cDNAs. Note that there are more single cells showing expression of Fragilis compared to those showing expression of Stella. Only cells with the highest levels of Fragilis expression are found to express Stella and acquire the germ cell fate. Cells that express Stella were found not to show expression of Hoxb1. Cells that express lower levels of Fragilis and no Stella become somatic cells and show expression of Hoxb1. The founder population of PGCs also show high levels of Tnap. Both the founder PGCs and the somatic cells show expression of Oct4, T(Brachyury), and Fgf8.

Example 6

Expression of Fragilis and Stella in Individual Cells

Intracellular localisation of Stella and Fragilis is also determined. Fragilis localised to a single cytoplasmic spot at the Golgi apparatus, as well as in the plasma membrane. Stella comprises a putative nuclear localisation signal and nuclear export signal, and is localised in both the cytoplasm and nucleus.

Fragilis is observed in the Golgi apparatus as well as in the plasma membrane of PGCs. The cell surface localization of Fragilis is expected as a member of the interferon inducible gene family [Deblandre, 1995]. Expression of Fragilis in the proximal rim of the epiblast marks the onset of germ cell competence. Fragilis has an IFN response element upstream of its exon 1, so it is very likely to be induced by IFN after initial priming by BMP4 of the proximal epiblast cells. These IFN inducible proteins can from a multimeric complex with other proteins such as TAPA1, which is capable of transduction of antiproliferative signals, which may be why the cell cycle time in founder PGCs increases from 6 to 16 hr, while the somatic cells continue to divide rapidly.

Stella, which has the putative nuclear localization signal and a nuclear export signal, was observed in both the cytoplasm and the nucleus. The onset of Stella is followed by the loss of Fragilis expression by E8.5. Therefore, Fragilis expresiion marks the onset of germ cell competence and Stella expression marks the end of this specification process. Expression of Stella in the founder PGCs marks an escape from the somatic cell fate and consistent with their pluripotent state. These studies indicate that specific set of genes are required to impose a germ line fate on cells that may otherwise become somatic cells. Stella, with its potential to shuttle between the nucleus and cytoplasm, could have a role in transcriptional and translational regulation, since many organisms possess elaborate transcriptional mechanisms to prevent germ cells from becoming somatic cells. Expression of Stella in the oocyte and preimplantation embryos indicates that it has a wider role in totipotency and pluripotency.

Example 7

The Link Between Fragilis and Stella

Only some of the cells that express Fragilis, ended up showing expression of Stella. Only those cells with the higest levels of Fragilis expression become PGCs and began to express Stella. Furthermore, Stella positive PGCs never show expression of Hoxb1. More importantly, only somatic cells with lower levels of Fragilis expression, show Hoxb1 expression. Furthermore, only the somatic cells show expression of two other homeobox-containing genes, Lim1 and Evx-1. Therefore lack of expression of Hoxb1, Evx-1 and Lim1, appears to be important for the specification of germ cell fate.

Figure 8A:
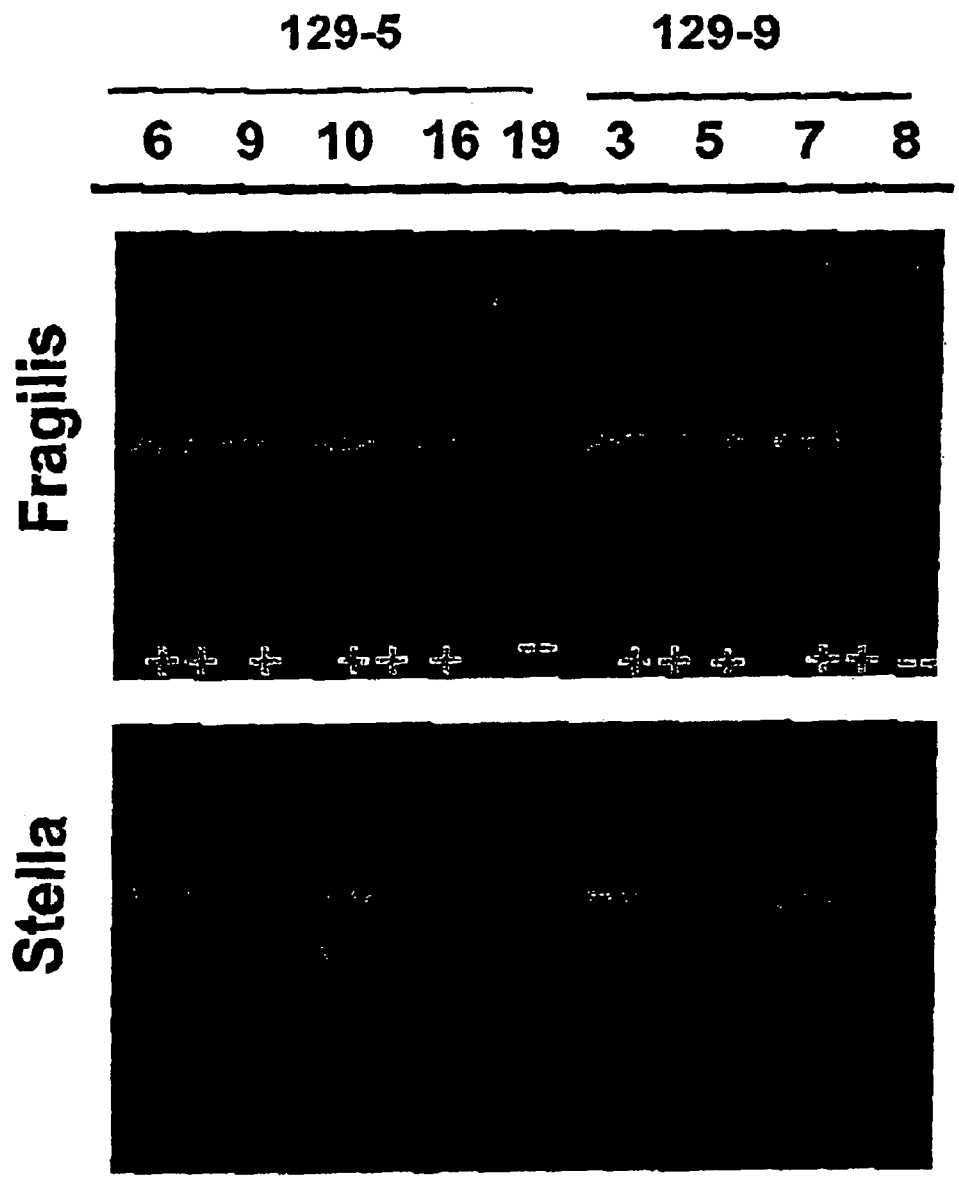
FIGS. 8a and 8b. Expression of Fragilis and Stella in single cells detected by PCR analysis of single cell cDNAs. Numbers marked by symbol* in 8b are the PGCs. Note that there are more single cells showing expression of Fragilis compared to those showing expression of Stella. Only cells with the highest levels of Fragilis expression were found to express Stella and acquire the germ cell fate. Cells that express Stella were found not to show expression of Hoxb1. Cells that express lower levels of Fragilis and no Stella become somatic cells and showed expression of Hoxb1. The founder population of PGCs also show high levels of Tnap. Both the founder PGCs and the somatic cells show expression of Oct4, T(Brachyury), and Fgf8.
Figure 8B:
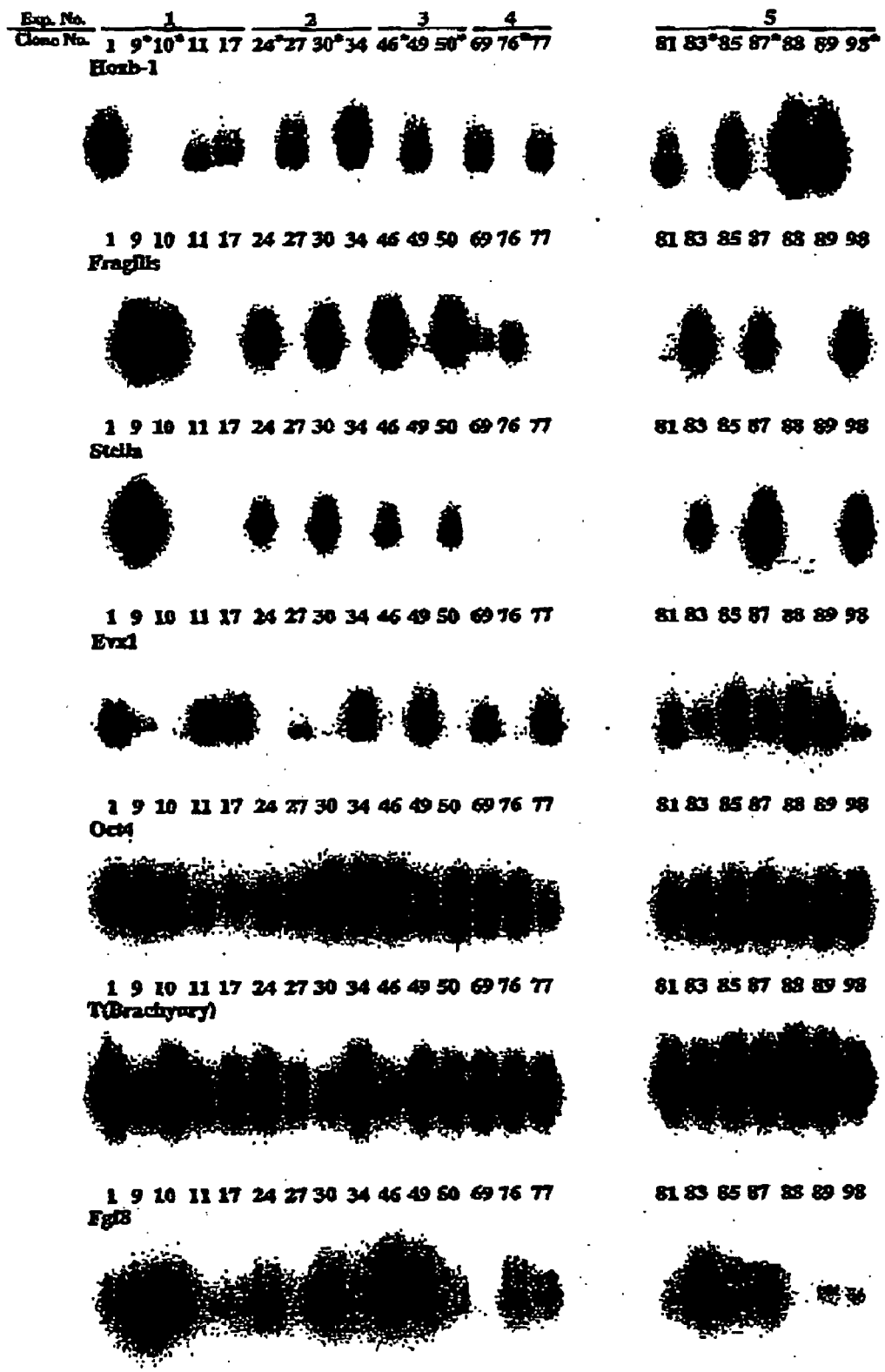

FIGS. 8a and 8b show expression of various genes in single cell PGCs and somatic cells by PCR analysis.

Our experiments also show that Oct4 is not a definitive marker of PGC, Previously, Oct4 expression is demonstrated in totipiotent and pluripotent cells [Nichols, 199, Pesce, 1998; Yeom, 1996]. However, we find that Oct4 is expressed to the same extent in all PGCs and somatic cells. We do however find expression of T (Brachyuri) and Fgf 8 in PGCs indicating that PGCs are recruited from amongst embryonic cells that are initially destined to become mesodermal cells.

Example 8

PGC Specification

The founder PGCs and their somatic neighbours share common origin from the proximal epiblast cells. By analysing the founder PGC and the somatic neighbour, a systematic screen for critical genes for the specification of germ cell fate has been established. Fragilis is an interferon (IFN) inducible gene that can promote germ cell competence and homotypic association to demarcate putative germ cells from their somatic neighbours, and such an example may apply to other situation during development. Expression of Stella occurs in cells with high expression of Fragilis. Fragilis is no longer required once germ cell specification is complete, but Stella expression continues in the germ cell lineage. Stella may also be important throughout in the totipotent/pluripotent cells since it is also expressed in oocytes and early preimplantion development embryos.

Example 9

Germ Line and Pluripotent Stem Cells

PGCs can be used to derive pluripotent embryonic germ (EG) cells. However, unlike EG cells, PGCs do not participate in development if introduced into blastocysts. They either cannot respond to signalling molecules, or that they are transcriptionally repressed. PGCs once specified do not express Fragilis on their cell surface. However, EG cells clearly show expression of Fragilis on their cell surface as do ES cells. Both EG and ES cells express Stella as judged by Northern analysis, although Stella is expressed at a lower level in ES and EG cells than in PGCs. Fragilis and Stella therefore have a role in pluripotent stem cells. These genes are therefore markers of these pluripotent stem cells, where they may also have a role in conferring pluripotency on these stem cells.

Example 10

Proposed Roles of Fragilis and Stella in PGC Specification

Fragilis as a typical IFN-inducible cell surface protein, probably shares certain properties common to all of these family members (Deblandre, G. A. et al. Expression cloning of an interferon-inducible 17-kDa membrane protein implicated in the control of cell growth. J. Biol. Chem. 270, 23860-23866 (1995); Evans, S. S., Collea, R. P., Leasure, J. A. & Lee, D. B. IFN-a induces homotypic adhesion and Leu-13 expression in human B lymphoid cells. J. Immunol. 150, 736-747 (1993); Evans, S. S., Lee, D. B., Han, T., Tomasi, T. B. & Evans, R. L. Monoclonal antibody to the interferoninducible protein Leu-13 triggers aggregation and inhibits proliferation of leukemic B cells. Blood 76, 2583-2593 (1990)).

The acute but transient expression of fragilis is itself consistent with the kinetics of IFN-inducible genes that can increase by up to 40-fold within 1 h, and decline quickly after IFN withdrawal (Friedman, R. L., Manly, S. P., McMahon, M., Kerr, 1. M. & Stark, G. R. Transcriptional and posttranscriptional regulation of interferon-induced gene expression in human cells. Cell 38, 745-755 (1984)). This Fragilis positive assembly of cells could correspond to about 100 TNAP positive cells (Lawson, K. A. & Hage, W. J. Clonal analysis of the origin of primordial germ cells in the mouse. Ciba Found. Symp. 182, 68-84 (1994); Ginsburg, M., Snow, M. H. & McLaren, A. Primordial germ cells in the mouse embryo during gastrulation. Development 110, 521-528 (1990)), which is larger than the number of stella positive cells.

According to our estimates, the stella positive cluster in the 129/SvEv mouse strain consists of approximately 36-43 cells, which is close to the expected 45 nascent PGCs. The fragilis positive cells probably form a community of cells through homotypic adhesion (Evans, S. S., Collea, R. P., Leasure, J. A. & Lee, D. B. IFN-a induces homotypic adhesion and Leu-13 expression in human B lymphoid cells. J. Immunol. 150, 736-747 (1993); Evans, S. S., Lee, D. B., Han, T., Tomasi, T. B. & Evans, R. L. Monoclonal antibody to the interferoninducible protein Leu-13 triggers aggregation and inhibits proliferation of leukemic B cells. Blood 76, 2583-2593 (1990)), from which the founder PGCs are recruited, thus demarcating them from most of the cells destined for somatic tissues. These IFN-inducible cell surface proteins are capable of transduction of antiproliferative signals (Deblandre, G. A. et al. Expression cloning of an interferon-inducible 17-kDa membrane protein implicated in the control of cell growth. J. Biol. Chem. 270, 23860-23866 (1995)), which is a probable mechanism by which the cell cycle time in the nascent PGCs increases from 6 to 16 h, while the somatic cells continue to divide rapidly.

The induction of fragilis in epiblast cells may not by itself be sufficient for the expression of stella, as shown by our in vitro studies-induction may require a specific signal thought to be within the niche, for PGC specification in vivo (Lawson, K. A. et al. Bmp4 is required for the generation of primordial germ cells in the mouse embryo. Genes Dev. 13, 424-436 (1999); McLaren, A. Signaling for germ cells. Genes Dev. 13, 373-376 (1999)). This signal could be a specific ligand that binds to fragilis during the specification of germ cell fate. Once nascent PGCs are established, expression of fragilis is diminished by E8.0, thus freeing the PGCs from homotypic adhesion for their migration into the genital ridge (Wylie, C. Germ cells. Cell 96, 165-174 (1999); Gomperts, M., Garcia-Castro, M., Wylie, C. & Heasman, J. Interactions between primordial germ cells play a role in their migration in mouse embryos. Development 120, 135-141 (1994)). fragilis must have other functions, as it is apparently expressed elsewhere in developing embryos. In this context, we also note fragilis expression in pluripotent ES and embryonic germ cells (data not shown), where it may have a role in the propagation of the pluripotent state.

The role of stella may in part be regulated by its potential to shuttle between the nucleus and cytoplasm. We have observed, for example, that overexpression of stella in somatic cells causes the protein to be retained in the cytoplasm and not in the nucleus, as is predominantly the case in PGCs (data not shown). A particularly critical event involved in the specification of PGCs is repression of the region-specific homeobox genes, by which nascent PGCs escape from the somatic cell fate. As the expression of stella is most intimately connected with the generation of PGCs, this gene is a chief candidate for either initiating or maintaining repression of Hox genes in PGCs. The detection of stella in the oocyte and through pre-implantation development (B. Payer et al., unpublished data; Sato, M. et al. Identification of PGC7, a new gene expressed specifically in preimplantation embryos and germ cells. Mech. Dev. 113, 91-94 (2002)) suggests that it may serve a critical role during all the phases of totipotent/pluripotent states in mice.

Example 11

Fragilis 2, Fragilis 3, Fragilis 4 and Fragilis 5

Specification of primordial germ cells in mice depends on instructive signalling events, which act first to confer germ cell competence on epiblast cells, and second, to impose a germ cell fate upon competent precursors. fragilis, an interferon-inducible gene coding for a transmembrane protein, is the first gene to be implicated in the acquisition of germ cell competence.

In this and the following Examples (Examples 11 to 20), we describe four additional fragilis-related genes, fragilis2-5, which are clustered within a 70 kb region in the vicinity of the fragilis locus on Chr 7. These genes exist in a number of mammalian species, which in the human are also clustered on the syntenic region on Chr 11. In the mouse, fragilis2 and fragilis3, which are proximate to fragilis, exhibit expression that overlaps with the latter in the region of specification of primordial germ cells. Using single cell analysis, we confirm that all these three fragilis-related genes are predominant in nascent primordial germ cells, as well as in gonadal germ cells.

The Fragilis family of interferon-inducible genes is tightly associated with germ cell specification in mice. Furthermore, its evolutionary conservation suggests that it probably plays a critical role in all mammals. Detailed analysis of these genes may also elucidate the role of interferons as signalling molecular during development.

Example 12

Background to Examples

Germ line determination in the mouse is thought to occur through instructive signalling in the gastrulating post-implantation embryo [1, 2]. First, proximal epiblast cells acquire germ cell competence at E6.5, partly in response to extraembryonic ectoderm-derived signalling molecules. A subset of these competent cells then acquire a primordial germ cell (PGC) fate and a population of approximately 45 founder germ cells are detected in the posterior proximal region of the embryo at the base of the incipient allantoic bud on E 7.5 [1, 2]. The secreted signalling molecules, BMP4, BMP8b and BMP2 as well as components of the BMP signal transduction pathway, including Smad1 and Smad5, appear to be involved in the specification of PGCs [3-7]. However, in vitro culture studies and analysis of BMP4-deficient mice suggest that an additional signal may also be required for the acquisition of PGC fate, but its identity is yet unknown [2, 3].

We have identified fragilis, a putative interferon-inducible gene, which codes for a transmembrane protein that is apparently associated with the acquisition of germ cell competence by epiblast cells [8]. Extraembryonic ectoderm is able to induce fragilis expression in epiblast tissue, and BMP4 is required for this induction [8]. fragilis is expressed in proximal epiblast at E6.5, the region in which PGC-competent cells reside according to clonal analysis [1]. As these proximal cells move to the posterior proximal region during gastrulation, fragilis expression increases within a community of cells at the base of the incipient allantoic bud. Cells with the highest expression of fragilis initiate the germ cell-characteristic expression of TNAP and stella/PGC-7 [8, 9, 10]. These nascent PGCs with high expression of fragilis also show repression of Hox genes, including Hoxb1 in nascent PGCs [8].

In view of the strong association of fragilis with PGC specification, we have started to investigate further how this gene may be regulated and what precise function it serves during germ cell development. Towards this objective, we now report that fragilis belongs to a novel murine gene family, comprising five members, which code for five highly similar transmembrane proteins. More importantly; the genes are clustered within a 70 kb genomic region. As we found several homologues of the Fragilis family in human, cow and rat, they seem to be evolutionarily conserved amongst mammalian species. Most if not all homologous genes have been reported to be responsive to interferon signalling, which is in agreement with the presence of conserved interferon stimulable response elements (ISREs) within at least the murine and human loci. Furthermore, our in situ hybridisation and single cell expression analysis reveal that the two members located close to fragilis, fragilis2 and fragilis3, are also expressed in nascent PGCs, although their overall expression pattern in post-implantation embryos in other respects is distinct. Studies on the Fragilis family of genes could therefore be crucial for our understanding of PGC specification, especially since their homologues have been implicated in mediating homotypic cell adhesion and lengthening of the cell cycle time [14, 15]. These studies may also show how interferons act as signalling molecules, which has hitherto not been considered in the context of embryonic development.

Example 13

Materials and Methods: Database Searches and Animals

Ensembl and NCBI genome browsers are used for data retrieval.

Embryos and genital ridges used for in situ hybridisation experiments came from 129×129 or F1xGoF1 mothers, respectively. Embryos and genital ridges used for single cell analysis came from 129xSvEv or Oct4GFP(129)xMF1 mothers, respectively. The day of the vaginal plug was designated as E0.5. Embryos were staged according to Downs and Davies [22].

Example 14

Materials and Methods: In Situ Hybridisation

3'-fragments of fragilis and fragilis2-5 cDNAs were PCR amplified using the primers described below, and cloned into pGEMT vector (Promega). DIG-labelled antisense RNA probes were synthesized using DIG RNA labelling kit (Sp6/T7; Roche). In situ hybridisation on embryos and urogenital ridges was performed as described [23, 24]. Hybridisation was carried out using 1 µg/ml DIG-labelled RNA probe in hybridisation buffer (50% formamide, 1.3×SSC (pH 5), 5 mM EDTA (pH 8), 50 µg/ml yeast RNA, 0.2% Tween-20, 0.5% CHAPS, 100 µg/ml heparin in DEPC treated $H_2O$) at 70° C. over night. Hybridised probe was detected using alkaline phosphatase conjugated anti-DIG Fab fragments (Roche) and BM Purple alkaline phosphatase substrate (Roche).

Example 15

Materials and Methods: Preparation, PCR and Southern Blot Analysis of Single Cell cDNAs Early bud stage embryos (E 7.5) and genital ridges (E 11.5) were isolated in DMEM/0% fetal calf serum/25 mM HEPES (pH 7.4). Fragments bearing primordial and gonadal germ cells, respectively, were dissected out and dissociated into single cells. The latter were picked using mouth pipettes and their cDNAs were amplified as described previously [25]. The following primers were used in order to PCR amplify stella cDNA and 3'-fragments of fragilis and fragilis2-5 cDNAs (25 cycles of amplification): stella: 5'CTCACAGCTTGAGGCTTCTAA3' (SEQ ID NO:46), 5'GCGATTCAGATGTCTCTGCAC3' (SEQ ID NO:47), fragilis: 5'GTTATCACCATTGTTAGTGTCATC3' (SEQ ID NO:48), 5'AATGAGTGTTACACCTGCGTG3' (SEQ ID NO:49); fragilis3: 5'GATCTTCAGCATCCTTATGGTC3' (SEQ ID NO:50), 5'GAAGGTAACATTTGCATACGCG3' (SEQ ID NO:51; fragilis2: 5'CCTTCCTTATTCTCACTCTG3' (SEQ ID NO:52), 5'GTTGCAAGACATCTCACATC3' (SEQ ID NO:53); fragilis4: 5'AACTTGGAGGCTGCAAGGCAG3' (SEQ ID NO:54), 5'CTCGGAACTCTTAGTTATAGTC3' (SEQ ID NO:55); fragilis5: 5'TGCTCTGGTCATCTCCCTCA3' (SEQ ID NO:56), 5'CAGGATAAGGGGCAACTCTG3' (SEQ ID NO:57). PCR products were run on 1.5% agarose/TBE electrophoresis gels. For Southernblot analysis, single cell cDNAs were blotted onto Hybond-N+ membranes (Amersham) and probed with $^{32}\alpha P$ dCTP-labelled DNA probes comprising the 3' regions of fragilis, fragilis2 and fragilis3 cDNAs and full length stella cDNA. GAPDH was used as loading control. Blotting signal was detected using a Fuji film FLA 5000 scanner. Signal strength was quantified in relation to GAPDH signal, whereby relative gene expression was calculated as ratio of gene signal to GAPDH signal and this ratio was subsequently normalized by division through the highest hybridisation signal per blot. For dotblot analysis, full length fragilis cDNAs were blotted and probed with $^{32}\alpha P$ dCTP-labelled 3' probes.

Example 16

The Fragilis Gene Family

Figure 9:
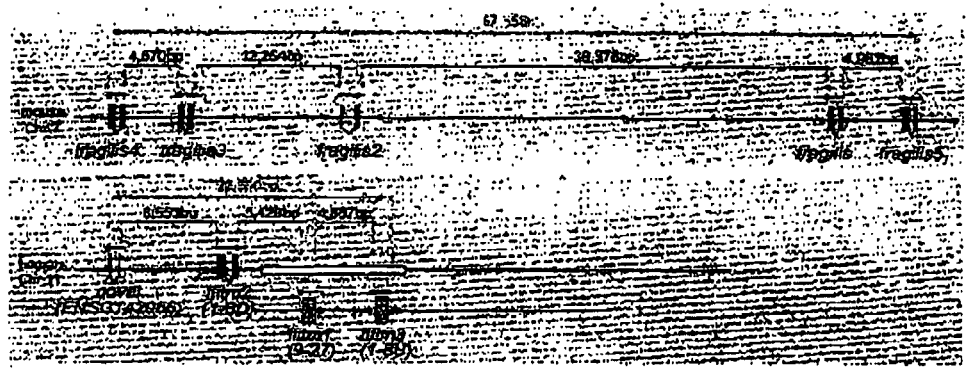
FIG. 9. The Fragilis family cluster on mouse Chr7, and the human homologues in the syntenic region on Chr11. In the mouse, the five Fragilis genes are clustered within a 70 kb region. All genes are encoded by two exons, and apart from fragilis2, they are located on the minus strand. In human, the four homologous genes, ENSG142056 and Ifitm1 (9-27), Ifitm2 (1-8D) and Ifitm3 (1-8U), are clustered within a 25 kb stretch. The four human homologues are each encoded by two exons, but the length of the intronic sequence for Ifitm1 and Ifitm3 is not known. Apart Ifitm2, all human genes are encoded on the minus strand. The green circles represent ISRE consensus sequences.

Using the cDNA sequence of fragilis as a template to search the ensembl genome browser (www.ensembl.org), we identified eight mouse genes with moderate to high DNA sequence similarity to fragilis (45-74%). ESTs from a variety of embryonic and adult tissues have been reported for five of these genes, of which four possess a two-exon structure similar to fragilis. Analysis of the genomic location of the latter revealed that the four genes cluster around the fragilis locus within a 70 kb region on the distal tip of mouse Chr 7 (F5). We therefore named the four novel genes fragilis2-5, reflecting their genomic location, similarity to fragilis and germ cell associated expression pattern (see below; FIG. 9). The four remaining putative genes that we detected have few or mostly no reported ESTs and are coded by a single exon unlike fragilis. We therefore consider them to be pseudogenes.

To determine whether the Fragilis genes are evolutionary conserved, we have identified four homologues of mouse Fragilis in the human genome on Chr 11 (p15.5), a region which is indeed syntenic to the Fragilis family locus on mouse Chr 7 (FIG. 9). Three of these genes, Ifitm1 (9-27), Ifitm2 (1-8D) and Ifitm3 (1-8U), share 58-65% similarity to the fragilis gene cluster and are located within an 18 kb genomic stretch [11]. They are responsive to type1/2 interferons and code for interferon induced transmembrane (Ifitm) proteins, involved in antiproliferative signalling and homotypic cell adhesion [12-15]. The fourth gene, ENSG142056, a novel gene with two exons, is highly similar to mouse fragilis4 (83% DNA sequence similarity) and neighbours Ifitm2. The human Fragilis family homologues hence form a similar genomic cluster as the five Fragilis genes in the mouse. Phylogenetic tree analysis suggests however, that only two Fragilis genes, fragilis4 and either fragilis, fragilis2 or fragilis3, have been conserved from mouse to human (data not shown). Subsequent gene duplications may therefore have occurred independently in both species. We also identified two Fragilis family-like genes in cow (bovine 1-8U, bovine 9-27) and four genes in rat (P26376, JC1241, NP110460, AAD48010). While the rat genes have been annotated as putative interferon inducible, the two bovine genes that are similar to the human Ifitm genes, have been reported to respond to interferon signalling [16, 17]. Due to limited mapping information of the cow and rat genomes, we cannot, at this stage, deduce whether these homologous genes are also organised in a cluster. Interferon stimulable response elements (ISREs, GGAAAN(N)GAAAC (SEQ ID NO:58)) within the human Ifitm locus confer the responsiveness of the three human Ifitm genes to interferons [11, 18]. Similar ISRE consensus sequences are also found within the Fragilis family cluster in the mouse, associated in particular with fragilis, fragilis 2 and fragilis5 (FIG. 9).

Figure 10:
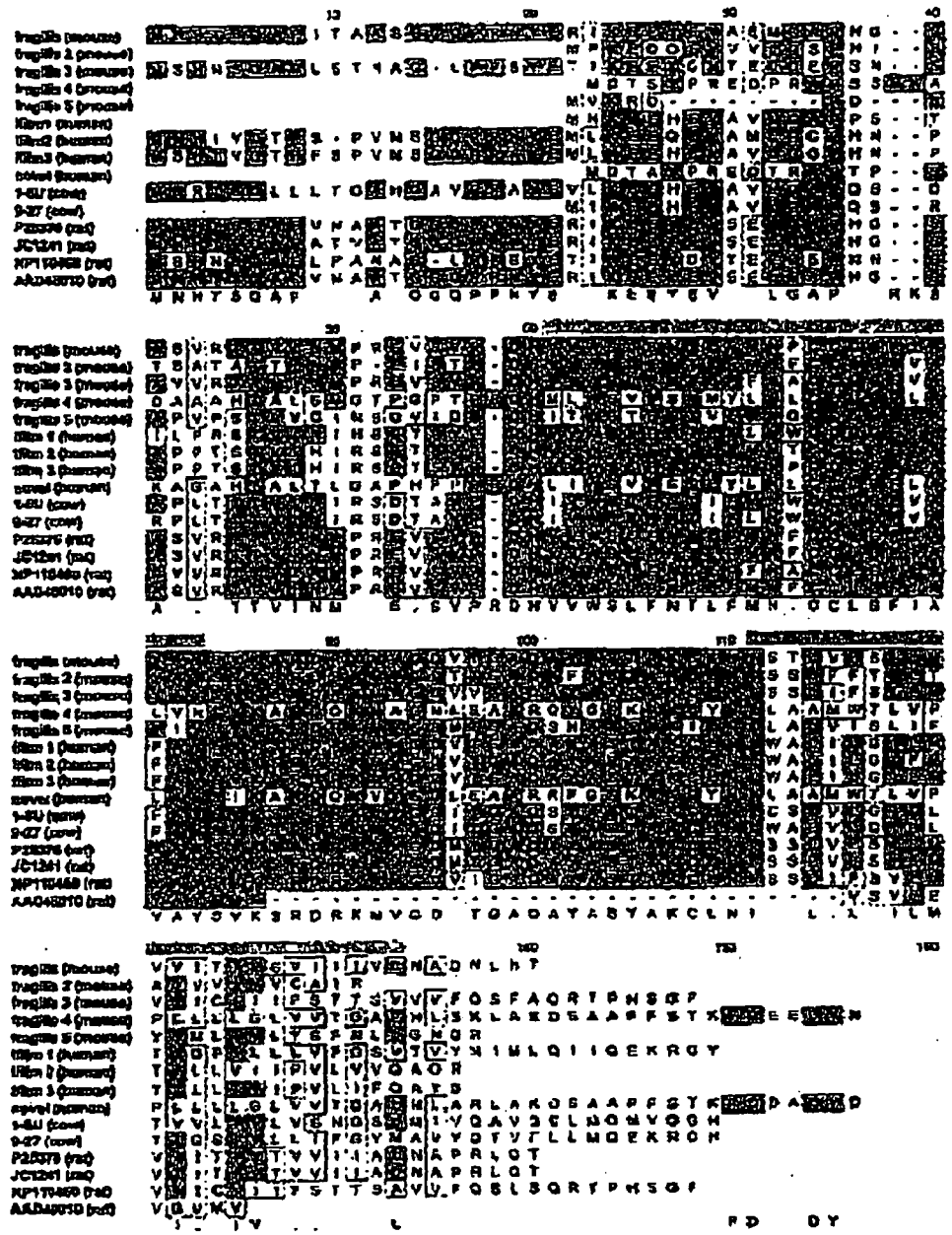
FIG. 10. Protein alignment of the Fragilis family and their homologues in human, cow and rat. Green bars indicate the location of the two predicted transmembrane domains, of which the first as well as the inter-domain stretch appear to be highly conserved throughout the four mammalian species. Identical amino acids are highlighted in dark grey, similar amino acids in light grey. The alignment was done using ClustlW.

The murine family of fragilis and related genes code for five highly similar transcripts of 104 to 144 amino acids, each containing two predicted transmembrane domains (FIG. 10). The sequence similarity to human, cow and rat fragilis-like genes is equally high (overall 68% amino acid similarity). It should be noted, that the first transmembrane domain as well as the following stretch to the beginning of the second transmembrane domain constitute the regions of highest intra- and inter-species conservation.

Example 17

Figure 11:
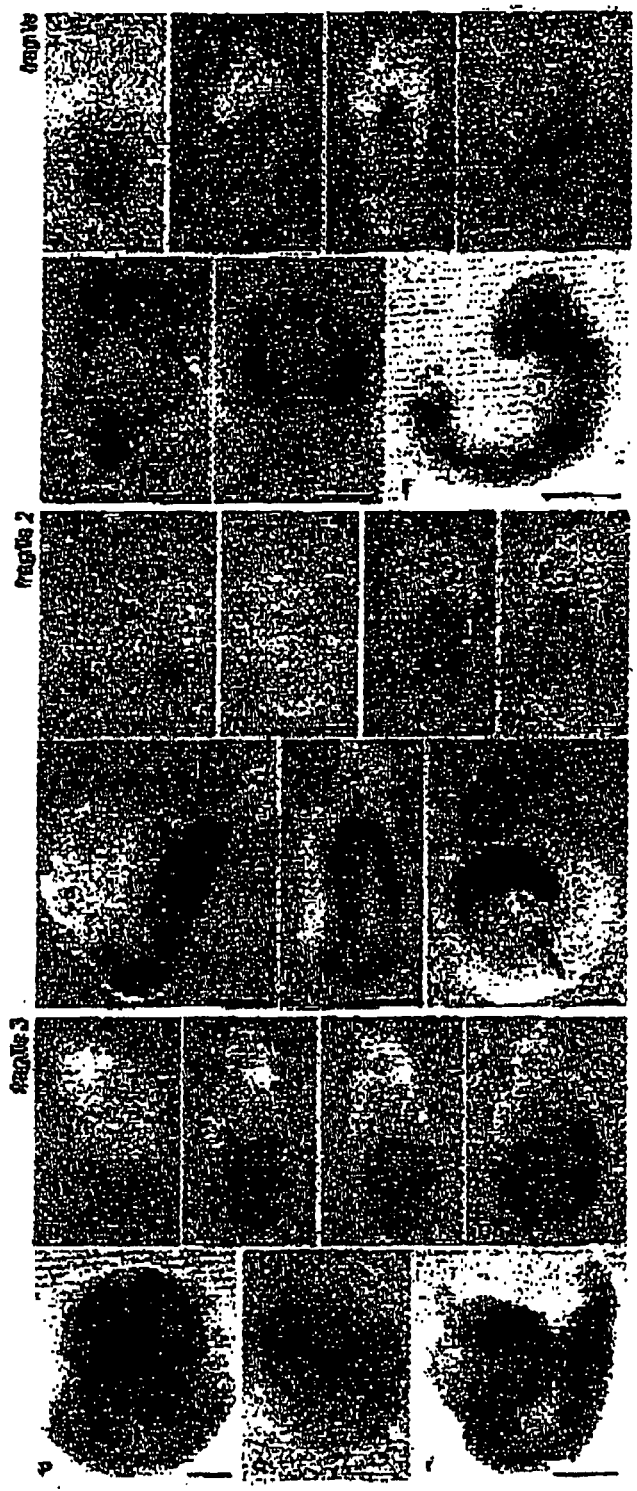
FIG. 11. Expression analysis of fragilis (a-f), fragilis2 (g-l) and fragilis3 (m-r) by whole mount in situ hybridisation. Pictures are taken as lateral view unless otherwise stated, with anterior to the left and posterior to the right. fragilis is expressed throughout the epiblast in E5.5 embryos (a) and in the region of germ cell specification at the base of the incipient and early allantoic bud at E7.5 (b, b' posterior view, c). At E8.5, signal is detected at the base and in the proximal third of the allantois as well as in the latero-anterior aspects of the brain (d superior view, e anterior view). At E9.5, fragilis appears expressed in a population of cells at the beginning of the invaginating hindgut (arrow in f), as well as in the pharyngeal arches (f). fragilis2 is detected throughout the epiblast at E5.5 (g). Expression seems thereafter downregulated but becomes again detectable in the posterior mesoderm and at the base of the incipient and growing allantoic bud in E7.0 and E7.5 embryos (h, i, i' posterior view). At E8.5, expression is seen in caudal mesoderm (j, k posterior view), while at E9.5 expression is seen in the tailbud, the mesoderm caudal to the $12^{th}$ somite and the lung primordia (arrow, 1). fragilis3 is expressed throughout the epiblast at E6.5 (m) and around E7.5 additionally in the region of PGC specification (n, n' posterior view, o). At E8.5, fragilis2 expression is seen throughout the embryo, with exception of the developing heart, and appears intense in single cells (arrow in q posterior view) at the base and within the proximal region of the allantois (p posterior view, q, r). asterix: allantois; black arrowhead: allantoic bud; white arrowhead: developing heart; scale bars: 100 μm (a, b, g-i, m, n); 200 μm (c-e, o-q); 400 μm (f, j-l, r).
Figure 12:
FIG. 12. Expression analysis of fragilis2 by in situ hybridisation on sections. (a-d) transverse sections through the caudal region of an embryo at E9.5 (approx. 25 somites) at progressively rostral levels. At most caudal levels, fragilis2 expression is seen in cells of the neural tube, in the presomitic mesoderm, in single cells within the hindgut (arrowhead) and in the body wall. (b) staining at approx. $23_{rd}$ somite level is present within the forming somite, the body wall mesoderm and cells within the hindgut as well as the floorplate. (c) at approx. $21_{st}$ somite level, expression in the differentiating somites is reduced, while cells in the floor plate and within the hindgut remain fragilis2 mRNA positive. (d) at approx. the $13_{th}$ somite level, fragilis2 expression is absent from the somatic mesoderm as well as the neural tube. (e) sagittal section through an E10.5 embryo shows fragilis2 expression in developing lung tissue (asterix; higher magnification in f) and migrating cells along the hindgut anterior to the dorsal aorta (arrow). (g) shows a magnified view of fragilis2 mRNA expressing, migrating cells. da: dorsal aorta; fp: floor plate; g: gut; h: developing heart; nt: neural tube; s: somite; bw: body wall; scale bars: 150 μm (a-d); 1 mm (e); 400 μm (f, g).

Fragilis, Fragilis2 and Fragilis3 are Expressed During Early Post-implantation Development We analysed the expression pattern of the five Fragilis family genes by whole mount in situ hybridisation using probes that span the 3' region (150-200 bp) of the corresponding mRNAs. These probes show no significant cross-hybridization between members of the Fragilis family as judged by dotblot analysis (data not shown). As reported, we saw expression of fragilis restricted to the epiblast at E5.5 and E6.5. More importantly, around E7.5, expression of fragilis is intense within a population of cells at the base of the allantois in the region where PGC specification occurs (FIG. 11*a-c*) [8]. fragilis2 and fragilis3 are also expressed within the epiblast of E5.5 embryos (FIG. 11*g*, data not shown). While expression of fragilis2 is thereafter significantly down-regulated, fragilis3 remains expressed at a similar level in the embryonic tissues. At E7.5, fragilis2 is detected in the posterior mesoderm, while fragilis3 expression is seen throughout the epiblast. More significantly, like fragilis, both fragilis2 and fragilis3 show high expression in the region where the cluster of nascent PGCs originates (FIG. 11 *i/i',n/n'*). Thus, these three members of the Fragilis family show significant expression at the time and site of PGC specification.

At E8.5, fragilis expression is seen in cells at the base and within the proximal third of the allantois (FIG. 11*d*). Additionally, a signal is detected in the latero-anterior aspects of the developing brain (FIG. 11*e*). At this stage, fragilis2 is expressed in the mesoderm in the caudal half of the embryo (FIG. 11*j,k*), whereas fragilis3 appears present throughout the entire embryo with the exception of the developing heart (FIG. 11*p-r*). It is noteworthy, that expression seems significantly stronger in single cells at the base and within the proximal third of the allantois at this stage (FIG. 11*q*). At E9.5, when PGCs have started to migrate along the hindgut, fragilis signal is seen in a population of cells located at the beginning of the invaginated hindgut. In addition, the signal appears enhanced in the pharyngeal arches (FIG. 11*f*). At this stage, fragilis2 expression appears restricted to the tailbud, the mesoderm caudal to the $12^{th}$ somite and the lung primordium (FIG. 11*l*).

In contrast to the first three members of the family, neither fragilis4 nor fragilis5 showed expression at early post-implantation stages (E7.0-E8.5, data not shown). Consequently, only the three genes at the centre of the family cluster, that is fragilis, fragilis2 and fragilis3 are expressed in the embryo between E5.5 and E9.5. While their expression pattern is distinct, there is a striking overlap within the region where founder germ cells are located. This suggests that the three neighbouring genes, fragilis, fragilis2 and fragilis3, may share regulatory elements that are likely to be present within the cluster. These regulatory elements may also be responsible for the genes' overlapping expression pattern specifically around the region of nascent PGCs.

Example 18

Figure 13:
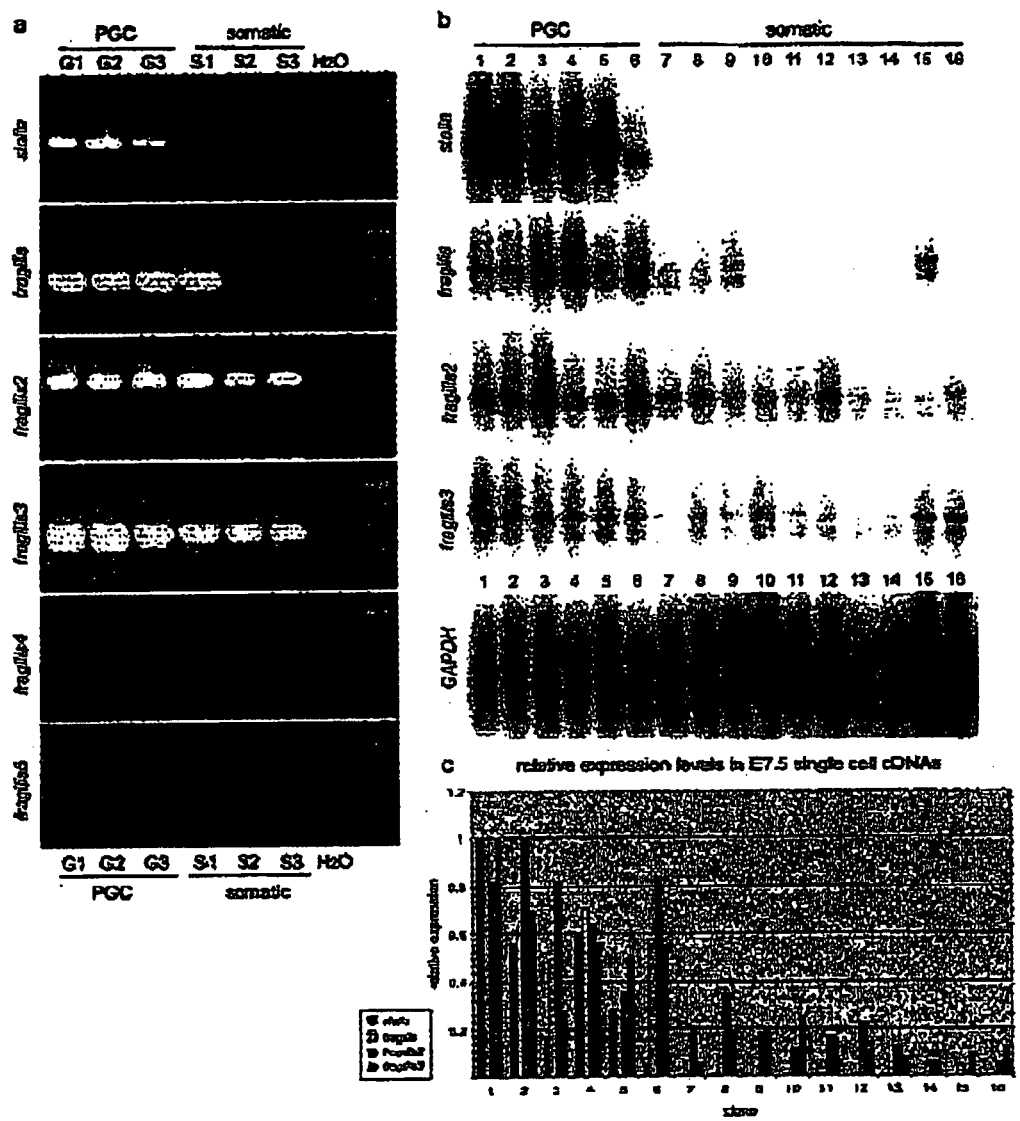
FIG. 13. Expression analysis of the Fragilis family genes in single cells from the region of germ cell specification of E7.5 embryos. (a) shows PCR analysis of cDNAs from three nascent, stella positive PGCs and three surrounding, stella negative somatic cells. Note that fragilis, fragilis2 and fragilis3 are expressed in PGCs and somatic cells, while fragilis4 and fragilis5 are not detected in any of the cells. (b) shows expression of fragilis, fragilis2 and fragilis3 in single cell cDNAs using Southernblot analysis. GAPDH was used as blotting control. (c) Semi-quantitative expression analysis of the Southernblot data shows that all three Fragilis genes are predominantly expressed in nascent PGCs compared to the somatic cells within the region.

Single Cell Analysis of Fragilis, Fragilis2 and Fragilis3 in PGCs and Somatic Neighbours To obtain more precise information on the expression of the new Fragilis family members in the context of germ cell specification, we tested single cell cDNAs from PGCs and surrounding somatic cells sited at the base of the incipient allantoic bud in E7.5 embryos. Both fragilis2 and fragilis3 were expressed in nascent PGCs, which show transcription of the germ cell marker stella/PGC7 (FIG. 13*a*) [8,10]. The two Fragilis family members were also detected in surrounding somatic cells that lack expression of stella/PGC7 [8]. Importantly, semi-quantitative analysis using Southernblotting showed that fragilis2 and fragilis3 are expressed predominantly and at higher levels in nascent PGCs compared to the neighbouring somatic cells (FIG. 13*b,c*). This mimics the pattern seen for fragilis, although expression of the latter is more specific to germ cells. Combined with the in situ hybridisation data, these observations further support the notion that certain common control elements may be involved in the upregulated expression of the three Fragilis genes in the founder PGCs.

Figure 14:
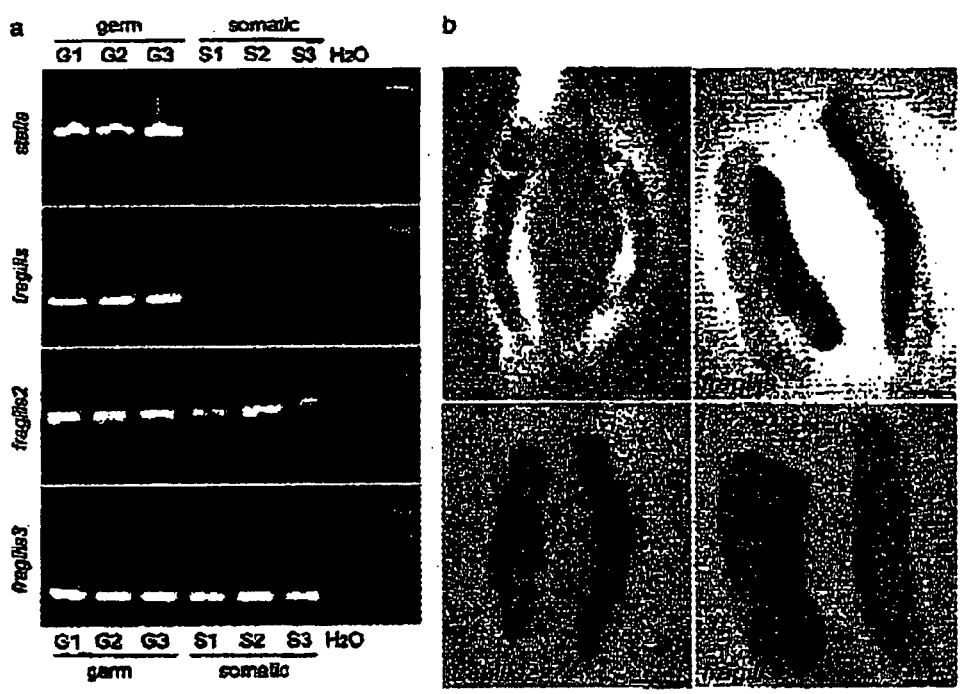
FIG. 14. Expression analysis of fragilis, fragilis2 and fragilis3 at E11.5/E12.5 in single cells from the genital ridge and by in situ hybridisation. (a) shows PCR analysis of cDNAs from three gonadal stella-positive germ cells and three surrounding, stella-negative somatic cells. While fragilis is detected only in the three germ cell clones, fragilis2 and fragilis3 are expressed in the germ cells as well as the somatic cells. (b) shows in situ hybridisation of urogenital ridges of E11.5/E12.5 embryos. While fragilis3 is expressed in the mesonephros as well as the genital ridge, fragilis and fragilis2 are restricted to the genital ridge. The staining pattern for fragilis appears punctuate and restricted to single cells mimicking the pattern seen for the germ cell-specific stella gene. asterix: genital ridge; black arrowhead: mesonephros; scale bars: 400 μm.

During the developmental stages directly subsequent to PGC specification, all three Fragilis family genes are expressed in a population of cells associated with the allantois and in a location where premigrating PGCs are thought to reside (FIG. 11*d,k,q*). The precise gene expression during migration of PGCs is not clear at this stage from our analysis. However, using in situ hybridisation and PCR analysis of cDNAs from single cells within the genital ridge, we found clear expression of fragilis, fragilis2 and fragilis3 in the gonadal germ cells at E11.5-12.5 (FIG. 14). While fragilis3 expression extends to the mesonephros, fragilis and fragilis2 signal was restricted to the genital ridge. A punctuate staining pattern was seen for fragilis, mimicking the germ cell restricted expression of stella/PGC7 (FIG. 14*b*). This pattern in addition to the PCR analysis suggests that fragilis is expressed predominantly if not solely in germ cells at E11.5. As was the case in earlier embryos, neither fragilis4 nor fragilis5 were detected in gonadal germ cells (data not shown).

Example 19

Discussion

In this study we describe the identification of the murine Fragilis gene family, which appears to be conserved amongst mammalian species, and whose members code for five highly similar transmembrane proteins. Three members of the Fragilis family, fragilis, fragilis2 and fragilis3, exhibit expression, which is associated with germ cell specification and development. Located at the cell membrane, the Fragilis proteins may be crucial for mediating interactions amongst germ cells and their surrounding neighbours. While the three genes are expressed earlier at E5.5 and thereafter to a varying extent, they all show upregulation of expression within nascent PGCs. It is likely that a cis control element exists within the locus that is required for this expression, which continues within gonadal PGCs. Future studies will elucidate where these control elements are located and how they regulate expression of the fragilis-related genes.

Although the five Fragilis family members are clustered within a small genomic region, it appears that neither fragilis4 or fragilis5 show expression in early embryos or embryonic germ cells. It is striking that these two members are located at the periphery of the cluster in contrast to the centrally located fragilis, fragilis2 and fragilis3 genes. This lack of expression may be due to the presence of boundary elements, which might restrict the action of control elements to genes present within the centre of the cluster. Since sequence comparison suggests that gene duplications may have occurred independently in the two species, it appears that a certain evolutionary constrain may exist on duplication and maintenance of the duplicated genes within immediate neighbourhood. Since the four human homologues of the Fragilis family in the syntenic region are also arranged in a genomic cluster and are highly similar to the family genes, it is tempting to suggest that they may also serve similar functions as in the mouse.

The presence of several interferon stimulable response element (ISRE) consensus sequences within the Fragilis locus, together with the similarity of the genes to their interferon-inducible human and bovine counterparts, suggest very strongly that fragilis and the fragilis-related genes are responsive to interferons. Indeed, the ISRE tandem repeat present in the 5' flanking region of human Ifitm1, Ifitm2 and Iitm3 genes is also present in the 5' flanking region of fragilis exon 1 [11]. Interferons, as secreted signalling molecules, have so far been implicated mainly in the process of immune response, the inhibition of cellular growth and the control of apoptosis [19]. Although interferons are expressed in the post-implantation embryo, their role during development has not been addressed in detail [20, 21]. Our studies have pointed to a possible involvement of interferons in germ cell development. Future work will determine whether the Fragilis genes respond to interferon signals in all or some instances where the genes are expressed, which we expect in view of the presence of conserved ISRE elements in the mouse and human loci.

Example 20

Conclusion

We have identified the Fragilis family of interferon inducible genes, which code for transmembrane proteins. The five members are arranged in a cluster within a genomic region of 70 kb in the mouse that also contains ISRE elements. The centrally located fragilis, fragilis2 and fragilis3 genes are of particular interest, because they are expressed in the region where germ cell specification occurs. The family is evolutionary conserved amongst mammalian species where it may serve similar functions. Detailed studies of the Fragilis family may also show what role interferons have in embryonic development.

Example 21

Stella is a Maternal Effect Gene Required for Normal Early Development in Mice

In this and the following Examples (Examples 21 to 25), we have investigated the effects of a targeted mutation of stella in mice. Maternal inheritance in mammalian oocytes includes proteins important for totipotency and epigenetic modifications[1], as well as factors crucial for early development, which are transcribed from so called maternal effect genes[2-7].

Amongst these maternally inherited proteins is Stella, which is also expressed in preimplantation embryos, primordial germ cells, and pluripotent cells[8,9]. We show that while matings between heterozygous animals resulted in the birth of apparently normal stella-null offspring, stella-deficient females showed severely reduced fertility, which is due to a lack of maternally inherited Stella in their oocytes.

Stella is a maternal effect gene, as the phenotypic effect on embryonic development is a consequence of the maternal stella mutant genotype. Indeed, we demonstrate that embryos lacking Stella-protein are compromised in preimplantation development and rarely reach the blastocyst stage. Furthermore, we show that STELLA that is expressed in human oocytes[10] is also expressed in human pluripotent cells and in germ cell tumours. Interestingly, human chromosome 12p, which harbours STELLA is consistently overrepresented in these tumours[11]. These findings suggest a similar role for STELLA during early human development as in mice and a potential involvement in germ cell tumours.

The aim of this study was to determine the role of stella by loss of function analysis in mice. In our previous work, we have shown that expression of stella (also called PGC7) is activated during the process of germ cell specification at E7.25 specifically in the founder population of lineage restricted primordial germ cells (PGCs)[8,9]. Thereafter it is expressed in the germ line until about E15.5 in male and E13.5 in female gonads. Expression of stella resumes in the immature oocytes in newborn ovaries, and it is subsequently detected in maturing oocytes and in preimplantation embryos (FIG. 15a-l)[8]. Soon after the formation of the zygote, Stella accumulates in the pronuclei, although it is also detected in the cytoplasm (FIG. 15d-f). Both cytoplasmic and nuclear staining continues during cleavage stages until the blastocyst stage, after which Stella is downregulated (FIG. 15g-l and data not shown)[8], until its re-appearance in the nascent PGCs[8,9].

Example 22

Materials and Methods

Immunofluorescence

Embryos were fixed in 4% paraformaldehyde for 15 minutes, washed 3 times with PBS and permeabilised in AB-buffer (1% Triton-X100, 0.2% SDS, 10 mg/ml BSA in PBS), which was also used for the following antibody incubations and washes. They were then incubated in primary antibody (anti-Stella[9] 1:200, anti-PGC7[8] 1:2000) overnight at 4° C., washed 3 times and incubated with secondary antibody for 1-2 hours at room-temperature (Alexa 564, Molecular probes, 1:500). After 3 further washes in AB-buffer, embryos were rinsed once in PBS and incubated at 37° C. with 0.1 mg/ml Rnase A (Roche) in PBS for 30 minutes. Finally embryos were incubated for 10 minutes in PBS with propidium iodide (2 µg/ml) and mounted on slides in Vectashield (Vector Laboratories) mounting medium, which also contained propidium iodide.

For E11.5 PGC-stainings, genital ridges were washed in PBS, treated for 10 minutes at 37° C. with Trypsin/EDTA (Gibco), diluted in PBS and dissociated into a cell suspension. Cells were allowed to settle down on poly-L-lysine treated slides and fixed with 3% formaldehyde for 15 minutes. After permeabilisation with 0.2% Triton X-100 in PBS and 3 washes in PBS cells were blocked with 3% BSA in PBS (also used for subsequent washes and antibody dilutions) for 40 minutes and incubated with primary antibodies (anti-Stella 1:100, anti-SSEA1 (=TG1), P. Beverley 1:2) overnight at 4° C. Then the cells were washed and incubated with secondary antibodies (Alexa 564, Alexa 488, Molecular probes, 1:500) for 1.5 hours. After washing, Rnase (0.1 mg/ml) treatment was done for 1 hour at room temperature and the cells were mounted with Vectashield containing Toto-3 (Molecular probes, 1:1000).

Immunofluorescence was visualized on a BioRad Radiance 2000 confocal microscope.

Identification of Stella-homologues

Human STELLA was identified by blasting the mouse Stella protein sequence against the translated human genome sequence using the Ensembl server (http://www.ensembl.org). The only hit showing the same intron-exon structure as the mouse gene is located on the syntenic region (FIG. 15$m,n$) and was therefore considered to be the human orthologue (hits without introns were considered as pseudogenes). Three IMAGE-EST clones (Genbank IDs: AA927342, AI066520, AA564230; UniGene cluster Hs.131358), which aligned to the genomic region, were fully sequenced by us to confirm the predicted sequence.

The putative rat-stella sequence was mapped as above and deduced from the alignment of the mouse cDNA sequence with the syntenic rat genome sequence.

RT-PCR Analysis of Human Tissues

1 µg total RNA of each human tissue (source: Ambion and see acknowledgements) was reverse transcribed into $1^{st}$ strand cDNA with Superscript II reverse transcriptase (Gibco) for 1 hour at 37° C. 1 µl of this cDNA was amplified by a 30 cycle PCR-reaction using primers for human STELLA (5'-CAATTTGAGGCTCTGTCATCAG-3' (SEQ ID NO:59), 5'-TCATCTCACTGACTTTGGGC-3' (SEQ ID NO:60)) or ribosomal protein L32 (5'-AGTTCCTGGTCCA-CAACGTC-3' (SEQ ID NO:61), 5'-TGCACATGAGCTGC-CTACTC-3' (SEQ ID NO:62)).

ES-cell Manipulation and Knockout Verification

The targeting construct consisted of 1.5 kb of upstream and 4.1 kb of downstream genomic sequence flanking the second exon of stella. The 5' arm terminated after the first 32 bp of exon 2, which was fused to an IRES lacZ reporter, followed by a promoted neo selectable marker. The construct was linearized and electroporated into CCB mouse embryonic stem (ES) cells which were placed under selection. Individual G418-resistant clones were picked and screened for correct integration of the targeting construct by PCR using a vector primer and a primer external to the 5' arm. 288 clones were screened of which two exhibited the expected size bands in the PCR. Homologous recombination was also confirmed by Southern blot using 5', 3' and neo-probes on NcoI and EcoRI digested genomic DNA. The correctly targeted ES-cell clone F4 was injected into MF1 and C57BL/6 blastocycsts to produce chimeric mice. Germline transmission was achieved by breeding the male chimeras with 129Sv/Ev females. All analysis was done on the inbred 129Sv/Ev background. To confirm that the stella gene was correctly inactivated, mice were genotyped by Southern blot as above (FIG. 16$b$). Furthermore we performed RT-PCR (same protocol as for human tissues—see above) on testis and ovary RNA of wt, heterozygous and homozygous mice (FIG. 16$c$), using exon 2-specific primers (5'-AGACGTCCTACAACCAGAAAC-3' (SEQ ID NO:63), 5'-CCGAACAAGTCTTCTCATCTT-3' (SEQ ID NO:64)).

Counting of Primordial Germ Cells

Embryos of stella-heterozygous intercrosses were dissected out at E8.5, fixed with 4% paraformaldehyde and stained for TNAP-positive PGCs with α-naphthyl phosphate/fast red TR solution (Sigma) as previously described [20,26]. The posterior parts of the embryos were flattened under coverslips and used for counting PGCs, while the anterior parts were used for genotyping by PCR.

Histology

Testes and ovaries from adult mice were fixed in Bouin's fixative at 4° C. overnight and washed thoroughly in 80% ethanol. After dehydration through an ethanol series they were transferred into xylene and embedded in Paraplast Plus wax (Sigma). 8 µm sections were cut, rehydrated and stained with Ehrlich's Haematoxilin (BDH) and 1% eosin (Sigma). After dehydration, slides were mounted with DPX (BDH).

Matings and In Vitro Culture

All studies for the assessment of fertility and embryonic development were done using natural matings. Mice were kept on a constant light/dark cycle and mating was assumed to have happened in the middle of the dark period before a vaginal plug was detected (E0.5=midday on day of plug). Embryos were collected by flushing oviducts/uteri at the time of the observed stages (E0.5-E3.5) or at E1.5, if they were cultured. Culturing was done under 5% $CO_2$ in KSOM medium.

Work on animals was performed under Home Office project licences PPL80/1280 and PPL80/1706.

Generation of Stella-GFP Mice

Using the stella-cDNA as a probe, we screened a gridded genomic 129 pBeloBAC library (Genome Systems St Louis, Mo.) to identify a clone harbouring the stella locus. We subcloned 11.5 kb of genomic sequence including about 8.5 kb upstream sequence and exon 1, intron 1 and the start of exon 2 and fused it in frame to eGFP (Clontech) and a SV40-polyadenylation signal. This sequence was then injected into pronuclei of B6CBA F2 zygotes, to generate transgenic mice. The transgene was maintained on the same genetic background and the onset of expression of the paternal allele was observed by mating stella-GFP transgenic males with non-transgenic females.

The cDNAs of the Stella homologues mentioned in this study have the following GenBank accession numbers: mouse Stella (AY082485), rat Stella (BK001414, pending), human STELLA (AY317075, pending).

Example 23

Stella Homologues

Figure 15:
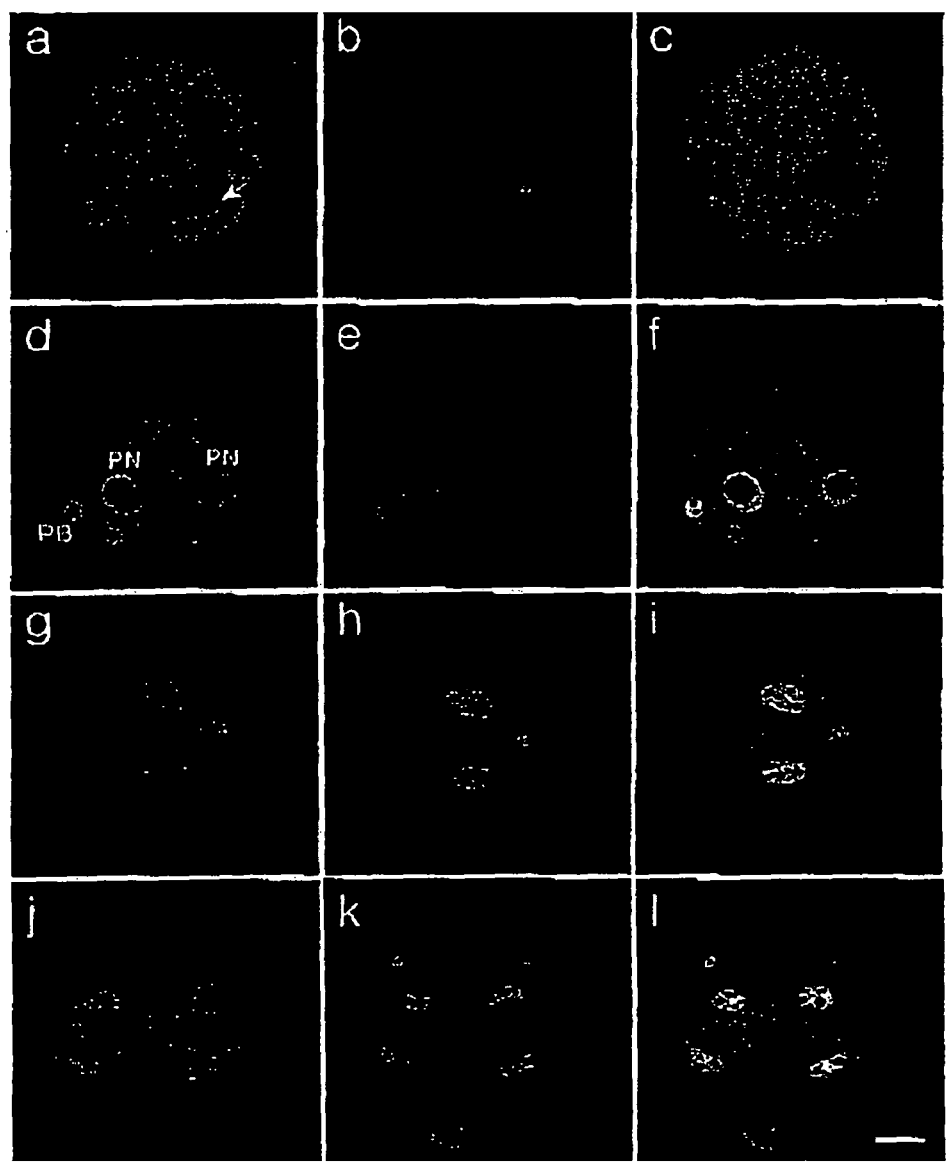
FIG. 15. Stella expression during preimplantation development and evolutionary conservation. a-l, Confocal sections of anti-stella (a,d,g,j) and propidium iodide (b,e,h,k) stained embryos (c,f,i,l merged images). Maternal stella is stored in the unfertilised egg (a-c) (arrow, exclusion of Stella from condensed metaphase chromosomes) and localizes both to the cytoplasm and pronuclei (PN) after fertilisation (d-f; PB, polar body). Also during later stages (2-cell, g-i; 4-cell, j-l) it can be seen both in the cytoplasm and the nucleus. Scale bar=20 μm. Synteny (m) of the stella gene in mouse, rat and human and close up view (n) of stella and its neighbouring genes in mouse and human. Arrows indicate the direction of transcription. o, Alignment of Stella protein sequences. Identical amino acids have a black background and similar amino acids a grey one. Putative nuclear export and localisation signals are marked by red and black lines, respectively. The red stars indicate conserved hydrophobic amino acids, which are typical for nuclear export signals[27]. p, RT-PCR analysis of STELLA-expression in human pluripotent cells and reproductive organs. RPL32 was used as control. ES, embryonic stem cells; EC, embryonic carcinoma cells (nTera2); tet, testis tumor; te, normal testis; ov, normal ovary; –Rt, without reverse transcriptase; 0, water control.

We have now identified stella homologues in the rat and human genomes, which show the same exon-intron structure, and are located within the syntenic chromosomal regions (see FIG. 15$m,n$). The mouse gene is in position F2 of chromosome 6, the rat gene on q42 of chromosome 4 and the human gene on p13.31 of chromosome 12. Only one expressed-sequence tag (EST) (BI289609, aorta pool) was found in the rat, while several human ESTs mainly from germ cell tumour libraries (UniGene cluster Hs. 131358) matched the genomic sequence. The full-length amino acid sequences (FIG. 15$o$) of the mouse and rat protein showed 70% identity (84% similarity), but the mouse and human proteins shared only 35% identity (53% similarity). While the Stella orthologues of rodents and humans have clearly diverged, conserved sequence stretches are found in the centre and the C-termini of the proteins. The biochemical function of these motifs remains to be discovered, but some of the predicted nuclear localisation and export signals reside within the regions of higher conservation.

Example 24

Expression of Stella

Figure 15N:
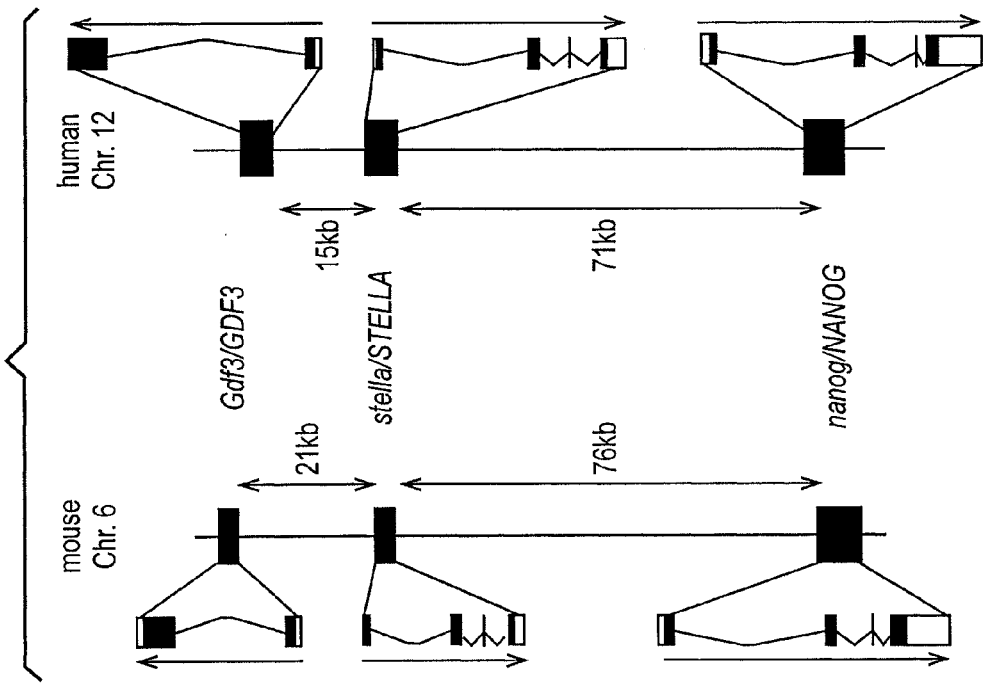
Figure 15M:
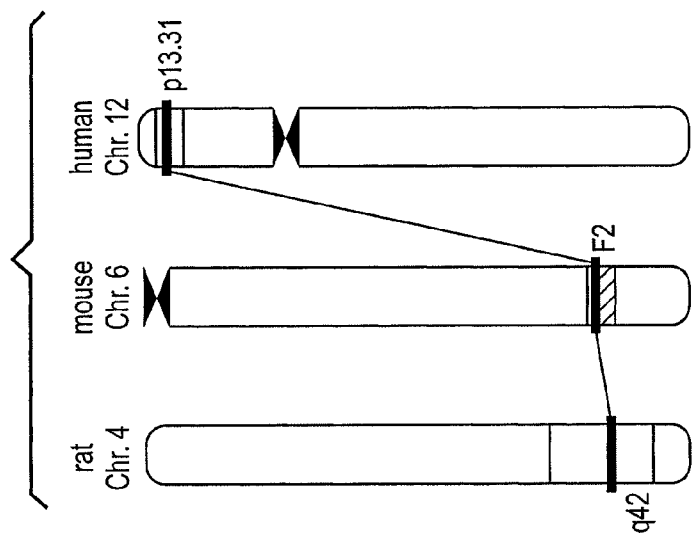
Figure 15P:
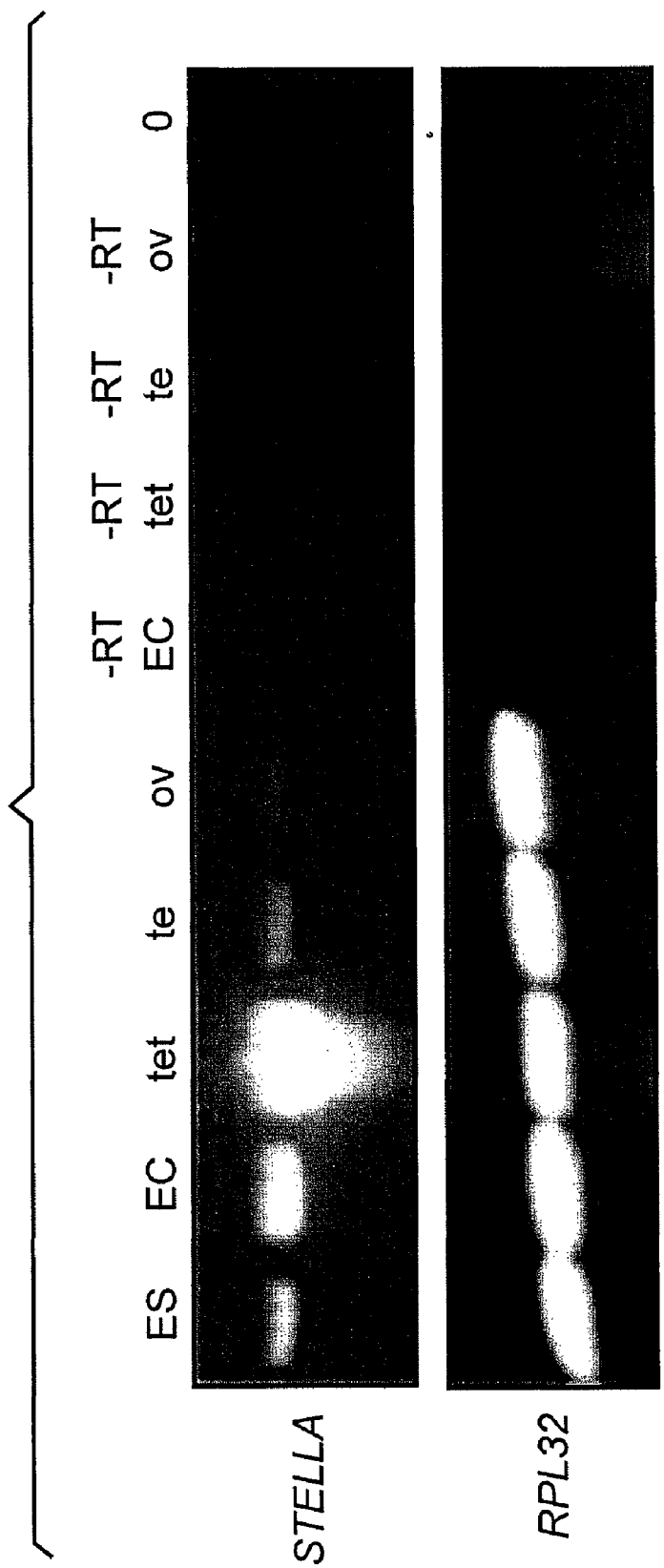

To study the expression of human STELLA, we performed RT-PCR analysis on pluripotent cell lines and reproductive organs (FIG. 15p). We detected STELLA in human embryonic stem (ES) cells and embryonic carcinoma (EC) cells, as well as in normal testis and ovary. The strongest expression was found in a testicular germ cell tumour, which shows characteristics of pluripotency[11]. Expression of STELLA in other tumours and somatic tissues was either very low or undetectable (data not shown). Our findings concur with a recent study[10], where STELLA (termed fragment 7.1) was detected in human oocytes and in EC cells, in which it was down-regulated after retinoic acid-induced differentiation. These findings strengthen the hypothesis that STELLA might have a similar role in humans as in mice. Furthermore, the short arm of chromosome 12 (12p) on which STELLA is located, is consistently overrepresented in testicular germ cell tumours[11]. Stella/STELLA resides within a conserved cluster of genes consisting of nanog/NANOG[12,13] and gdf3/GDF3 [14] (FIG. 15n), which are associated with pluripotency and germ cell tumours. The conserved proximity in mice and humans and the overlapping expression patterns of these genes suggest a possible co-regulation at a transcriptional level[15]. Clearly, these findings prompt a careful analysis of the functions of stella and its neighbours in mouse and man.

Example 25

Stella Knockout Mice

To begin to address functions of stella, we generated stella knockout (stella$^{-/-}$) mice (FIG. 16). Matings between heterozygous (stella$^{+/-}$) mice on the 129/SvEv background resulted in the birth of 192 pups consisting of 56 (29.2%) wild-type, 81 (42.2%) stella$^{+/-}$ and 55 (28.6%) stella$^{-/-}$ mice, in the approximate mendelian ratio of 1:2:1. Therefore, stella$^{-/-}$ deficient mice are viable and survive at a normal rate.

Figure 17:
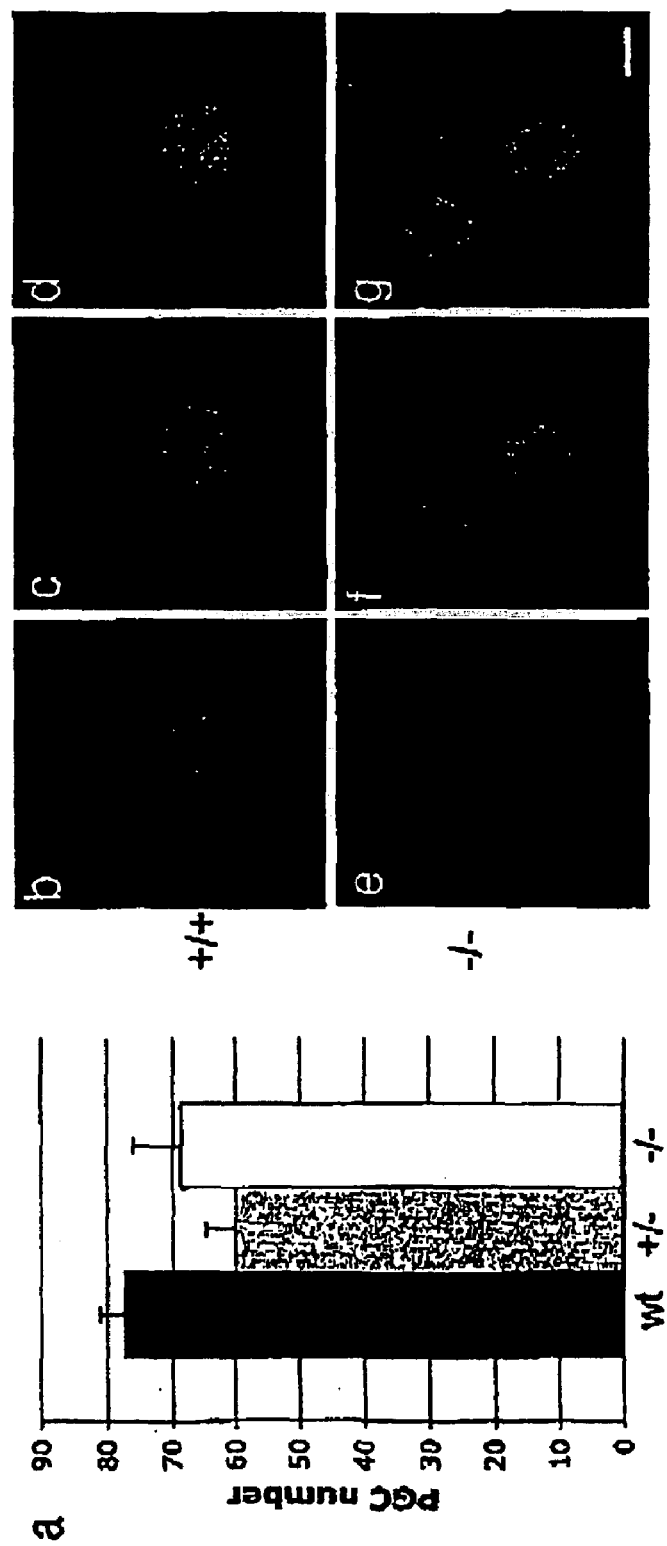
FIG. 17. Germ cell development in stella knockout mice. a, Numbers of PGCs in wild-type (wt, n=9), stella$^{+/-}$ (n=14) and stella$^{-/-}$ (n=7) embryos are not significantly different at E8.5 (0-8 somites). The results are presented as means ±SEM. b-g, Gonadal PGCs (E11.5) stained with anti-stella (b, e) and anti-SSEA1 (c, f) antibodies (d, g merge including Toto3 (blue) as DNA stain). The PGC-marker SSEA1[17] is coexpressed with stella in wild-type PGCs (b-d) and also detectable in stella$^{-/-}$ animals (e-g), showing that PGCs are present in knockout mice. Scale bar=10 μm. Sections of testes (h-j) and ovaries (k-m) of adult wild-type (h, k), stella$_{+/-}$ (i, l) and stella$^{-/-}$ (j, m) mice. Knockout males show normal development of sperm (arrowheads) and knockout females normal ovary morphology with follicles containing oocytes of different stages (arrows). Scale bars in j (for h-j), m (for k-m)=100 μm.
Figure 17:
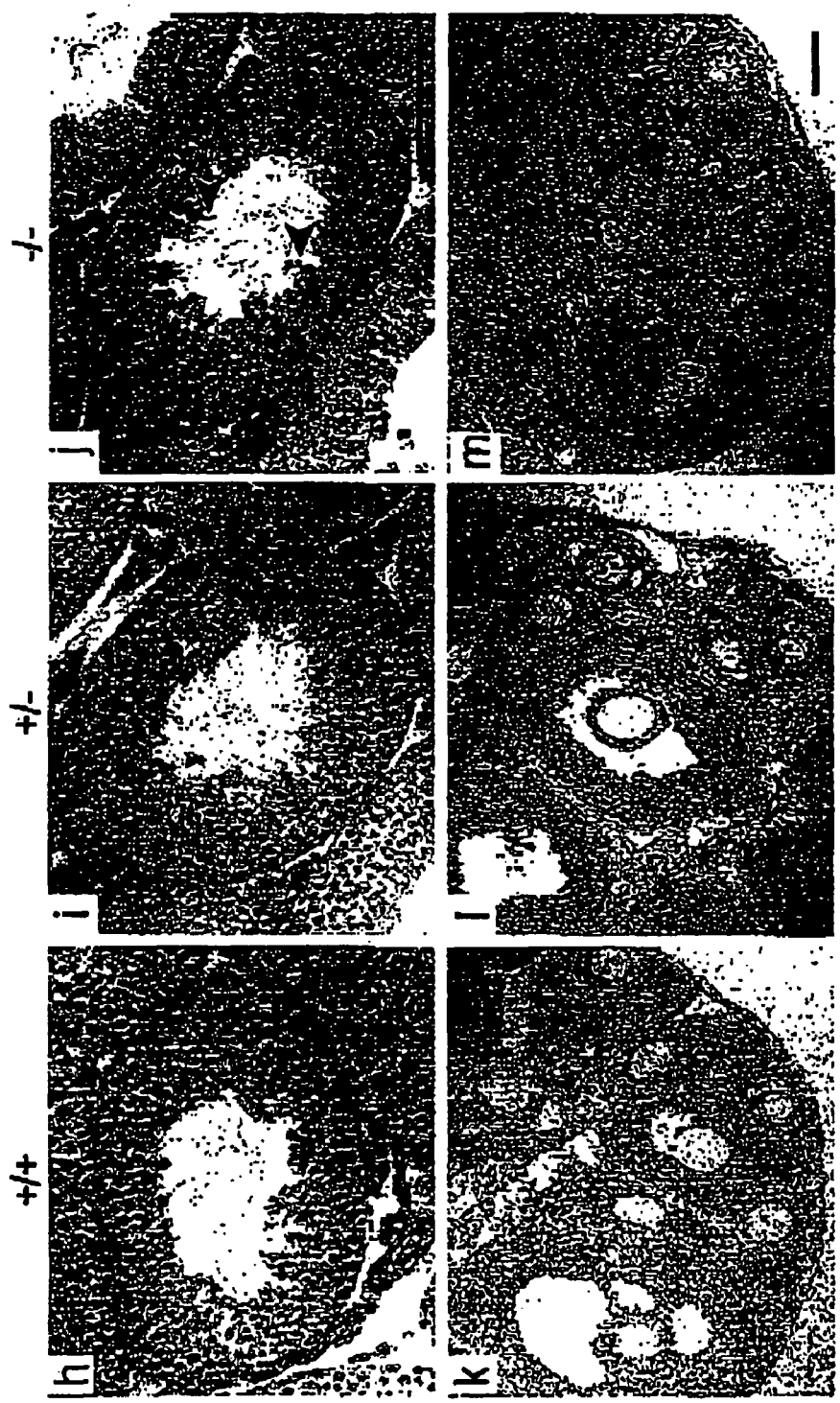

As stella is detected in the founder PGCs, we examined stella$^{-/-}$ mice for any effects on development of germ cells. Examination of germ cells at E8.5 in mutant embryos by tissue non specific alkaline phosphatase (TNAP) activity, a marker of PGCs[16], revealed no significant differences in the numbers of PGCs compared to those in wild-type embryos (FIG. 17a). Similarly we found no effect on early gonadal PGCs (E11.5) in knockout embryos, detected by the germ cell marker SSEA1[17] (FIG. 17b). Furthermore, histological examination of testes and ovaries of adult mice showed no gross abnormalities in the development of gametes in stella mutant animals (FIG. 3h-m). Indeed stella$^{-/-}$ males showed normal fertility when mated with wild-type or heterozygous females. In mutant females, we detected oocytes at all stages of development and we found similar numbers of ovulated oocytes compared to those from control animals (stella$^{-/-}$ 8.6±1.0, n=9; wild-type or stella$^{+/-}$ 9.0±0.4, n=19), suggesting that the loss of stella has no gross effects on either germ cell determination or development.

Figure 18:
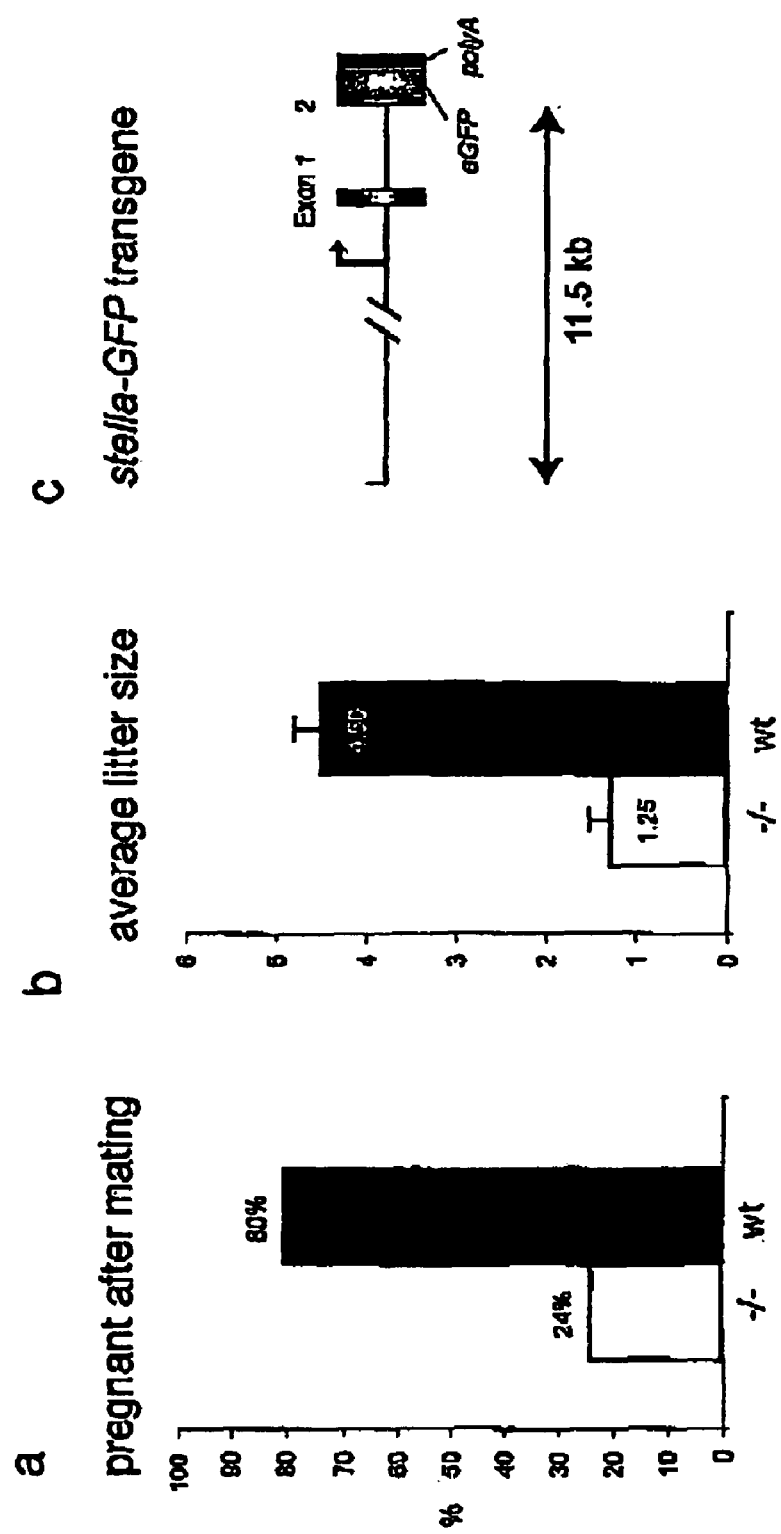
FIG. 18. Maternal effect of the stella knockout and onset of paternal expression of stella during preimplantation development. a, 80% of matings with wild-type males resulted in pregnancies of wild-type females, while in only 24% of the plugs stella$^{-/-}$ females became pregnant. b, From these pregnancies, the littersize was strongly reduced in knockouts compared to wild-type females. c-i, A stella-GFP reporter construct (c) was used to determine, when the paternal allele of stella starts to be expressed. Zygotic expression of the stella-GFP transgene begins at the 2-cell stage (E1.5; e, h) and continues during later stages (E2.5, 4-8 cell; f i). d-f, GFP-fluorescence; g-i, brightfield merged with GFP-image; arrowheads, non-transgenic embryos; arrows, transgenic embryos. Scale bar in d (for d-i)=100 μm. j-l, Confocal section through a morula (E3.5) derived from a mating of a wild-type male with a stella$^{-/-}$ female stained with anti-stella antibody (j) and propidium iodide (k) (l, merge). Stella protein is made from the paternal allele, but not sufficient to rescue the observed phenotype. Scale bar in l (for j-l)=20 μm FIG. 19. Preimplantation development is perturbed without Stella. a, The percentage of embryos developing in vivo to the various stages are given for stella$^{-/-}$ (white bars) and wild-type or stella$^{+/-}$ (black bars) mothers, respectively. Total numbers of embryos examined at each timepoint are given in parentheses. Development of knockout-derived embryos starts to be affected from E1.5 onwards (2-cell stage) and only a low percentage reach the blastocyst stage by E3.5 (b) compared to wild-type-derived embryos (c). d-f, Distribution of stages of embryos cultured in vitro from E1.5 until E4.5 (timepoint of implantation). Similar as in vivo, most embryos from wild-type mothers (black bars) develop to blastocysts (f), while many embryos of stella knockout mothers (white bars) are delayed or show abnormal morphology (e). Total number of embryos examined in d: −/− mothers: 41, wt or +/− mothers: 36. Scale bar=100 μm.
Figure 18:
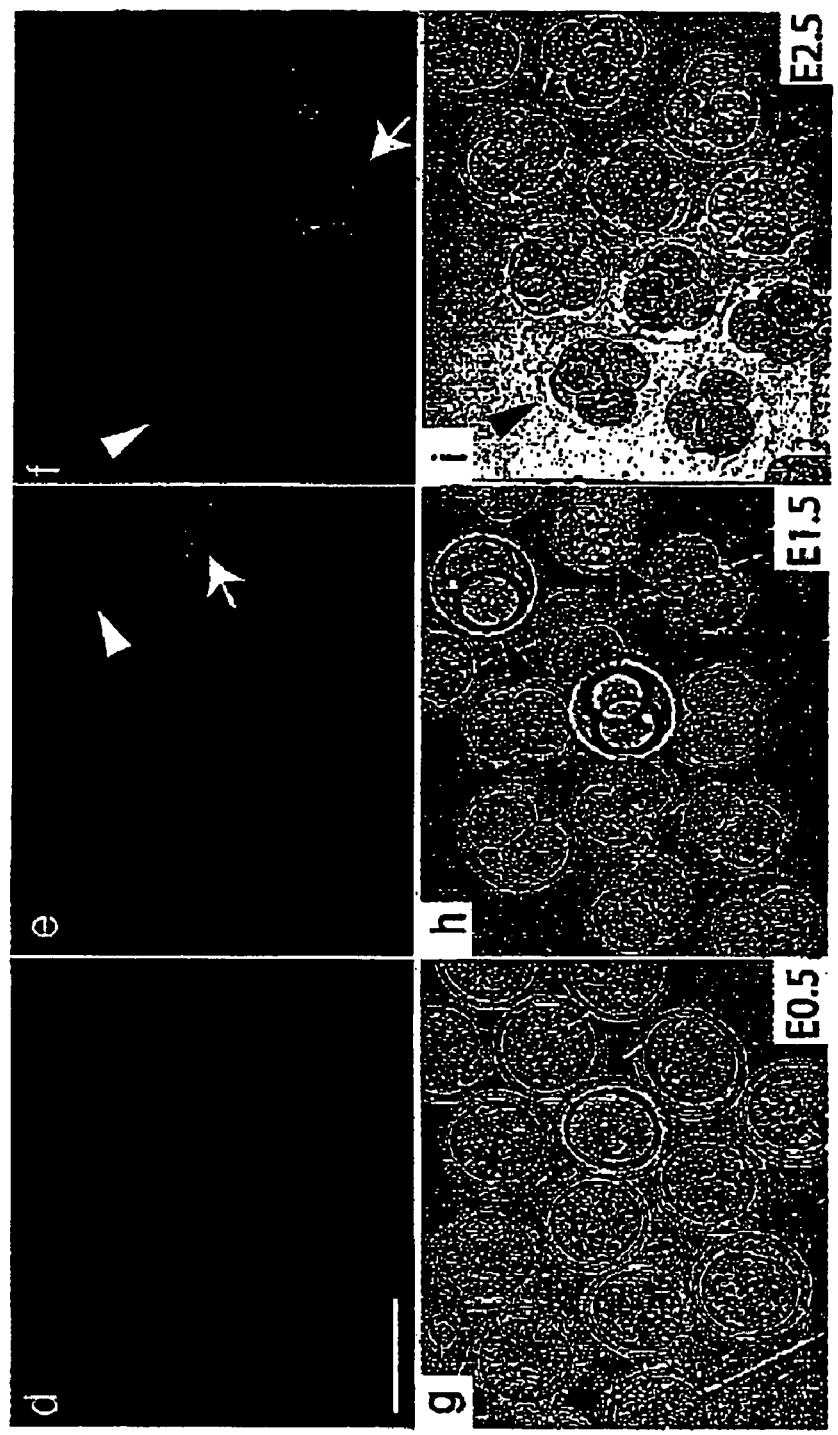
Figure 18:
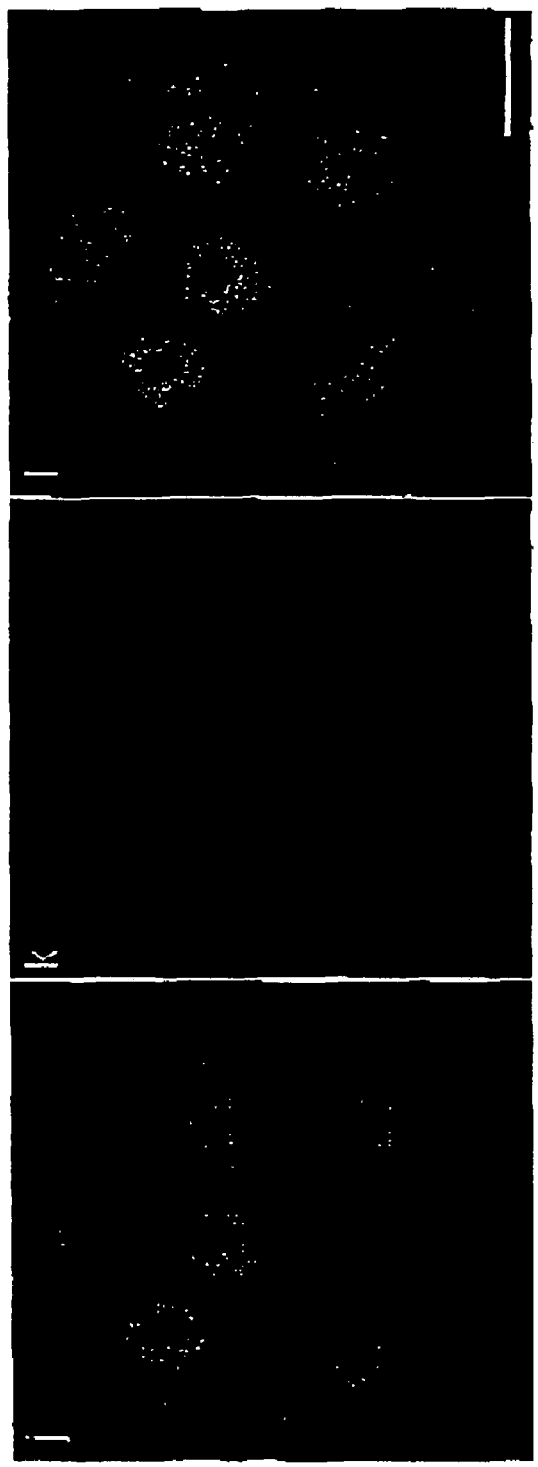

Next, we examined if development progressed normally from oocytes of stella$^{-/-}$ females that lack maternal inheritance of Stella. Despite the ovulation of normal numbers of Stella-deficient oocytes, female stella$^{-/-}$ mice displayed a strongly reduced fertility. When stella$^{-/-}$ females were mated with wild-type males, only a low percentage of matings (detected by vaginal plugs) (24%, FIG. 18a) resulted in full pregnancy and live young. Those females, which failed to become pregnant mated again after approximately 10 days, which reflects lack of embryo implantation in these females and the consequent resumption of the estrous cycle after a period of pseudopregnancy[18]. By contrast, 80% of wild-type females (littermate controls), became pregnant and produced litters following mating (FIG. 18a). Furthermore, even those stella$^{-/-}$ females that became pregnant, produced considerably smaller litters compared to the wild-type females (FIG. 18b). Preliminary results also show reduced fertility in an outbred strain (129SvEv/C57BL/6), although the effect is stronger in inbred 129Sv/Ev mice. This is consistent with previous reports that genetic background can alter the severity of knockout phenotypes[19], including defects in germ cell development[20,21]. These observations demonstrate that embryos derived from Stella-depleted oocytes are affected in development and that stella is a maternal effect gene, because the oocytes were fertilised by normal sperm from wild-type males.

Next we wanted to know, if the Stella protein in preimplantation embryos (FIG. 15)[8] is exclusively maternally inherited and therefore absent in embryos derived from stella$^{-/-}$ females, or if stella expression commences from the paternal allele after fertilisation by wild-type sperm. For this purpose, we made transgenic mice using a stella-GFP reporter transgene (FIG. 18c-i). When a stella-GFP transgenic male was mated with a non-transgenic female, we detected the transgene expression as early as the 2-cell stage (E1.5, FIG. 18e,h), the time when the bulk of embryonic transcription and translation begins[22]. This indicates that the stella gene is transcribed very early during preimplantation development. We confirmed this observation by anti-Stella antibody stainings of E2.5 embryos (FIG. 18j-l), which were derived from mating a wild-type male with a stella$^{-/-}$ female. Therefore, Stella is clearly made in early embryos produced by matings between stella$^{-/-}$ females and wild-type males. But despite this, the majority of Stella-deficient oocytes did not develop normally to term, demonstrating that the onset of stella expression as early as the 2-cell stage from the paternal allele is not sufficient to fully rescue the observed maternal effect phenotype. By contrast, the maternally inherited Stella is sufficient for normal development, as stella$^{-/-}$ mice are born from heterozygous females mated with homozygous males at the same frequency as wild-type mice (see above).

Figure 19:
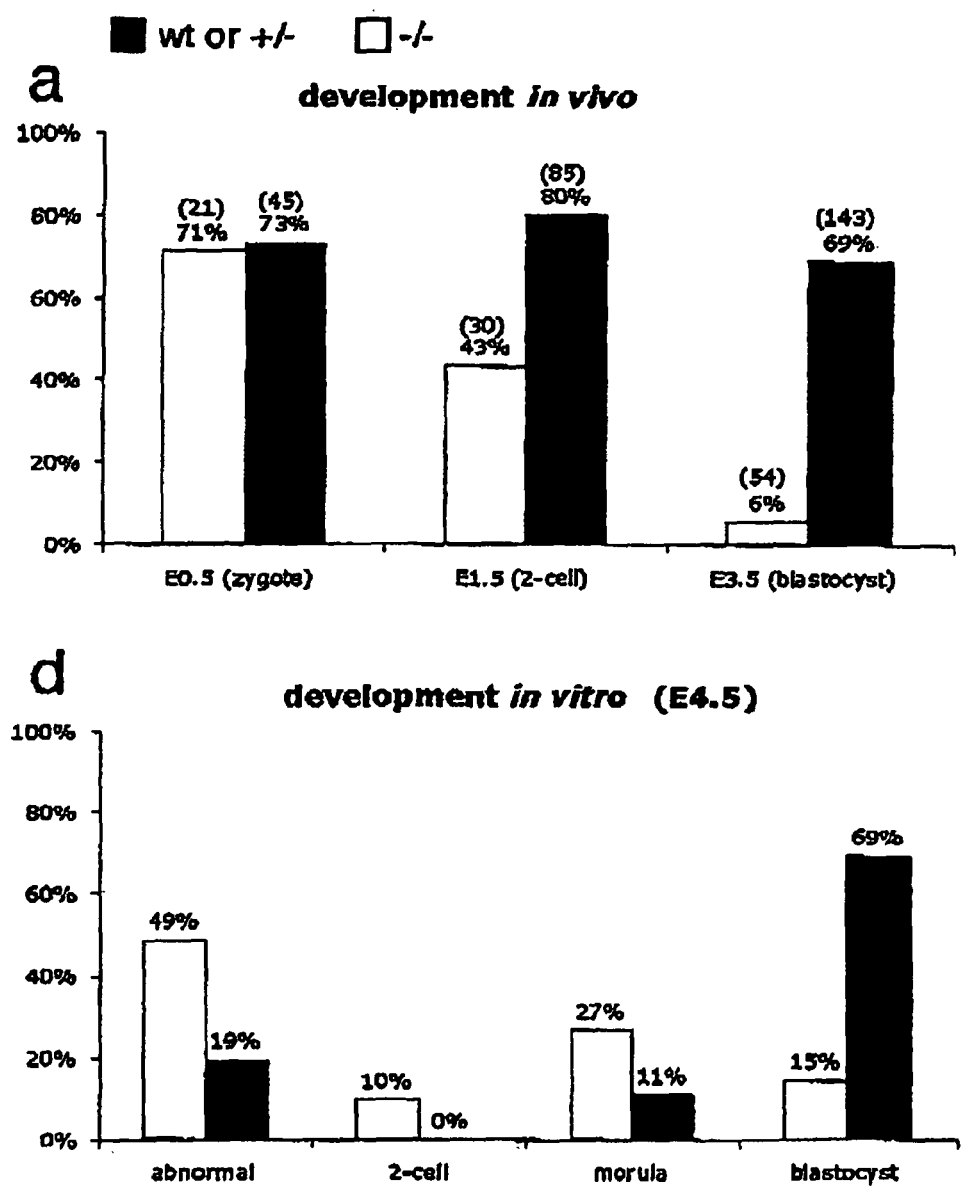
Figure 19:
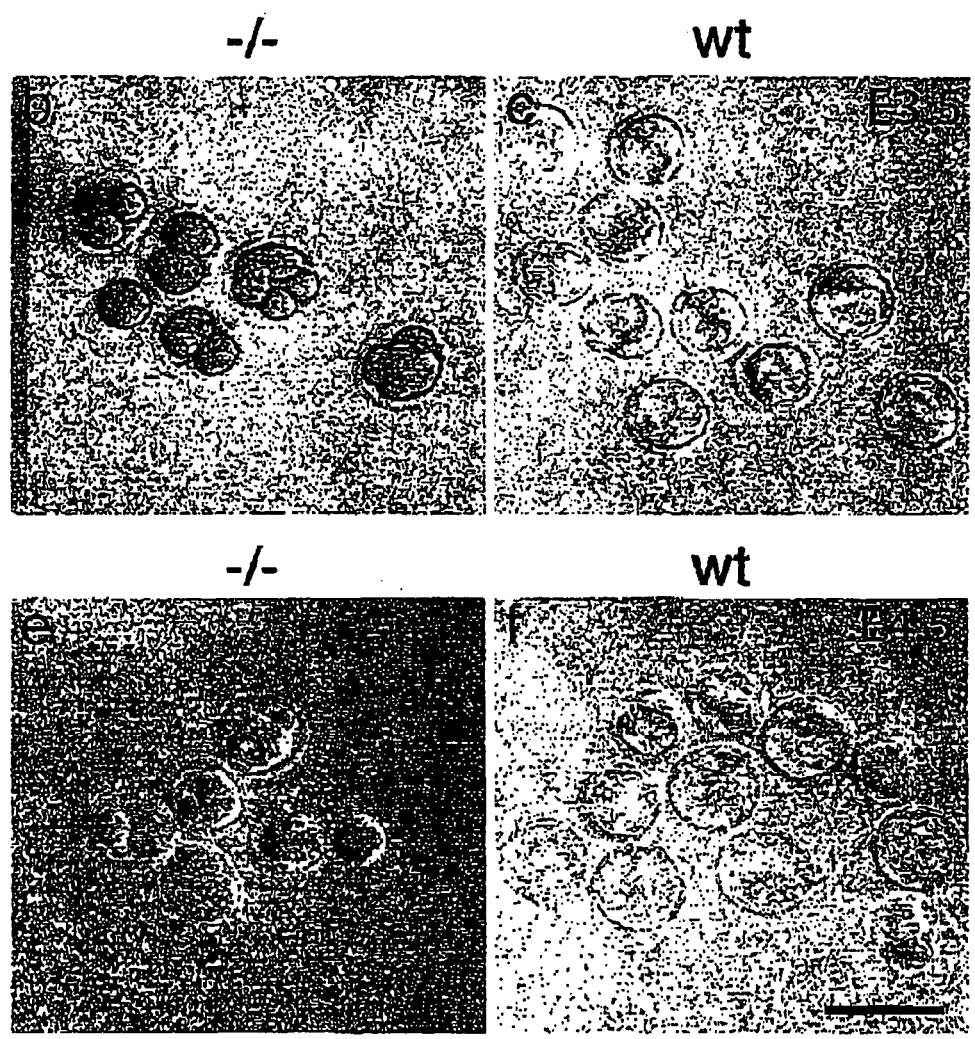

We then addressed the question concerning the embryonic stages at which the absence of Stella affects development. As we have so far not obtained any live young from matings between stella$^{-/-}$ males and stella$^{-/-}$ females, we examined embryos from these matings, and compared it with embryos from matings between wild-type or stella$^{-/-}$ males with wild-type or stella$^{+/-}$ females (FIG. 19). While fertilisation seems to proceed normally in oocytes from stella$^{-/-}$ females, the effects of lacking Stella become evident shortly thereafter, with progressively fewer embryos exhibiting normal development at each time point examined (FIG. 19a). The cumulative manifestation of developmental anomalies are starkly obvious at E3.5, when most of the embryos from controls (69%) reach the blastocyst stage, while only 6% of embryos in stella$^{-/-}$ mothers do so (FIG. 19a-c). This observation was further supported by examination of similar embryos cultured in vitro for 3 days until E4.5, when only 15% of embryos from mutant oocytes reached the blastocyst stage compared to 69% for controls. 49% of mutant embryos were still at the single-cell stage, fragmenting or exhibiting asymmetric or abnormal cleavage. The remainder were found at various stages including 10% at the 2-cell stage and 27% at the morula stage (FIG. 5d-J). Since uterine receptivity for blastocyst implantation is restricted to late E3.5 to early E4.5, only those embryos that reach the blastocyst stage by that time can implant[23,24]. This is consistent with the observation that stella[-/-] females rarely become pregnant and when they do, they produce very small litters. In several cases, stella[-/-] females only become pseudopregnant and resume mating after 10 days, which is indicative of a lack of implanting blastocysts in these females[18].

In conclusion, we demonstrate that the maternal inheritance of Stella is needed for normal embryonic development. Depletion of Stella from the oocytes compromises this process, resulting in a progressive decline in the numbers of blastocyts, fewer implants and a poor yield of viable young. Stella is a basic protein with a SAP-like domain[25] and a splicing factor-like motif and therefore likely to have a role in chromosomal organisation or RNA metabolism. We propose to look for the interacting partners and the biochemical activity of the conserved domains of Stella to elucidate its role in early development. Despite a lack of gross abnormalities in germ cell development in stella[-/-] mice, we cannot rule out subtle effects. One possibility is functional redundancy through compensation by stella-related genes. There are several stella-like sequences in the mouse genome, although these are likely to be pseudogenes (data not shown). STELLA is also expressed in human oocytes[10], where it is likely to play a similar role in early development as in mice. As the highest expression of STELLA is in a human testicular germ cell tumour, this could serve as a diagnostic marker or be of therapeutic value in the future. The conservation of the syntenic chromosomal region harbouring STELLA, together with NANOG and GDF3 on chromosome 12p is noteworthy as it is associated with pluripotency, teratocarcinomas and germ cell tumours in humans. The role of likely coordinated regulation of all key genes within the region may provide evolutionary insights into aspects of germ cell development and germ cell tumours, as well as on pluripotency and maternal effect genes.

REFERENCES

Brady, G. and Iscove, N. N. (1993). Construction of cDNA libraries from single cells. *Methods Enzymol.* 225, 611-623.

Dulac, C. and Axel, R. (1995). A novel family of genes encoding putative pheromone receptors in mammals. *Cell* 83, 195-206.

Ginsburg, M., Snow, M. H. L., and McLaren, A. (1990). Primordial germ cells in the mouse embryo during gastrulation. *Development* 110, 521-528.

Downs, K. M., and Davies, T. (1993). Staging of gastrulating mouse embryos by morphological landmarks in the dissecting microscope. *Development* 118, 1255-1266.

Lawson, K. A., Dunn, N. R., Roelen, B. A. J., Zeinstra, L. M., Davis, A. M., Wright, C. V. E., Korving, J. P. W. F. M., and Hogan, B. L. M. (1999). Bmp4 is required for the generation of primordial germ cells in the mouse embryo. *Genes&Dev.* 13, 424-436.

Yoem, Y. I I., Fuhrmann, G., Ovitt, C. E., Brehm, A., Ohbo, K., Gross, M., Hubner, K., and Scholer, H. R. (1996). Germline regulatory element of Oct-4 specific for the totipotent cycle of embryonal cells. *Development* 1996, 881-894.

1. Weismann, A. Das Keimplasma. Eine theorie der Vereburg. *Jenna. Gustav Fischer* (1892).

2. Eddy, E. M. Germ plasm and the differentiation of the germ cell line. *Int Rev Cytol* 43, 229-80 (1975).

3. Seydoux, G. & Strome, S. Launching the germline in *Caenorhabditis elegans*: regulation of gene expression in early germ cells. *Development* 126, 3275-83. (1999).

4. Wylie, C. Germ cells. *Cell* 96, 165-74. (1999).

5. Lawson, K. A. et al. Bmp4 is required for the generation of primordial germ cells in the mouse embryo. *Genes Dev* 13, 424-36. (1999).

6. Lawson, K. A. & Hage, W. J. Clonal analysis of the origin of primordial germ cells in the mouse. *Ciba Found Symp* 182, 68-84 (1994).

7. Tam, P. P. & Zhou, S. X. The allocation of epiblast cells to ectodermal and germ-line lineages is influenced by the position of the cells in the gastrulating mouse embryo. *Dev Biol* 178, 124-32. (1996).

8. Yoshimizu, T., Obinata, M. & Matsui, Y. Stage-specific tissue and cell interactions play key roles in mouse germ cell specification. *Development* 128, 481-90. (2001).

9. McLaren, A. Signaling for germ cells. *Genes Dev* 13, 373-6. (1999).

10. Ying, Y., Liu, X. M., Marble, A., Lawson, K. A. & Zhao, G. Q. Requirement of Bmp8b for the generation of primordial germ cells in the mouse. *Mol Endocrinol* 14, 1053-63. (2000).

11. Ying, Y., Qi, X. & Zhao, G. Q. Induction of primordial germ cells from murine epiblasts by synergistic action of BMP4 and BMP8B signaling pathways. *Proc Natl Acad Sci USA* 98, 7858-7862. (2001).

12. Ying, Y. & Zhao, G. Q. Cooperation of endoderm-derived BMP2 and extraembryonic ectoderm-derived BMP4 in primordial germ cell generation in the mouse. *Dev Biol* 232, 484-92. (2001).

13. Chiquoine, A. D. The identification, origin and migration of the primordial germ cells in the mouse embryo. *Anat Rec* 118, 135-146 (1954).

14. Ginsburg, M., Snow, M. H. & McLaren, A. Primordial germ cells in the mouse embryo during gastrulation. *Development* 110, 521-8. (1990).

15. MacGregor, G. R., Zambrowicz, B. P. & Soriano, P. Tissue non-specific alkaline phosphatase is expressed in both embryonic and extraembryonic lineages during mouse embryogenesis but is not required for migration of primordial germ cells. *Development* 121, 1487-96. (1995).

16. Nichols, J. et al. Formation of pluripotent stem cells in the mammalian embryo depends on the POU transcription factor Oct4. *Cell* 95, 379-91. (1998).

17. Pesce, M., Gross, M. K. & Scholer, H. R. In line with our ancestors: Oct4 and the mammalian germ. *Bioessays* 20, 722-32. (1998).

18. Yeom, Y. I. et al. Germline regulatory element of Oct4 specific for the totipotent cycle of embryonal cells. *Development* 122, 881-94. (1996).

19. Downs, K. M. & Davies, T. Staging of gastrulating mouse embryos by morphological landmarks in the dissecting microscope. *Development* 118, 1255-66. (1993).

20. Brady, G. & Iscove, N. N. Construction of cDNA libraries from single cells. *Methods Enzymol* 225, 611-23 (1993).

21. Dulac, C. & Axel, R. A novel family of genes encoding putative pheromone receptors in mammals. *Cell* 83, 195-206. (1995).

22. Frohman, M. A., Boyle, M. & Martin, G. R. Isolation of the mouse Hox-2.9 gene; analysis of embryonic expression suggests that positional information along the anterior-posterior axis is specified by mesoderm. *Development* 110, 589-607. (1990).

23. Deblandre, G. A. et al. Expression cloning of an interferon-inducible 17-kDa membrane protein implicated in the control of cell growth. *J Biol Chem* 270, 23860-6. (1995).

24. Friedman, R. L., Manly, S. P., McMahon, M., Kerr, I. M. & Stark, G. R. Transcriptional and posttranscriptional regulation of interferon-induced gene expression in human cells. *Cell* 38, 745-55. (1984).

25. Evans, S. S., Collea, R. P., Leasure, J. A. & Lee, D. B. IFN-alpha induces homotypic adhesion and Leu-13 expression in human B lymphoid cells. *J Immunol* 150, 736-47. (1993).

26. Evans, S. S., Lee, D. B., Han, T., Tomasi, T. B. & Evans, R. L. Monoclonal antibody to the interferon-inducible protein Leu-13 triggers aggregation and inhibits proliferation of leukemic B cells. *Blood* 76, 2583-93. (1990).

27. Aravind, L. & Koonin, E. V. SAP—a putative DNA-binding motif involved in chromosomal organization. *Trends Biochem Sci* 25, 1124. (2000).

28. Gurdon, J. B., Lemaire, P. & Kato, K. Community effects and related phenomena in development. *Cell* 75, 831-4. (1993).

29. Reid, L. E. et al. A single DNA response element can confer inducibility by both alpha- and gamma-interferons. *Proc Natl Acad Sci USA* 86, 840-4. (1989).

30. Kita, M. et al. [Expression of cytokines and interferon-related genes in the mouse embryo]. *C R Seances Soc Biol Fil* 188, 593-600 (1994).

31. Gomperts, M., Garcia-Castro, M., Wylie, C. & Heasman, J. Interactions between primordial germ cells play a role in their migration in mouse embryos. *Development* 120, 135-41. (1994).

32. Herrmann, B. G., Labeit, S., Poustka, A., King, T. R. & Lehrach, B. Cloning of the T gene required in mesoderm formation in the mouse. *Nature* 343, 617-22. (1990).

33. Herrmann, B. G. Expression pattern of the Brachyury gene in whole-mount TWis/TWis mutant embryos. *Development* 113, 913-17

34. Crossley, P. H. & Martin, G. R. The mouse Fgf8 gene encodes a family of polypeptides and is expressed in regions that direct outgrowth and patterning in the developing embryo. *Development* 121, 439-51. (1995).

35. Barnes, J. D., Crosby, J. L., Jones, C. M., Wright, C. V. & Hogan, B. L. Embryonic expression of Lim-1, the mouse homolog of Xenopus Xlim-1, suggests a role in lateral mesoderm differentiation and neurogenesis. *Dev Biol* 161, 168-78. (1994).

36. Fujii, T. et al. Expression patterns of the murine LIM class homeobox gene lim1 in the developing brain and excretory system. *Dev Dyn* 199, 73-83. (1994).

37. Bastian, H. & Gruss, P. A murine even-skipped homologue, Evx 1, is expressed during early embryogenesis and neurogenesis in a biphasic manner. *Embo J* 9, 1839-52. (1990).

38. Rogers, M. B., Hosler, B. A. & Gudas, L. J. Specific expression of a retinoic acid-regulated, zinc-finger gene, Rex-1, in preimplantation embryos, trophoblast and spermatocytes. *Development* 113, 815-24. (1991).

39. Sutton, J. et al. Genesis, a winged helix transcriptional repressor with expression restricted to embryonic stem cells. *J Biol Chem* 271, 23126-33. (1996).

40. Cox, D. N. et al. A novel class of evolutionarily conserved genes defined by piwi are essential for stem cell self-renewal. *Genes Dev* 12, 3715-27. (1998).

41. Fujiwara, Y. et al. Isolation of a DEAD-family protein gene that encodes a murine homolog of *Drosophila vasa* and its specific expression in germ cell lineage. *Proc Natl Acad Sci USA* 91, 12258-62. (1994).

42. Dixon, K. E. Evolutionary aspects of primordial germ cell formation. *Ciba Found Symp* 182, 92-110 (1994).

43. Mahowald, A. P. Assembly of the Drosophila germ plasm. *Int Rev Cytol* 203, 187-213 (2001).

44. Nieuwkoop, P. D. & Satasurya, L. A. Primordial germ cells in the chordates. *Cambridge University Press, Cambridge, UK* (1979).

45. Johnson, A. D., Bachvarova, R. F., Drum, M. & Masi, T. Expression of axolotl daz1 ma, a marker of germ plasm: widespread maternal rna and onset of expression in germ cells approaching the gonad. *Dev Biol* 234, 402-15. (2001).

46. Johnson, A. D., Bachvarova, R. F., Masi, T. & Drum, M. Expression of Vasa and Daz-like genes demonstrate that Axolotl primordial germ cells (PGCs) are not predetermined. *Germ cells* Cold Spring harbor laboratory, 61 (2000).

47. Toyooka, Y. et al. Expression and intracellular localization of mouse Vasa-homologue protein during germ cell development. *Mech Dev* 93, 139-49. (2000).

48. Saitou, M. et al. Occludin-deficient embryonic stem cells can differentiate into polarized epithelial cells bearing tight junctions. *J Cell Biol* 141, 397-408. (1998).

49. Henrique, D. et al. Expression of a Delta homologue in prospective neurons in the chick. *Nature* 375, 787-90. (1995).

50. Wilkinson, D. G. & Nieto, M. A. Detection of messenger RNA by in situ hybridization to tissue sections and whole mounts. *Methods Enzymol* 225, 361-73 (1993).

51. Winnier, G., Blessing, M., Labosky, P. A. & Hogan, B. L. Bone morphogenetic protein-4 is required for mesoderm formation and patterning in the mouse. *Genes Dev* 9, 2105-16. (1995).

REFERENCES FOR EXAMPLES 11 TO 20

1. K A Lawson, W J Hage: Clonal analysis of the origin of primordial germ cells in the mouse. Germline development. In *Wiley, Chichester* (Ciba Foundation Symposium 182) 1994, 68-91
2. A McLaren: Signaling for germ cells. *Genes Dev* 1999, 13: 373-376
3. K A Lawson, N R Dunn, B A J Roelm, L M Zeinstra, A M Davies, C V E Wright, J P W F M Korving, B L M Hogan: Bmp4 is required for the generation of primordial germ cells in the mouse embryo. *Genes Dev* 1999, 13: 424-436
4. Y Ying, X M Lui, A Marble, K A Lawson, G Q Zhao: Requirement of Bmp8b for the generation of primordial germ cells in the mouse. *Mol Endocrinol* 2000, 14: 1053-1063
5. H Chang, M M Matzuk: Smad5 is required for mouse primordial germ cell development. *Mech Dev* 2001, 104: 61-67
6. K D Tremblay, N R Dunn, E J Robertson: Mouse embryos lacking Smad1 signals display defects in extraembryonic tissues and germ cell formation. *Development* 2001, 128: 3609-3621
7. Y Ying, G Q Zhao: Cooperation of endoderm-derived BMP2 and extraembryonic ectoderm-derived BMP4 in primordial germ cell generation in the mouse. *Dev Biol* 2001, 232 (2): 484-492
8. M Saitou, S C Barton, M A Surani: A molecular programme for the specification of germ cell fate in mice. *Nature* 2002, 418: 293-300
9. M Ginsburg, M H L Snow, A McLaren: Primordial germ cells in the mouse embryo during gastrulation. *Development* 1990, 110: 521-528
10. M Sato, T Kimura, K Kurokawa, Y Fujita, K Abe, M Masubara, T Yasunaga, A Ryo, M Yamamoto, T Nakano: Identification of PGC7, a new gene expressed specifically in preimplantation embryos and germ cells. *Mech Dev* 2002, 113: 91-94

11. A R Lewin, L E Reid, M McMahon, G R Stark, I M Kerr: Molecular analysis of a human interferon-inducible gene family. *Eur J Biochem* 1991, 199: 417-423
12. R L Friedman, S P Manley, M Mcahon, I M Kerr, G R Stark: Transcriptional and posttranscriptional regulation of interferon-induced gene expression in human cells. *Cell* 1984, 38: 745-755
13. J M Kelly, C S Gilbert, G R Stark, I M Kerr: Differential regulation of interferon-induced mRNAs and c-myc mRNA by alpha- and gamma-interferons. *Eur J Biochem* 1985, 153: 367-371
14. S S Evans, D B Lee, T Han, T B Tomasi, R L Evans: Monoclonal antibody to the interferon-inducible protein Leu-13 triggers aggregation and inhibits proliferation of leukemic B cells. *Blood* 1990, 76 (12): 2583-2593
15. S S Evans, R P Collea, J A Leasure, D B Lee: IFN-a induces homotypic adhesion and Leu-13 expression in human B lymphoid cells. *J Immunol* 1993, 150: 736-747
16. D J Hayzer, E Brinson, M S Runge: A rat beta-interferon-induced mRNA: sequence characterization. *Gene* 1992, 117 (2): 227-228
17. J K Pru, K J Austin, A L Haas, T R Hansen: Pregnancy and interferon-tau upregulate gene expression of members of the 1-8 family in the bovine uterus. *Biol Reprod* 2001, 65 (5): 1471-1480
18. L E Reid, A H Brasnett, C S Gilbert, A C G Porter, D R Gewert, G R Stark, I M Kerr: A single DNA response elemnt can confer inducibility by both alpha- and gamma-interferons. *Proc Natl Acad Sci USA* 1989, 86: 840-844
19. G R Stark, I M Kerr, B R G Williams, R H Silverman, R D Schreiber: How cells respond to interferons. *Annu Rev Biochem* 1998, 67: 227-264
20. D P Barlow, B J Randle, D C Burke: Interferon synthesis in the early post-implantation mouse embryo. *Differentiation* 1984, 27: 229-235
21. M Kita, K Tanaka, K Shinmura, Y Tanaka, Y Liu, J Imanishi: Expression of cytokines and interferon-related genes in the mouse embryo. *C.R. Seances Soc. Biol. Fil.* 1994, 188 (5-6): 593-600.
22. K M Downs, T Davies: Staging of gastrulating mouse embryos by morphological landmarks in the dissecting microscope. *Development* 1993, 118: 1255-1266
23. D G Wilkinson, M A Nieto: Detection of messenger RNA by in situ hybridisation to tissue sections and whole mounts. *Methods Enzymol* 1993, 225: 361-373
24. D Henrique, J Adam, A Myat, A Chitnis, J Lewis, D Ish-Horowicz: Expression of a Delta homologue in prospective neurons in the chick. *Nature* 1995, 375: 787-790
25. G Brady, N N Iscove: Construction of cDNA libraries from single cells. *Methods Enzymol* 1993, 225: 611-623

REFERENCES FOR EXAMPLES 21 TO 25

1. Surani, M. A. Reprogramming of genome function through epigenetic inheritance. *Nature* 414, 122-8 (2001).
2. Wu, X. et al. Zygote arrest 1 (Zar1) is a novel maternal-effect gene critical for the oocyte-to-embryo transition. *Nat Genet* 33, 187-91 (2003).
3. Tong, Z. B. et al. Mater, a maternal effect gene required for early embryonic development in mice. *Nat Genet* 26, 267-8 (2000).
4. Howell, C. Y. et al. Genomic imprinting disrupted by a maternal effect mutation in the Dnmt1 gene. *Cell* 104, 829-38 (2001).
5. Christians, E., Davis, A. A., Thomas, S. D. & Benjamin, I. J. Maternal effect of Hsf1 on reproductive success. *Nature* 407, 693-4 (2000).
6. Gurtu, V. E. et al. Maternal effect for DNA mismatch repair in the mouse. *Genetics* 160, 271-7 (2002).
7. Burns, K. H. et al. Roles of NPM2 in chromatin and nucleolar organization in oocytes and embryos. *Science* 300, 633-6 (2003).
8. Sato, M. et al. Identification of PGC7, a new gene expressed specifically in preimplantation embryos and germ cells. *Mech Dev* 113, 91-4 (2002).
9. Saitou, M., Barton, S. C. & Surani, M. A. A molecular programme for the specification of germ cell fate in mice. *Nature* 418, 293-300 (2002).
10. Goto, T. et al. Identification and characterisation of known and novel transcripts expressed during the final stages of human oocyte maturation. *Mol Reprod Dev* 62, 13-28 (2002).
11. Looijenga, L. H. et al. Role of gain of 12p in germ cell tumour development. *Apmis* 111, 161-71; discussion 172-3 (2003).
12. Mitsui, K. et al. The Homeoprotein Nanog Is Required for Maintenance of Pluripotency in Mouse Epiblast and ES Cells. *Cell* 113, 631-42 (2003).
13. Chambers, I. et al. Functional expression cloning of nanog, a pluripotency sustaining factor in embryonic stem cells. *Cell* 113, 643-55 (2003).
14. Caricasole, A. A. et al. Human growth-differentiation factor 3 (hGDF3): developmental regulation in human teratocarcinoma cell lines and expression in primary testicular germ cell tumours. *Oncogene* 16, 95-103 (1998).
15. Spellman, P. T. & Rubin, G. M. Evidence for large domains of similarly expressed genes in the *Drosophila* genome. *J Biol* 1, 5 (2002).
16. Ginsburg, M., Snow, M. H. & McLaren, A. Primordial germ cells in the mouse embryo during gastrulation. *Development* 110, 521-8 (1990).
17. Fox, N., Damjanov, I., Martinez-Hernandez, A., Knowles, B. B. & Solter, D. Immunohistochemical localization of the early embryonic antigen (SSEA-1) in postimplantation mouse embryos and fetal and adult tissues. *Dev Biol* 83, 391-8 (1981).
18. Johnson, M. H. & Everitt, B. J. *Essential reproduction*, xi, 377 (Blackwell Scientific, Oxford, 1988).
19. Montagutelli, X. Effect of the genetic background on the phenotype of mouse mutations. *J Am Soc Nephrol* 11 Suppl 16, S101-5 (2000).
20. Lawson, K. A. et al. Bmp4 is required for the generation of primordial germ cells in the mouse embryo. *Genes Dev* 13, 424-36 (1999).
21. Winnier, G., Blessing, M., Labosky, P. A. & Hogan, B. L. Bone morphogenetic protein-4 is required for mesoderm formation and patterning in the mouse. *Genes Dev* 9, 2105-16 (1995).
22. Nothias, J. Y., Majumder, S., Kaneko, K. J. & DePamphilis, M. L. Regulation of gene expression at the beginning of mammalian development. *J Biol Chem* 270, 22077-80 (1995).
23. Rugh, R. *The mouse: Its Reproduction and Development*, (Oxford University Press, Oxford England; New York, 1990).
24. McLaren, A. & Michie, D. Studies on the transfer of fertilized mouse eggs to uterine foster-mothers. *J Exp Biol* 33, 394-416 (1956).
25. Aravind, L. & Koonin, E. V. SAP—a putative DNA-binding motif involved in chromosomal organization. *Trends Biochem Sci* 25, 112-4 (2000).
26. Chang, H. & Matzuk, M. M. Smad5 is required for mouse primordial germ cell development. *Mech Dev* 104, 61-7 (2001).

27. Fukuda, M. et al. CRM1 is responsible for intracellular transport mediated by the nuclear export signal. *Nature* 390, 308-11 (1997).

Each of the applications and patents mentioned in this document, and each document cited or referenced in each of the above applications and patents, including during the prosecution of each of the applications and patents ("application cited documents") and any manufacturer's instructions or catalogues for any products cited or mentioned in each of the applications and patents and in any of the application cited documents, are hereby incorporated herein by reference. Furthermore, all documents cited in this text, and all documents cited or referenced in documents cited in this text, and any manufacturer's instructions or catalogues for any products cited or mentioned in this text, are hereby incorporated herein by reference.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the claims.

The invention claimed is:

1. An antibody that specifically binds to a Fragilis polypeptide having at least 90% identity with the sequence of SEQ ID NO: 2 that specifically binds to the extracellular N terminal domain of the sequence of SEQ ID NO: 2, wherein the antibody is a humanized antibody.

2. An antibody according to claim 1, wherein the antibody comprises an antibody fragment selected from the group consisting of an Fv; ScFv; Fab'; and F(ab')2.

3. An antibody according to claim 1, wherein the antibody further comprises a label.

4. An antibody according to claim 1, wherein the antibody is capable of selectively binding to the surface of a pluripotent cell.

5. An antibody that specifically binds to a Fragilis polypeptide having at least 90% identity with the sequence of SEQ ID NO: 2 that specifically binds to the extracellular C terminal domain of the sequence of SEQ ID NO: 2, wherein the antibody is a humanized antibody.

6. An antibody according to claim 5, wherein the antibody comprises an antibody fragment selected from the group consisting of an Fv; ScFv; Fab'; and F(ab')2.

7. An antibody according to claim 5, wherein the antibody further comprises a label.

8. An antibody according to claim 5, wherein the antibody is capable of selectively binding to the surface of a pluripotent cell.

9. A method for isolating a pluripotent cell from a population of cells, comprising the steps of:
  screening the population of cells for cells that express a polypeptide having at least 90% identity with the sequence SEQ ID NO: 2;

identifying those cells that express a polypeptide having at least 90% identity with the sequence SEQ ID NO: 2 as putative pluripotent cells, wherein the step of identifying the putative pluripotent cells comprises exposing the population of cells to an antibody that specifically binds to a Fragilis polypeptide having at least 90% identity with the sequence SEQ ID NO: 2; and isolating the putative pluripotent cells from the population of cells.

10. A method according to claim 9, wherein the antibody specifically binds to the extracellular regions of a polypeptide having at least 90% identity with the sequence SEQ ID NO: 2.

11. A method according to claim 9, wherein the antibody is labeled with a fluorophore.

12. A method according to claim 9, wherein the population of cells is selected from the group consisting of embryonic tissue; adult tissue; tissues grown in culture and cell preparations derived from any of the aforementioned.

13. A method according to claim 9 wherein the pluripotent cell is selected from a stem cell; a primordial germ cell; an embryonic germ (EG) cell; and an embryonic stem (ES) cell.

* * * * *